US006489136B1

(12) United States Patent
Zervos

(10) Patent No.: US 6,489,136 B1
(45) Date of Patent: Dec. 3, 2002

(54) CELL PROLIFERATION RELATED GENES

(75) Inventor: Antonis S. Zervos, Woburn, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/075,460

(22) Filed: May 8, 1998

Related U.S. Application Data

(60) Provisional application No. 60/046,077, filed on May 9, 1997.

(51) Int. Cl.[7] ......................... C12N 15/12; C12N 15/63; C12N 1/00; C12N 5/10; C12P 21/02; C07H 21/00
(52) U.S. Cl. ................ 435/69.1; 435/320.1; 435/252.3; 435/252.33; 435/254.11; 435/325; 435/410; 536/23.5; 536/24.3; 536/24.31
(58) Field of Search ..................... 536/23.5, 24.3, 536/24.31; 435/320.1, 252.3, 252.33, 325, 254.11, 410, 69.1

(56) References Cited

U.S. PATENT DOCUMENTS 6,004,794 A    12/1999   Karran et al. ............... 435/226

OTHER PUBLICATIONS

Callard et al. The Cytokine FactsBook. San Diego: Academic Press. p. 31, 1994.*
Atkinson, S. et al., Expression in *Escherichia coli* of fragments of the coiled–coil rod domain of rabbit myosin: influence of different regions of the molecule on aggregation and paracrystal formation, *J. Cell. Science*, 99:823–836, 1991.
Bange, F. et al., "IFP 35 Is an Interferon–induced Leucine Zipper Protein That Undergoes Interferon–regulated Cellular Redistribution", *J. Biol. Chem.*, 269:1091–1098, Jan. 14, 1994.
Baranger A. et al., "Mechanism of DNA–binding enhancement by the human T–cell leukaemia virus transactivator Tax", *Nature*, 376:606–608, Aug. 17, 1995.
Boyd, Janice M. et al., "A region in the C–terminus of adenovirus 2/5 E1a protein is required for assoc. with a cellular phosphoprotein and imp. for the negative modulation of T24–ras mediated trans., tumorigenesis and metastasis", *EMBO Journal*, 12:469–478, 1993.
Defeo, Deborah et al., "Cloning of cDNAs for cellular proteins that bind to the retinoblastoma gene product", *Nature*, 352:251–254, Jul. 18, 1991.
Du, Wei et al., "The high mobility group protein HMG I(Y) can stimulate or inhibit DNA binding of distinct transcription factor ATF–2 isoforms", *Proc. Natl. Acad. Sci. USA*, 91:11318–11322, Nov. 1994.
Faruqui, A. et al., "Structural Studies on the Conformations of Myosin", *Adv. Exp. Med. Biol.*, 332: 81–89, 1993.

Figge, James et al., "Prediction of Similar Transforming Regions in Simian Virus 40 Large T, Adenovirus E1A, and myc Oncoproteins", *J. Virol.*, 62:1814–1818, May 1988.
Hurlin, Peter J. et al., "Mad3 and Mad4: novel Max–interacting transcriptional repressors that supress c–myc dependent trans. and are expressed during neural and epidermal differentiation", *EMBO J.*, 14:5646–5659, 1995.
Lüscher, Bernhard et al., "New Light on Myc and Myb. Part I. Myc", *Genes & Dev.*, 4:2025–2035, 1990.
Perini, Giovanni et al., "Recognition of bZIP proteins by the human T–cell leukaemia virus transactivator Tax", *Nature*, 376:602–605, Aug. 17, 1995.
Rabbitts, Terence H., "Translocations, Master Genes, and Differences between the Origins of Acute and Chronic Leukemias", *Cell*, 67:641–644, Nov. 15, 1991.
Sawyers, Charles L. et al., "Chronic Myelomonocytic Leukemia: Tel–a–Kinase What Ets All About", *Cell*, 77:171–173, Apr. 22, 1994.
Schaeper, Ute et al., "Molecular cloning and characterization of a cellular phosphoprotein that interacts with a conserved C–terminal domain of adenovirus E1A involved in negative modulation of oncogenic transformation", *Proc. Natl. Acad. Sci. USA*, 92: 10467–10471, Nov. 1995.
Shan, Bei et al., "Molecular Cloning of Cellular Genes Encoding Retinoblastoma–Associated Proteins: Identification of a Gene with Prop. of the Trans. Factor E2F", *Mol. Cell. Biol.*, 12(12):5620–5631, Dec. 1992.
Shapiro, David N. et al., "Assignment of the Human MAD and MXI1 Genes to Chromosomes 2p12–p13 and 10q24–q25", *Genomics*, 23:282–285, 1994.
Sollerbrant, Kerstin et al., "The CtBP binding domain in the adenovirus E1A protein controls CR1–dependent transactivation", *Nucleic Acids Research*, 24:2578–2584, 1996.
Taya, Yoichi, "RB Kinases and RB–binding proteins: new points of view", *Trends Biochem. Sci.*, 22:14–17, 1997.
Yen, Andrew et al., "Concentration of RB protein in nucleus vs. cytoplasm is stable as phosphorylation of RB changes during the cell cycle and differentiation", *Eur. J. Cell. Biol.*, 72:159–165, Feb. 1997.

(List continued on next page.)

*Primary Examiner*—Gabrielle Bugalsky
(74) *Attorney, Agent, or Firm*—Fish & Richardson PC

(57) ABSTRACT

The present invention relates to three novel cancer related genes, Nmi, Omi and Rim. The Nmi gene encodes a myc gene product-binding protein. The Omi gene encodes a mammalian serine protease protein comprising an amino terminal regulatory domain, which includes a signal peptidase site, a triple repeat motif, an SH3 binding domain, and a consensus Mxi2/p38 kinase phosphorylation site, and a carboxy terminus serine protease catalytic domain. The retinoblastoma-interacting myosin-like gene (Rim gene) encodes a retinoblastoma binding protein comprising two leucine zipper structures, an RB family binding motif, an E1A/CtBP binding motif, and four nuclear localization sequences. Described herein are isolated and antisense nucleic acids molecules, recombinant expression vectors, host cells and non-human transgenic animals containing an insertion or a disruption of the Nmi, Omi and Rim genes. Diagnostic, screening and therapeutic methods utilizing the compositions of the invention are also provided.

32 Claims, 10 Drawing Sheets

OTHER PUBLICATIONS

Zumbrunn, Jürg et al., "Primary structure of a putative serine protease specific for IGC–binding proteins", *FEBS Letters*, 398:187–192, 1996.

Bao, J. et al., "Isolation and Characterization of Nmi, a Novel Partner of Myc Proteins", *Oncogen*, 12 (10) 2171–2176, May 16, 1996.

Martinovski, G. et al., "Inhibition of Doxorubicin Induced Cell Death by NMI, a MYC Interacting Protein", *Blood*, vol. 88, No. 10 Part 1, Supp. [1]: pp. 2637, Nov. 15, 1996.

Wang, X. et al., "IFP 35 Forms Complexes with B–ATF, a Member of the AP1 Family of Transcription Factors", *Biochemical and Biophysical Research Communications*, 229, 316–322, Oct., 1996.

Wilson, R. et al., "2.2 Mb of Contiguous Nucleotide Sequence from Chromosome III of C. Elegans", *Nature* vol. 368, pp. 32–38, Mar., 1999.

* cited by examiner (SEQ ID NO: 1)

```
      GGATCCGCGTGCTAAAGAAAAATCGCCGTTAAAGCAGTTTTCTTTTTCACTGTCTTTTTC    60
      TTTTCGCGGGGAACCCAGCTGTTCCTGCGAGGGCCACCTCCTCAGGAAGACCCCGCAGCT   120
      CTCCCGCGGCGCTTCTGCAGGAGGCAGCGACAGTTTCGAGAACCCGGGCCTTCCCCTCCC   180
      AGTGCCTCCGGGGGTTCGCGTTTCAGGCGCTCGTGTTTCCGGGAAGGGCAGGCGCGCTG    240
      GGCCTTGGGGAGCTGCGCTCGGCGGGCGGACCGGGGGATCATGGAAGCTGATAAAGATGA   300
                                            M  E  A  D  K  D  D
      CACACAACAAATTCTTAAGGAGCATTCGCCAGATGAATTTATAAAAGATGAACAAAATAA   360
   8   T  Q  Q  I  L  K  E  H  S  P  D  E  F  I  K  D  E  Q  N  K
      GGGACTAATTGATGAAATTACAAAGAAAAATATTCAGCTAAAGAAGGAGATCCAAAAGCT   420
  28   G  L  I  D  E  I  T  K  K  N  I  Q  L  K  K  E  I  Q  K  L
      TGAAACGGAGTTACAAGAGGCTACCAAAGAATTCCAGATTAAAGAGGATATTCCTGAAAC   480
  48   E  T  E  L  Q  E  A  T  K  E  F  Q  I  K  E  D  I  P  E  T
      AAAGATGAAATTCTTATCAGTTGAAACTCCTGAGAATGACAGCCAGTTGTCAAATATCTC   540
  68   K  M  K  F  L  S  V  E  T  P  E  N  D  S  Q  L  S  N  I  S
      CTGTTCGTTTCAAGTGAGCTCGAAAGTTCCTTATGAGATACAAAAAGGACAAGCACTTAT   600
  88   C  S  F  Q  V  S  S  K  V  P  Y  E  I  Q  K  G  Q  A  L  I
      CACCTTTGAAAAAGAAGAAGTTGCTCAAAATGTGGTAAGCATGAGTAAACATCATGTACA   660
 108   T  F  E  K  E  E  V  A  Q  N  V  V  S  M  S  K  H  H  V  Q
      GATAAAAGATGTAAATCTGGAGGTTACGGCCAAGCCAGTTCCATTAAATTCAGGAGTCAG   720
 128   I  K  D  V  N  L  E  V  T  A  K  P  V  P  L  N  S  G  V  R
      ATTCCAGGTTTATGTAGAAGTTTCTAAAATGAAAATCAATGTTACTGAAATTCCTGACAC   780
 148   F  Q  V  Y  V  E  V  S  K  M  K  I  N  V  T  E  I  P  D  T
      ACTGCGTGAAGATCAAATGAGAGACAAACTAGAGCTGAGCTTTTCAAAGTTCCGAAATGG   840
 168   L  R  E  D  Q  M  R  D  K  L  E  L  S  F  S  K  F  R  N  G
      AGGCGGAGAGGTGGACCGCGTGGACTATGACAGACAGTCCGGGAGTGCAGTCATCACGTT   900
 188   G  G  E  V  D  R  V  D  Y  D  R  Q  S  G  S  A  V  I  T  F
      TGTGGAGATTGGAGTGGCTGACAAGATTTTGAAAAAGAAAGAATACCCTCTTTATATAAA   960
 208   V  E  I  G  V  A  D  K  I  L  K  K  K  E  Y  P  L  Y  I  N
      TCAAACCTGCCATAGAGTTACTGTTTCTCCATACACAGAAATACACTTGAAAAAGTATCA  1020
 228   Q  T  C  H  R  V  T  V  S  P  Y  T  E  I  H  L  K  K  Y  Q
      GATATTTTCAGGAACATCTAAGAGGACAGTGCTTCTGACAGGAATGGAAGGCATTCAAAT  1080
 248   I  F  S  G  T  S  K  R  T  V  L  L  T  G  M  E  G  I  Q  M
      GGATGAAGAAATTGTGGAGGATTTAATTAACATTCACTTTCAACGGGCAAAGAATGGAGG  1140
 268   D  E  E  I  V  E  D  L  I  N  I  H  F  Q  R  A  K  N  G  G
      TGGAGAAGTAGATGTGGTCAAGTGTTCTCTAGGTCAACCTCACATAGCATACTTTGAAGA  1200
 288   G  E  V  D  V  V  K  C  S  L  G  Q  P  H  I  A  Y  F  E  E
      ATAGACTTAACAGAATCATGAAAACTATAGCTTTTAACCCGGATTACTGTAAATGTTTG   1260
 308   *
      ACAAGAATGAATATGCTTTTCCTTAAAAAATGAAAACTTTAATTTTTACCATCCATTTAT  1320
      GTTTAGATACAAAACTTATTTCCATGTTTCTGAATCTTCTTTGTTTCAAATGGTGCTGCA  1380
      TGTTTTCAACTACAATAAGTGCACTGTAATAAAAAGTTTTGTTTAT               1426
```

FIG. 1

A2
1
M E A D K D D T Q Q I L K E H S P D E F I K D E Q N K G L I D E I T K K N I Q L 40
  + |   + + +   + |   + |         |       +   + + | | + | | |     | |
Q A F E N E K E Q E R E E Q L A K A M E K L N S E Q N I L D E V T K K L E Q S
    104
CEF59

K K E I Q K L E T E L Q E A T K E F Q I K E D I P E T K M K F L S V E T P E N D 80
+ + | +         + | |   | + +   +     |             |       |   +   +   |
E E E V L A A R G A I Q E L T E K L E E S E K E T S T A K T E L E A V S K K L D 86                                  102
S Q L S N I S C S F Q V S S K V P Y E I Q K G Q A L I T F E K E E V A Q N V V S 120
|   + + +                                 | |   | | | | |   + | |     | +
S S E T S L (SEQ ID NO: 2)                G S A L I T F D D P K V A E Q V L Q
        188                               IFP35  79

M S K H H V Q I K D V N L E V T A K P V P L N S G V R F Q V Y V E V S K M K I N 160
    + |   +   + + +     |   | |     + | +   |             | |   + + |   + +
Q K E H T I N M E E C R L R V Q V Q P L E L P M V T T I Q V S S Q L S G R R V L

V T E I P D T L R E D Q M R D K L E L S F S K F R N G G G E V D R V D Y D R Q S 200
| |   |     + |     +         + |         +         |       |         +
V T G F P A S L R L S E E E L L D K L E I F F G K T R N G G G D V D V R E L L P

G S A V I T F V E I G V A D K I L K K E Y P L Y I N Q T C H R V T V S P Y T E 240
| |   + +   |     | | |   + +   + +   + +   +         +   | | |
G S V M L G F A R D G V A Q R L C Q I G Q F T V P L G G Q Q V P L R V S P Y V N

I H L K K Y Q I F S G T S K R T V L L T G M E G I Q M D E E I V E D L I N I H F 280
  + |     + |   |         | + | | +     +   |     | +   +   |
G E I Q K A E I R S Q P V P R S V L V L N I P D I L D G P E L H D V L E I H F Q 288                        307
Q R A K N G G G E V D V V K C S L G Q P H I A Y F E E *  (SEQ ID NO: 1)
+   +   | | |
K P T R G G G G  (SEQ ID NO: 3)
        264

FIG. 2

```
GAATTCCGTGTTTTGTTTGTTCAAGTCTAAGATTTGGAAATGCTGACCCTTTGTTAAGAG    60
CCAACAGGACATATAGGATCCCTTCCCTCCCCCGGCCTGCCTCCGCTGAAGCCACCACCA   120
GCGCCTCCTTGGCTGGATGCTGGAAGAGTCCTCCATGTGTACGGACTCAGGATGACAGGG   180
CAGCCTCCTTCTGTGGTTGCTGGGCTTGTGAACGTTGCAGTATCTTTTGGCTTTCCACGT   240
CTCTAAAATGTTTTTCAACTATTTTGCGTACATGGCTCAGTGCACTCCCCTCTTTGCCTT   300
  1      M  F  F  N  Y  F  A  Y  M  A  Q  C  T  P  L  F  A  F
TACAGTTTTCCACTTGATATGGGGGTGTAATAACAACTTCTTCCATGACTACGATGTTTT   360
 19   T  V  F  H  L  I  W  G  I  C  N  N  N  F  F  H  D  Y  D  V  F
TTTCTTGCCATTTACAGTCTTTAATGGTCTTGTGAATGGTCTGGAAGGGAATTCCATTCC   420
 39   F  L  P  F  T  V  F  N  G  L  V  N  G  L  E  G  N  S  I  P
CAGCCCAAGAAAAGAGTTTAGTGCATGTGCGATTGGCTGCAAAGTGTACATTACTGGGGG   480
 59   S  P  R  K  E  F  S  A  C  A  I  G  C  K  V  Y  I  T  G  G
GCGGGGTGCAGGCTGGAGCCTTCGGGCATGGCGGGCTTTGGGGGGCATTCGCTGGGGGAG   540
 79   R  G  A  G  W  S  L  R  A  W  R  A  L  G  G  I  R  W  G  R
GAGACCCCGTTTGACCCCTGACCTCCGGGCCCTGCTGACGTCAGGAACTTCTGACCCCCG   600
 99   R  P  R  L  T  P  D  L  R  A  L  L  T  S  G  T  S  D  P  R
GGCCCGAGTGACTTATGGGACCCCCAGTCTCTGGGCCCGGTTGTCTGTTGGGGTCACTGA   660
119   A  R  V  T  Y  G  T  P  S  L  W  A  R  L  S  V  G  V  T  E
ACCCCGAGCATGCCTGACGTCTGGGACCCCGGGTCCCCGGGCACAACTGACTGCGGTGAC   720
139      P  R  A  C  L  T  S  G  T  P  G  P  R  A  Q  L  T  A  V  T
CCCAGATACCGGACCCCGGGAGGCCTCAGAGAACTCTGGAACCCGTTCGCGCGCGTGGCT   780
159      P  D  T  R  T  R  E  A  S  E  N  S  G  T  R  S  R  A  W  L
GGCGGTGGCGCTGGGCGCTGGGGGGGCAGTGCTGTTGTTGTTGTGGGGCGGGGGTCGGGG   840
179   A  V  A  L  G  A  G  G  A  V  L  L  L  L  W  G  G  G  R  G
TCCTCCGGCCGTCCTCGCCGCCGTCCCTAGCCCGCCGCCCGCTTCTCCCCGGAGTCAGTA   900
199   P  P  A  V  L  A  A  V  P  S  P  P  P  A  S  P  R  S  Q  Y
CAACTTCATCGCAGATGTGGTGGAGAAGACAGCACCTGCCGTGGTCTATATCGAGATCCT   960
219   N  F  I  A  D  V  V  E  K  T  A  P  A  V  V  Y  I  E  I  L
GGACCGGCACCCTTTCTTGGGCCGCGAGGTCCCTATCTCGAACGGCTCAGGATTCGTGGT  1020
239   D  R  H  P  F  L  G  R  E  V  P  I  S  N  G  S  G  F  V  V
GGCTGCCGATGGGCTCATTGTCACCAACGCCCATGTGGTGGCTGATCGGCGCAGAGTCCG  1080
259   A  A  D  G  L  I  V  T  N  A  H  V  V  A  D  R  R  R  V  R
TGTGAGACTGCTAAGCGGCGACACGTATGAGGCCGTGGTCACAGCTGTGGATCCCGTGGC  1140
279   V  R  L  L  S  G  D  T  Y  E  A  V  V  T  A  V  D  P  V  A
AGACATCGCAACGCTGAGGATTCAGACTAAGGAGCCTCTCCCCACGCTGCCTCTGGGACG  1200
299   D  I  A  T  L  R  I  Q  T  K  E  P  L  P  T  L  P  L  G  R
CTCAGCTGATGTCCGGCAAGGGGAGTTTGTTGTTGCCATGGGAAGTCCCTTTGCACTGCA  1260
319   S  A  D  V  R  Q  G  E  F  V  V  A  M  G  S  P  F  A  L  Q
GAACACGATCACATCCGGCATTGTTAGCTCTGCTCAGCGTCCAGCCAGAGACCTGGGACT  1320
339   N  T  I  T  S  G  I  V  S  S  A  Q  R  P  A  R  D  L  G  L
CCCCCAAACCAATGTGGAATACATTCAAACTGATGCAGCTATTGATTTGGAAACTCTGG  1380
359   P  Q  T  N  V  E  Y  I  Q  T  D  A  A  I  D  F  G  N  S  G
AGGTCCCCTGGTTAACCTGGATGGGGAGGTGATTGGAGTGAACACCATGAAGGTCACAGC  1440
379   G  P  L  V  N  L  D  G  E  V  I  G  V  N  T  M  K  V  T  A
TGGAATCTCCTTTGCCATCCCTTCTGATCGTCTTCGAGAGTTTCTGCATCGTGGGGAAAA  1500
399   G  I  S  F  A  I  P  S  D  R  L  R  E  F  L  H  R  G  E  K
GAAGAATTCCTCCTCCGGAATCAGTGGGTCCCAGCGGCGCTACATTGGGGTGATGATGCT  1560
419   K  N  S  S  S  G  I  S  G  S  Q  R  R  Y  I  G  V  M  M  L
GACCCTGAGTCCCAGCATCCTTGCTGAACTACAGCTTCGAGAACCAAGCTTTCCCGATGT  1620
439   T  L  S  P  S  I  L  A  E  L  Q  L  R  E  P  S  F  P  D  V
TCAGCATGGTGTACTCATCCATAAAGTCATCCTGGGCTCCCCTGCACACCGGGCTGGTCT  1680
459   Q  H  G  V  L  I  H  K  V  I  L  G  S  P  A  H  R  A  G  L
GCGGCCTGGTGATGTGATTTTGGCCATTGGGGAGCAGATGGTACAAAATGCTGAAGATGT  1740
479   R  P  G  D  V  I  L  A  I  G  E  Q  M  V  Q  N  A  E  D  V
TTATGAAGCTGTTCGAACCCAATCCCAGTTGGCAGTGCAGATCCGGCGGGGACGAGAAAC  1800
499   Y  E  A  V  R  T  Q  S  Q  L  A  V  Q  I  R  R  G  R  E  T
ACTGACCTTATATGTGACCCCTGAGGTCACAGAATGAATAGATCACCAAGAGTATGAGGC  1860
519   L  T  L  Y  V  T  P  E  V  T  E  *
TCCTGCTCTGATTTCCTCCTTTCCTTTCTGGCTGAGGTTCTGAGGGCACCGAGACAGAGG  1920
GTTAAATGAACCAGTGGGGGCAGGTCCCTCCAACCACCAGCACTGACTCCTAGGCTTCTG  1980
AACAATCACAGAAACACTTTTTTATATAAAATAAAATTATACCTAGCAAAAAAAAAAAAA  2040
```

FIG. 4A

```
HtrA        ---VMRSVAISINVEGSTTVN-----------------TPRMPRNFQQEFGQ-----DSPFCQEGSPEQS       91
L56    48  -IHRPVIVFQRGACGQG-----------QEDENSLRHKVMEEADVVEGEAPAVHEELRK                191
Omi   142  ALGAGGAVLLLLWGGGRUPPAVLAAVPSPPASPRSQVNEEADVVEKTAPAVVYEEILDR                240
             181

HtrA       SPFCQGGGQQGNGGQOOKFMALGSGVTIDADKGYVVTNNHVVDAATVINVQDSDGRKFDA               151
L56        LPESK-------REVEVASGGSGFTVSED--GLKVMNAHVVTRKHRYVELRNGATVEA                 240
Omi        HPELG-------REVPISNGSGEVVAAD--GELVVTNAHVVADRRRVRRHLSGDTVEA                 289

HtrA       KMVGKDPRSDIALLQIQNPKNLTAIKMADSDALRVGDYTIGIGNPEGIGETVTSGIVSAL               211
L56        KIKDVDEKADIAEEKIDHQGKLPVILGRSSEIRPGEEVVAIGSPFSLQKTVTGISTT                  300
Omi        VVTAVDFVADTATLRIQTKEPETTPLGRSADVRQGEFVVAMGSPFEALQNTIIHSGIVSA  AGISFAI      349

HtrA       GRSG-----TNAEN--YENFIQTDAAINRGNSGGALVNLNGELAGINTAILAPDGGNIGIGFAI           268
L56        DRGGKEIGIRNSDMDYIQTDAIINYGNSGGHIVNLDGEVIGINTLKVT----                AGISFAI 355
Omi        DRPARDIGHPQTNVEKIQTDAAIDFGNSSGGPIVNLDGEVIGVNTMKVT-----              AGISFAI 404

HtrA       PSNMVKNLTSQMVEYGQVKRGELGIMGTELNSELAKAMKVDAQRGAFVSQVLPNSSAAKA               328
L56            ---------DK-----------INKFITESHDR-QAKGKAITKKK-----                      381
Omi            ---------DR-----------IREEIHRGEKKNSSSGISGSQRR-----                      431

HtrA       GIKAGDVITSLNGKPISSFAALRAQVGTMPVGSKLTLGLLRDGKQVNVNLEEQQSSQNQV               388
L56         --------------------VIGIRMSLTSSKAKEIKDR-----                              401
Omi         --------------------VIGVMLTTSPSILAEIQLR-----                              451

HtrA       DSSSIFNGIEGAEMSNKGKDQGVVNNKTGTPAAQIGLKKGDVIIGANQQAVKNIAELR                 448
L56         -----------HRDFPDYISQAYIIEVIPDTPAEAGGLKENDVIISDGSVVSANDVS                 449
Omi         -----------EPSEPDVQHGVLIHKVILGSPAHRAGIRPGDVILAIGEQMVQNAEDVY               499

HtrA       KVLDSKPSVIALNIQRGDRHLPVNAVTSLNFLKTGRSPYNL                                  491
L56        DVIKRE-STNMVRRGN-----EDIMTTVIPEEIDP-----                                   480
Omi        EAVRTQ-SQHAVQIRRGR----ETLTLYTEEVTE-----                                    529
```

FIG. 5A

```
       -298 CGCACCATACCGGCGCGGGCACCTGGGGAGAAATGGATGGAGAAGGGACCTGGCTGGAAAG
     CTTTGCCCCGCTGCTCTGCTCCGCCCATAAGAGGACCCCTGAAATGTCCCGTGCAGTTTGTTCAAGTCCCCTGTGTGAT
     GAAATGTGCCTCTCGCCTTACCCGTGTGAGAATACCCTGTGGTGTGGCAGCGAGTATTTTGGTATTTGACCTGTCCAAAG
     ACGACTTGATACCTCTATAATGTAACAGAAAAGGTCAGAAAATATTAAGCAAGTAGAAGTGTGGAGCATATTAAGCAAG
     ATG AAC ATC TCG GGA AGC AGC TGT GGA AGC CCT AAC TCT GCA GAT ACA TCT AGT GAC TTT   60
  1   M   N   I   S   G   S   S   C   G   S   P   N   S   A   D   T   S   S   D   F
     AAG GAC CTT TGG ACA AAA CTA AAA GAA TGT CAT GAT AGA GAA GTA CAA GGT TTA CAA GTA  120
 21   K   D   L   W   T   K   L   K   E   C   H   D   R   E   V   Q   G   L   Q   V
     AAA GTA ACC AAG CTA AAA CAG GAA CGA ATC TTA GAT GCA CAA AGA CTA GAA GAA TTC TTC  180
 41   K   V   T   K   L   K   Q   E   R   I   L   D   A   Q   R   L   E   E   F   F
     ACC AAA AAT CAA CAG CTG AGG GAA CAG CAG AAA GTC CTT CAT GAA ACC ATT AAA GTT TTA  240
 61   T   K   N   Q   Q   L   R   E   Q   Q   K   V   L   H   E   T   I   K   V   L
     GAA GAT CGG TTA AGA GCA GGC TTA TGT GAT CGC TGT GCA GTA ACT GAA GAA CAT ATG CGG  300
 81   E   D   R   L   R   A   G   L   C   D   R   C   A   V   T   E   E   H   M   R
     AAA AAA CAG CAA GAG TTT GAA AAT ATC CGG CAG CAG AAT CTT AAA CTT ATT ACA GAA CTT  360
101   K   K   Q   Q   E   F   E   N   I   R   Q   Q   N   L   K   L   I   T   E   L
     ATG AAT GAA AGG AAT ACT CTA CAG GAA GAA AAT AAA AAG CTT TCT GAA CAA CTC CAG CAG  420
121   M   N   E   R   N   T   L   Q   E   E   N   K   K   L   S   E   Q   L   Q   Q
     AAA ATT GAG AAT GAT CAA CAG CAT CAA GCA GCT GAG GTT GAA TGT GAG GAA GAC GTT ATT  480
141   K   I   E   N   D   Q   Q   H   Q   A   A   E   L   E   C   E   E   D   V   I
     CCA GAT TCA CCG ATA ACA GCC TTC TCA TTT TCT GGC GTT AAC CGG CTA CGA AGA AAG GAG  540
161   P   D   S   P   I   T   A   F   S   F   S   G   V   N   R   L   R   R   K   E
     AAC CCC CAT GTC CGA TAC ATA GAA CAA ACA CAT ACT AAA TTG GAG CAC TCT GTG TGT GCA  600
181   N   P   H   V   R   Y   I   E   Q   T   H   T   K   L   E   H   S   V   C   A
     AAT GAA ATG AGA AAA GTT TCC AAG TCT TCA ACT CAT CCA CAA CAT AAT CCT AAT GAA AAT  660
201   N   E   M   R   K   V   S   K   S   S   T   H   P   Q   H   N   P   N   E   N
     GAA ATT CTA GTA GCT GAC ACT TAT GAC CAA AGT CAA TCT CCA ATG GCC AAA GCA CAT GGA  720
221   E   I   L   V   A   D   T   Y   D   Q   S   Q   S   P   M   A   K   A   H   G
     ACA AGC AGC TAT ACC CCT GAT AAG TCA TCT TTT AAT TTA GCT ACA GTT GTT GCT GAA ACA  780
241   T   S   S   Y   T   P   D   K   S   S   F   N   L   A   T   V   V   A   E   T
     CTT GGA CTT GGT GTT CAA GAA GAA TCT GAA ACT CAA GGT CCC ATG AGC CCC CTT GGT GAT  840
261   L   G   L   G   V   Q   E   E   S   E   T   Q   G   P   M   S   P   L   G   D
     GAG CTC TAC CAC TGT CTG GAA GGA AAT CAC AAG AAA CAG CCT TTT GAG GAA TCT ACA AGA  900
281   E   L   Y   H   C   L   E   G   N   H   K   K   Q   P   F   E   E   S   T   R
     AAT ACT GAA GAT AGT TTA AGA TTT TCA GAT TCT ACT TCA AAG ACT CCT CCT CAA GAA GAA  960
301   N   T   E   D   S   L   R   F   S   D   S   T   S   K   T   P   P   Q   E   E
     TTA CCT ACT CGA GTG TCA TCT CCT GTA TTT GGA GCT ACC TCT AGT ATC AAA AGT GGT TTA 1020
321   L   P   T   R   V   S   S   P   V   F   G   A   T   S   S   I   K   S   G   L
     GAT TTG AAT ACA AGT TTG TCC CCT TCT CTT TTA CAG CCT GGG AAA AAA AAA CAT CTG AAA 1080
341   D   L   N   T   S   L   S   P   S   L   L   Q   P   G   K   K   K   H   L   K
     ACA CTC CCT TTT AGC AAC ACT TGT ATA TCT AGA TTA GAA AAA ACT AGA TCA AAA TCT GAA 1140
361   T   L   P   F   S   N   T   C   I   S   R   L   E   K   T   R   S   K   S   E
     GAT AGT GCC CTT TTC ACA CAT CAC AGT CTT GGG TCT GAA GTG AAC AAG ATC ATT ATC CAG 1200
381   D   S   A   L   F   T   H   H   S   L   G   S   E   V   N   K   I   I   I   Q
     TCA TCT AAT AAA CAG ATA CTT ATA AAT AAA AAT ATA AGT GAA TCC CTA GGT GAA CAG AAT 1260
401   S   S   N   K   Q   I   L   I   N   K   N   I   S   E   S   L   G   E   Q   N
```

FIG. 7A

```
       AGG ACT GAG TAC GGT AAA GAT TCT AAC ACT GAT AAA CAT TTG GAG CCC CTG AAA TCA TTG  1320
421     R   T   E   Y   G   K   D   S   N   T   D   K   H   L   E   P   L   K   S   L
       GGA GGC CGA ACA TCC AAA AGG AAG AAA ACT GAG GAA GAA AGT GAA CAT GAA GTA AGC TGC  1380
441     G   G   R   T   S   K   R   K   K   T   E   E   E   S   E   H   E   V   S   C
       CCC CAA GCT TCT TTT GAT AAA GAA AAT GCT TTC CCT TTT CCA ATG GAT AAT CAG TTT TCC  1440
461     P   Q   A   S   F   D   K   E   N   A   F   P   F   P   M   D   N   Q   F   S
       ATG AAT GGA GAC TGT GTG ATG GAT AAA CCT CTG GAT CTG TCT GAT CGA TTT TCA GCT ATT  1500
481     M   N   G   D   C   V   M   D   K   P   L   D   L   S   D   R   F   S   A   I
       CAG CGT CAA GAG AAA AGC CAA GGA AGT GAG ACT TCT AAA AAC AAA TTT AGG CAA GTG ACT  1560
501     Q   R   Q   E   K   S   Q   G   S   E   T   S   K   N   K   F   R   Q   V   T
       CTT TAT GAG GCT TTG AAG ACC ATT CCA AAG GGC TTT TCC TCA AGC CGT AAG GCC TCA GAT  1620
521     L   Y   E   A   L   K   T   I   P   K   G   F   S   S   S   R   K   A   S   D
       GGC AAC TGC ACG TTG CCC AAA GAT TCC CCA GGG GAG CCC TGT TCA CAG GAA TGC ATC ATC  1680
541     G   N   C   T   L   P   K   D   S   P   G   E   P   C   S   Q   E   C   I   I
       CTT CAG CCC TTG AAT AAA TGC TCT CCA GAC AAT AAA CCA TCA TTA CAA ATA AAA GAA GAA  1740
561     L   Q   P   L   N   K   C   S   P   D   N   K   P   S   L   Q   I   K   E   E
       AAT GCT GTC TTT AAA ATT CCT CTA CGT CCA CGT GAA AGT TTG GAG ACT GAG AAT GTT TTA  1800
581     N   A   V   F   K   I   P   L   R   P   R   E   S   L   E   T   E   N   V   L
       GAT GAC ATA AAG AGT GCT GGT TCT CAT GAG CCA ATA AAA ATA CAA ACC AGG TCA GAC CAT  1860
601     D   D   I   K   S   A   G   S   H   E   P   I   K   I   Q   T   R   S   D   H
       GGA GGA TGT GAA CTT GCA TCA GTT CTT CAG TTA AAT CCA TGT AGA ACT GGT AAA ATA AAG  1920
621     G   G   C   E   L   A   S   V   L   Q   L   N   P   C   R   T   G   K   I   K
       TCT CTA CAA AAC AAC GAT GTA TCC TTT GAA AAT ATC CAG TGG AGT ATA GAT CCG GGA       1980
641     S   L   Q   N   N   Q   D   V   S   F   E   N   I   Q   W   S   I   D   P   G
       GCA GAC CTT TCT CAG TAT AAA ATG GAT GTT ACT GTA ATA GAT ACA AAG GAT GGC AGT CAG  2040
661     A   D   L   S   Q   Y   K   M   D   V   T   V   I   D   T   K   D   G   S   Q
       TCA AAA TTA GGA GGA GAG ACA GTG GAC ATG GAC TGT ACA TTG GTT AGT GAA ACC GTT CTC  2100
681     S   K   L   G   G   E   T   V   D   M   D   C   T   L   V   S   E   T   V   L
       TTA AAA ATG AAG AAG CAA GAG CAG AAG GGA GAA AAA AGT TCA AAT GAA GAA AGA AAA ATG  2160
701     L   K   M   K   K   Q   E   Q   K   G   E   K   S   S   N   E   E   R   K   M
       AAT GAT AGC TTG GAA GAT ATG TTT GAT CGG ACA ACA CAT GAA GAG TAT GAA TCC TGT TTG  2220
721     N   D   S   L   E   D   M   F   D   R   T   T   H   E   E   Y   E   S   C   L
       GCA GAC AGT TTC TCC CAA GCA GCA GAT GAA GAG GAG GAA TTG TCT ACT GCC ACA AAG AAA  2280
741     A   D   S   F   S   Q   A   A   D   E   E   E   E   L   S   T   A   T   K   K
       CTA CAC ACT CAT GGT GAT AAA CAA GAC AAA GTC AAG CAG AAA GCG TTT GTG GAG CCG TAT  2340
761     L   H   T   H   G   D   K   Q   D   K   V   K   Q   K   A   F   V   E   P   Y
       TTT AAA GGT GAT GAA AGA GAG ACT AGC TTG CAA AAT TTT CCT CAT ATT GAG GTG GTT CGG  2400
781     F   K   G   D   E   R   E   T   S   L   Q   N   F   P   H   I   E   V   V   R
       AAA AAA GAG GAG AGA AGA AAA CTG CTT GGG CAC ACG TGT AAG GAA TGT GAA ATT TAT TAT  2460
801     K   K   E   E   R   R   K   L   L   G   H   T   C   K   E   C   E   I   Y   Y
       GCA GAT ATG CCA GCA GAA GAA AGA GAA AAG AAA TTG GCT TCC TGC TCA AGA CAC CGA TTC  2520
821     A   D   M   P   A   E   E   R   E   K   K   L   A   S   C   S   R   H   R   F
       CGC TAC ATT CCA CCC AAC ACA CCA GAG AAT TTT TGG GAA GTT GGT TTT CCT TCC ACT CAG  2580
841     R   Y   I   P   P   N   T   P   E   N   F   W   E   V   G   F   P   S   T   Q
       ACT TGT ATG GAA AGA GGT TAT ATT AAG GAA GAT CTT GAT CCT TGT CCT CGT CCA AAA AGA  2640
861     T   C   M   E   R   G   Y   I   K   E   D   L   D   P   C   P   R   P   K   R
       CGT CAG CCT TAC AAC GCA ATA TTT TCT CCA AAA GGC AAG GAG CAG AAG ACA TAG ACG TTG  2700
881     R   Q   P   Y   N   A   I   F   S   P   K   G   K   E   Q   K   T*  *
       AAACAGAAACAGAAGGATGAAGGACAGTTTTTTTCCTTCTTAGTTATTTATAGTTAAAGTTGGTACTAAACATTGATTTT
       TTTGATCTTCTGTAAATGGATTTATAAATCAGTTTTCTATTGAAAATGTTTGTGATATTTTGCTTTTGCACCTTTAAAA
       CAATAAGGCGCTTTCATTTTGCACTCTAACTTAAGAGTTTTTACTTTATGTAGTGATACCTAATACAATTTTGAAAATA
       CAAAAAAAAA 2948
```

FIG. 7B

SEQUENCE LISTING

```
<160> NUMBER OF SEQ ID NOS: 16

<210> SEQ ID NO 1
<211> LENGTH: 1426
<212> TYPE: DNA
<213> ORGANISM: Homo sapiens
<220> FEATURE:
<221> NAME/KEY: CDS
<222> LOCATION: (281)...(1201)

<400> SEQUENCE: 1
ggatccgcgt gctaaagaaa aatcgccgtt aaagcagttt tcttttcac tgtcttttc      60 ttttcgcggg gaacccagct gttcctgcga gggccacctc ctcaggaaga ccccgcagct   120
ctcccgcggc gcttctgcag gaggcagcga cagtttcgag aacccgggcc ttcccctccc   180
agtgcctccg ggggttcgcg tttcaggcgc tcgtgttttc cgggaagggc aggcgcgctg   240
ggccttgggg agctgcgctc ggcgggcgga ccggggatc atg gaa gct gat aaa      295
                                            Met Glu Ala Asp Lys
                                              1               5
```

-continued

| | |
|---|---|
| gat gac aca caa caa att ctt aag gag cat tcg cca gat gaa ttt ata<br>Asp Asp Thr Gln Gln Ile Leu Lys Glu His Ser Pro Asp Glu Phe Ile<br>              10                    15                  20 | 343 |
| aaa gat gaa caa aat aag gga cta att gat gaa att aca aag aaa aat<br>Lys Asp Glu Gln Asn Lys Gly Leu Ile Asp Glu Ile Thr Lys Lys Asn<br>              25                    30                  35 | 391 |
| att cag cta aag aag gag atc caa aag ctt gaa acg gag tta caa gag<br>Ile Gln Leu Lys Lys Glu Ile Gln Lys Leu Glu Thr Glu Leu Gln Glu<br>        40                    45                  50 | 439 |
| gct acc aaa gaa ttc cag att aaa gag gat att cct gaa aca aag atg<br>Ala Thr Lys Glu Phe Gln Ile Lys Glu Asp Ile Pro Glu Thr Lys Met<br>55                    60                  65 | 487 |
| aaa ttc tta tca gtt gaa act cct gag aat gac agc cag ttg tca aat<br>Lys Phe Leu Ser Val Glu Thr Pro Glu Asn Asp Ser Gln Leu Ser Asn<br>70                    75                  80                  85 | 535 |
| atc tcc tgt tcg ttt caa gtg agc tcg aaa gtt cct tat gag ata caa<br>Ile Ser Cys Ser Phe Gln Val Ser Ser Lys Val Pro Tyr Glu Ile Gln<br>              90                    95                  100 | 583 |
| aaa gga caa gca ctt atc acc ttt gaa aaa gaa gaa gtt gct caa aat<br>Lys Gly Gln Ala Leu Ile Thr Phe Glu Lys Glu Glu Val Ala Gln Asn<br>        105                    110                  115 | 631 |
| gtg gta agc atg agt aaa cat cat gta cag ata aaa gat gta aat ctg<br>Val Val Ser Met Ser Lys His His Val Gln Ile Lys Asp Val Asn Leu<br>              120                    125                  130 | 679 |
| gag gtt acg gcc aag cca gtt cca tta aat tca gga gtc aga ttc cag<br>Glu Val Thr Ala Lys Pro Val Pro Leu Asn Ser Gly Val Arg Phe Gln<br>135                    140                  145 | 727 |
| gtt tat gta gaa gtt tct aaa atg aaa atc aat gtt act gaa att cct<br>Val Tyr Val Glu Val Ser Lys Met Lys Ile Asn Val Thr Glu Ile Pro<br>150                    155                  160                  165 | 775 |
| gac aca ctg cgt gaa gat caa atg aga gac aaa cta gag ctg agc ttt<br>Asp Thr Leu Arg Glu Asp Gln Met Arg Asp Lys Leu Glu Leu Ser Phe<br>        170                    175                  180 | 823 |
| tca aag ttc cga aat gga ggc gga gag gtg gac cgc gtg gac tat gac<br>Ser Lys Phe Arg Asn Gly Gly Gly Glu Val Asp Arg Val Asp Tyr Asp<br>              185                    190                  195 | 871 |
| aga cag tcc ggg agt gca gtc atc acg ttt gtg gag att gga gtg gct<br>Arg Gln Ser Gly Ser Ala Val Ile Thr Phe Val Glu Ile Gly Val Ala<br>        200                    205                  210 | 919 |
| gac aag att ttg aaa aag aaa gaa tac cct ctt tat ata aat caa acc<br>Asp Lys Ile Leu Lys Lys Lys Glu Tyr Pro Leu Tyr Ile Asn Gln Thr<br>215                    220                  225 | 967 |
| tgc cat aga gtt act gtt tct cca tac aca gaa ata cac ttg aaa aag<br>Cys His Arg Val Thr Val Ser Pro Tyr Thr Glu Ile His Leu Lys Lys<br>230                    235                  240                  245 | 1015 |
| tat cag ata ttt tca gga aca tct aag agg aca gtg ctt ctg aca gga<br>Tyr Gln Ile Phe Ser Gly Thr Ser Lys Arg Thr Val Leu Leu Thr Gly<br>        250                    255                  260 | 1063 |
| atg gaa ggc att caa atg gat gaa gaa att gtg gag gat tta att aac<br>Met Glu Gly Ile Gln Met Asp Glu Glu Ile Val Glu Asp Leu Ile Asn<br>              265                    270                  275 | 1111 |
| att cac ttt caa cgg gca aag aat gga ggt gga gaa gta gat gtg gtc<br>Ile His Phe Gln Arg Ala Lys Asn Gly Gly Gly Glu Val Asp Val Val<br>        280                    285                  290 | 1159 |
| aag tgt tct cta ggt caa cct cac ata gca tac ttt gaa gaa<br>Lys Cys Ser Leu Gly Gln Pro His Ile Ala Tyr Phe Glu Glu<br>295                    300                  305 | 1201 |
| tagacttaac agaatcatga aaactatagc tttttaaccc ggattactgt aaatgtttga | 1261 |
| caagaatgaa tatgcttttc cttaaaaaat gaaaacttta atttttacca tccatttatg | 1321 |

```
tttagataca aaacttattt ccatgttttct gaatcttctt tgtttcaaat ggtgctgcat   1381
gttttcaact acaataagtg cactgtaata aaaagttttg tttat                    1426
```

<210> SEQ ID NO 2
<211> LENGTH: 85
<212> TYPE: PRT
<213> ORGANISM: Homo sapiens

<400> SEQUENCE: 2

```
Gln Ala Phe Glu Asn Glu Lys Glu Gln Glu Arg Glu Glu Gln Leu Ala
  1               5                  10                  15

Lys Ala Met Glu Lys Leu Asn Ser Glu Gln Asn Ile Leu Asp Glu Val
             20                  25                  30

Thr Lys Lys Leu Glu Gln Ser Glu Glu Val Leu Ala Ala Arg Gly
         35                  40                  45

Ala Ile Gln Glu Leu Thr Glu Lys Leu Glu Glu Ser Glu Lys Glu Thr
     50                  55                  60

Ser Thr Ala Lys Thr Glu Leu Glu Ala Val Ser Lys Lys Leu Asp Ser
 65                  70                  75                  80

Ser Glu Thr Ser Leu
             85
```

<210> SEQ ID NO 3
<211> LENGTH: 186
<212> TYPE: PRT
<213> ORGANISM: Homo sapiens

<400> SEQUENCE: 3

```
Gly Ser Ala Leu Ile Thr Phe Asp Asp Pro Lys Val Ala Glu Gln Val
  1               5                  10                  15

Leu Gln Gln Lys Glu His Thr Ile Asn Met Glu Glu Cys Arg Leu Arg
             20                  25                  30

Val Gln Val Gln Pro Leu Glu Leu Pro Met Val Thr Thr Ile Gln Val
         35                  40                  45

Ser Ser Gln Leu Ser Gly Arg Arg Val Leu Val Thr Gly Phe Pro Ala
     50                  55                  60

Ser Leu Arg Leu Ser Glu Glu Leu Leu Asp Lys Leu Glu Ile Phe
 65                  70                  75                  80

Phe Gly Lys Thr Arg Asn Gly Gly Gly Asp Val Asp Val Arg Glu Leu
             85                  90                  95

Leu Pro Gly Ser Val Met Leu Gly Phe Ala Arg Asp Gly Val Ala Gln
            100                 105                 110

Arg Leu Cys Gln Ile Gly Gln Phe Thr Val Pro Leu Gly Gly Gln Gln
            115                 120                 125

Val Pro Leu Arg Val Ser Pro Tyr Val Asn Gly Glu Ile Gln Lys Ala
        130                 135                 140

Glu Ile Arg Ser Gln Pro Val Pro Arg Ser Val Leu Val Leu Asn Ile
145                 150                 155                 160

Pro Asp Ile Leu Asp Gly Pro Glu Leu His Asp Val Leu Glu Ile His
                165                 170                 175

Phe Glu Lys Pro Thr Arg Gly Gly Gly
            180                 185
```

<210> SEQ ID NO 4
<211> LENGTH: 2040
<212> TYPE: DNA

```
<213> ORGANISM: Homo sapiens
<220> FEATURE:
<221> NAME/KEY: CDS
<222> LOCATION: (248)...(1834)

<400> SEQUENCE: 4
gaattccgtg ttttgtttgt tcaagtctaa gatttggaaa tgctgaccct ttgttaagag      60
ccaacaggac ataggatcc cttccctcc cccggcctgc ctccgctgaa gccaccacca      120
gcgcctcctt ggctggatgc tggaagagtc ctccatgtgt acggactcag gatgacaggg      180
cagcctcctt ctgtggttgc tgggcttgtg aacgttgcag tatcttttgg cttttccacgt      240
```

| | | | | | | | | | | | | | | |
|---|---|---|---|---|---|---|---|---|---|---|---|---|---|---|
| ctctaaa | atg | ttt | ttc | aac | tat | ttt | gcg | tac | atg | gct | cag | tgc | act | ccc | 289 |
| | Met | Phe | Phe | Asn | Tyr | Phe | Ala | Tyr | Met | Ala | Gln | Cys | Thr | Pro | |
| | 1 | | | | 5 | | | | | 10 | | | | | |

| ctc | ttt | gcc | ttt | aca | gtt | ttc | cac | ttg | ata | tgg | ggg | tgt | aat | aac | aac | 337 |
|---|---|---|---|---|---|---|---|---|---|---|---|---|---|---|---|---|
| Leu | Phe | Ala | Phe | Thr | Val | Phe | His | Leu | Ile | Trp | Gly | Cys | Asn | Asn | Asn | |
| 15 | | | | | 20 | | | | | 25 | | | | | 30 | |

| ttc | ttc | cat | gac | tac | gat | gtt | ttt | ttc | ttg | cca | ttt | aca | gtc | ttt | aat | 385 |
|---|---|---|---|---|---|---|---|---|---|---|---|---|---|---|---|---|
| Phe | Phe | His | Asp | Tyr | Asp | Val | Phe | Phe | Leu | Pro | Phe | Thr | Val | Phe | Asn | |
| | | | | 35 | | | | | 40 | | | | | 45 | | |

| ggt | ctt | gtg | aat | ggt | ctg | gaa | ggg | aat | tcc | att | ccc | agc | cca | aga | aaa | 433 |
|---|---|---|---|---|---|---|---|---|---|---|---|---|---|---|---|---|
| Gly | Leu | Val | Asn | Gly | Leu | Glu | Gly | Asn | Ser | Ile | Pro | Ser | Pro | Arg | Lys | |
| | 50 | | | | | 55 | | | | | 60 | | | | | |

| gag | ttt | agt | gca | tgt | gcg | att | ggc | tgc | aaa | gtg | tac | att | act | ggg | ggg | 481 |
|---|---|---|---|---|---|---|---|---|---|---|---|---|---|---|---|---|
| Glu | Phe | Ser | Ala | Cys | Ala | Ile | Gly | Cys | Lys | Val | Tyr | Ile | Thr | Gly | Gly | |
| 65 | | | | | 70 | | | | | 75 | | | | | | |

| cgg | ggt | gca | ggc | tgg | agc | ctt | cgg | gca | tgg | cgg | gct | ttg | ggg | ggc | att | 529 |
|---|---|---|---|---|---|---|---|---|---|---|---|---|---|---|---|---|
| Arg | Gly | Ala | Gly | Trp | Ser | Leu | Arg | Ala | Trp | Arg | Ala | Leu | Gly | Gly | Ile | |
| | 80 | | | | 85 | | | | | 90 | | | | | | |

| cgc | tgg | ggg | agg | aga | ccc | cgt | ttg | acc | cct | gac | ctc | cgg | gcc | ctg | ctg | 577 |
|---|---|---|---|---|---|---|---|---|---|---|---|---|---|---|---|---|
| Arg | Trp | Gly | Arg | Arg | Pro | Arg | Leu | Thr | Pro | Asp | Leu | Arg | Ala | Leu | Leu | |
| 95 | | | | | 100 | | | | | 105 | | | | | 110 | |

| acg | tca | gga | act | tct | gac | ccc | cgg | gcc | cga | gtg | act | tat | ggg | acc | ccc | 625 |
|---|---|---|---|---|---|---|---|---|---|---|---|---|---|---|---|---|
| Thr | Ser | Gly | Thr | Ser | Asp | Pro | Arg | Ala | Arg | Val | Thr | Tyr | Gly | Thr | Pro | |
| | | | | 115 | | | | | 120 | | | | | 125 | | |

| agt | ctc | tgg | gcc | cgg | ttg | tct | gtt | ggg | gtc | act | gaa | ccc | cga | gca | tgc | 673 |
|---|---|---|---|---|---|---|---|---|---|---|---|---|---|---|---|---|
| Ser | Leu | Trp | Ala | Arg | Leu | Ser | Val | Gly | Val | Thr | Glu | Pro | Arg | Ala | Cys | |
| | | | 130 | | | | | 135 | | | | | 140 | | | |

| ctg | acg | tct | ggg | acc | ccg | ggt | ccc | cgg | gca | caa | ctg | act | gcg | gtg | acc | 721 |
|---|---|---|---|---|---|---|---|---|---|---|---|---|---|---|---|---|
| Leu | Thr | Ser | Gly | Thr | Pro | Gly | Pro | Arg | Ala | Gln | Leu | Thr | Ala | Val | Thr | |
| | | 145 | | | | | 150 | | | | | 155 | | | | |

| cca | gat | acc | agg | acc | cgg | gag | gcc | tca | gag | aac | tct | gga | acc | cgt | tcg | 769 |
|---|---|---|---|---|---|---|---|---|---|---|---|---|---|---|---|---|
| Pro | Asp | Thr | Arg | Thr | Arg | Glu | Ala | Ser | Glu | Asn | Ser | Gly | Thr | Arg | Ser | |
| 160 | | | | | 165 | | | | | 170 | | | | | | |

| cgc | gcg | tgg | ctg | gcg | gtg | gcg | ctg | ggc | gct | ggg | ggg | gca | gtg | ctg | ttg | 817 |
|---|---|---|---|---|---|---|---|---|---|---|---|---|---|---|---|---|
| Arg | Ala | Trp | Leu | Ala | Val | Ala | Leu | Gly | Ala | Gly | Gly | Ala | Val | Leu | Leu | |
| 175 | | | | | 180 | | | | | 185 | | | | | 190 | |

| ttg | ttg | tgg | ggc | ggg | ggt | cgg | ggt | cct | ccg | gcc | gtc | ctc | gcc | gcc | gtc | 865 |
|---|---|---|---|---|---|---|---|---|---|---|---|---|---|---|---|---|
| Leu | Leu | Trp | Gly | Gly | Gly | Arg | Gly | Pro | Pro | Ala | Val | Leu | Ala | Ala | Val | |
| | | | | 195 | | | | | 200 | | | | | 205 | | |

| cct | agc | ccg | ccg | ccc | gct | tct | ccc | cgg | agt | cag | tac | aac | ttc | atc | gca | 913 |
|---|---|---|---|---|---|---|---|---|---|---|---|---|---|---|---|---|
| Pro | Ser | Pro | Pro | Pro | Ala | Ser | Pro | Arg | Ser | Gln | Tyr | Asn | Phe | Ile | Ala | |
| | | | 210 | | | | | 215 | | | | | 220 | | | |

| gat | gtg | gtg | gag | aag | aca | gca | cct | gcc | gtg | gtc | tat | atc | gag | atc | ctg | 961 |
|---|---|---|---|---|---|---|---|---|---|---|---|---|---|---|---|---|
| Asp | Val | Val | Glu | Lys | Thr | Ala | Pro | Ala | Val | Val | Tyr | Ile | Glu | Ile | Leu | |
| | | 225 | | | | | 230 | | | | | 235 | | | | |

| gac | cgg | cac | cct | ttc | ttg | ggc | cgc | gag | gtc | cct | atc | tcg | aac | ggc | tca | 1009 |
|---|---|---|---|---|---|---|---|---|---|---|---|---|---|---|---|---|
| Asp | Arg | His | Pro | Phe | Leu | Gly | Arg | Glu | Val | Pro | Ile | Ser | Asn | Gly | Ser | |
| | 240 | | | | | 245 | | | | | 250 | | | | | |

```
gga ttc gtg gtg gct gcc gat ggg ctc att gtc acc aac gcc cat gtg      1057
Gly Phe Val Val Ala Ala Asp Gly Leu Ile Val Thr Asn Ala His Val
255                 260                 265                 270 gtg gct gat cgg cgc aga gtc cgt gtg aga ctg cta agc ggc gac acg      1105
Val Ala Asp Arg Arg Arg Val Arg Val Arg Leu Leu Ser Gly Asp Thr
            275                 280                 285 tat gag gcc gtg gtc aca gct gtg gat ccc gtg gca gac atc gca acg      1153
Tyr Glu Ala Val Val Thr Ala Val Asp Pro Val Ala Asp Ile Ala Thr
        290                 295                 300 ctg agg att cag act aag gag cct ctc ccc acg ctg cct ctg gga cgc      1201
Leu Arg Ile Gln Thr Lys Glu Pro Leu Pro Thr Leu Pro Leu Gly Arg
    305                 310                 315 tca gct gat gtc cgg caa ggg gag ttt gtt gtt gcc atg gga agt ccc      1249
Ser Ala Asp Val Arg Gln Gly Glu Phe Val Val Ala Met Gly Ser Pro
320                 325                 330 ttt gca ctg cag aac acg atc aca tcc ggc att gtt agc tct gct cag      1297
Phe Ala Leu Gln Asn Thr Ile Thr Ser Gly Ile Val Ser Ser Ala Gln
335                 340                 345                 350 cgt cca gcc aga gac ctg gga ctc ccc caa acc aat gtg gaa tac att      1345
Arg Pro Ala Arg Asp Leu Gly Leu Pro Gln Thr Asn Val Glu Tyr Ile
            355                 360                 365 caa act gat gca gct att gat ttt gga aac tct gga ggt ccc ctg gtt      1393
Gln Thr Asp Ala Ala Ile Asp Phe Gly Asn Ser Gly Gly Pro Leu Val
        370                 375                 380 aac ctg gat ggg gag gtg att gga gtg aac acc atg aag gtc aca gct      1441
Asn Leu Asp Gly Glu Val Ile Gly Val Asn Thr Met Lys Val Thr Ala
    385                 390                 395 gga atc tcc ttt gcc atc cct tct gat cgt ctt cga gag ttt ctg cat      1489
Gly Ile Ser Phe Ala Ile Pro Ser Asp Arg Leu Arg Glu Phe Leu His
400                 405                 410 cgt ggg gaa aag aag aat tcc tcc tcc gga atc agt ggg tcc cag cgg      1537
Arg Gly Glu Lys Lys Asn Ser Ser Ser Gly Ile Ser Gly Ser Gln Arg
415                 420                 425                 430 cgc tac att ggg gtg atg atg ctg acc ctg agt ccc agc atc ctt gct      1585
Arg Tyr Ile Gly Val Met Met Leu Thr Leu Ser Pro Ser Ile Leu Ala
            435                 440                 445 gaa cta cag ctt cga gaa cca agc ttt ccc gat gtt cag cat ggt gta      1633
Glu Leu Gln Leu Arg Glu Pro Ser Phe Pro Asp Val Gln His Gly Val
        450                 455                 460 ctc atc cat aaa gtc atc ctg ggc tcc cct gca cac cgg gct ggt ctg      1681
Leu Ile His Lys Val Ile Leu Gly Ser Pro Ala His Arg Ala Gly Leu
    465                 470                 475 cgg cct ggt gat gtg att ttg gcc att ggg gag cag atg gta caa aat      1729
Arg Pro Gly Asp Val Ile Leu Ala Ile Gly Glu Gln Met Val Gln Asn
480                 485                 490 gct gaa gat gtt tat gaa gct gtt cga acc caa tcc cag ttg gca gtg      1777
Ala Glu Asp Val Tyr Glu Ala Val Arg Thr Gln Ser Gln Leu Ala Val
495                 500                 505                 510 cag atc cgg cgg gga cga gaa aca ctg acc tta tat gtg acc cct gag      1825
Gln Ile Arg Arg Gly Arg Glu Thr Leu Thr Leu Tyr Val Thr Pro Glu
            515                 520                 525 gtc aca gaa tgaatagatc accaagagta tgaggctcct gctctgattt              1874
Val Thr Glu cctcctttcc tttctggctg aggttctgag ggcaccgaga cagagggtta aatgaaccag    1934
tgggggcagg tccctccaac caccagcact gactcctagg cttctgaaca atcacagaaa    1994 cacttttttat ataaaataaa attataccta gcaaaaaaaa aaaaaa                  2040

<210> SEQ ID NO 5
```

```
<211> LENGTH: 529
<212> TYPE: PRT
<213> ORGANISM: Homo sapiens

<400> SEQUENCE: 5

Met Phe Phe Asn Tyr Phe Ala Tyr Met Ala Gln Cys Thr Pro Leu Phe
 1               5                  10                  15

Ala Phe Thr Val Phe His Leu Ile Trp Gly Cys Asn Asn Asn Phe Phe
             20                  25                  30

His Asp Tyr Asp Val Phe Phe Leu Pro Phe Thr Val Phe Asn Gly Leu
         35                  40                  45

Val Asn Gly Leu Glu Gly Asn Ser Ile Pro Ser Pro Arg Lys Glu Phe
     50                  55                  60

Ser Ala Cys Ala Ile Gly Cys Lys Val Tyr Ile Thr Gly Gly Arg Gly
 65                  70                  75                  80

Ala Gly Trp Ser Leu Arg Ala Trp Arg Ala Leu Gly Gly Ile Arg Trp
                 85                  90                  95

Gly Arg Arg Pro Arg Leu Thr Pro Asp Leu Arg Ala Leu Leu Thr Ser
             100                 105                 110

Gly Thr Ser Asp Pro Arg Ala Arg Val Thr Tyr Gly Thr Pro Ser Leu
         115                 120                 125

Trp Ala Arg Leu Ser Val Gly Val Thr Glu Pro Arg Ala Cys Leu Thr
     130                 135                 140

Ser Gly Thr Pro Gly Pro Arg Ala Gln Leu Thr Ala Val Thr Pro Asp
145                 150                 155                 160

Thr Arg Thr Arg Glu Ala Ser Glu Asn Ser Gly Thr Arg Ser Arg Ala
                 165                 170                 175

Trp Leu Ala Val Ala Leu Gly Ala Gly Ala Val Leu Leu Leu Leu
             180                 185                 190

Trp Gly Gly Gly Arg Gly Pro Pro Ala Val Leu Ala Ala Val Pro Ser
     195                 200                 205

Pro Pro Pro Ala Ser Pro Arg Ser Gln Tyr Asn Phe Ile Ala Asp Val
     210                 215                 220

Val Glu Lys Thr Ala Pro Ala Val Val Tyr Ile Glu Ile Leu Asp Arg
225                 230                 235                 240

His Pro Phe Leu Gly Arg Glu Val Pro Ile Ser Asn Gly Ser Gly Phe
                 245                 250                 255

Val Val Ala Ala Asp Gly Leu Ile Val Thr Asn Ala His Val Val Ala
             260                 265                 270

Asp Arg Arg Arg Val Arg Val Arg Leu Leu Ser Gly Asp Thr Tyr Glu
         275                 280                 285

Ala Val Val Thr Ala Val Asp Pro Val Ala Asp Ile Ala Thr Leu Arg
     290                 295                 300

Ile Gln Thr Lys Glu Pro Leu Pro Thr Leu Pro Leu Gly Arg Ser Ala
305                 310                 315                 320

Asp Val Arg Gln Gly Glu Phe Val Val Ala Met Gly Ser Pro Phe Ala
                 325                 330                 335

Leu Gln Asn Thr Ile Thr Ser Gly Ile Val Ser Ser Ala Gln Arg Pro
             340                 345                 350

Ala Arg Asp Leu Gly Leu Pro Gln Thr Asn Val Glu Tyr Ile Gln Thr
         355                 360                 365

Asp Ala Ala Ile Asp Phe Gly Asn Ser Gly Gly Pro Leu Val Asn Leu
     370                 375                 380

Asp Gly Glu Val Ile Gly Val Asn Thr Met Lys Val Thr Ala Gly Ile
```

```
                385                 390                 395                 400

Ser Phe Ala Ile Pro Ser Asp Arg Leu Arg Glu Phe Leu His Arg Gly
                405                 410                 415

Glu Lys Lys Asn Ser Ser Ser Gly Ile Ser Gly Ser Gln Arg Arg Tyr
                420                 425                 430

Ile Gly Val Met Met Leu Thr Leu Ser Pro Ser Ile Leu Ala Glu Leu
            435                 440                 445

Gln Leu Arg Glu Pro Ser Phe Pro Asp Val Gln His Gly Val Leu Ile
        450                 455                 460

His Lys Val Ile Leu Gly Ser Pro Ala His Arg Ala Gly Leu Arg Pro
465                 470                 475                 480

Gly Asp Val Ile Leu Ala Ile Gly Glu Gln Met Val Gln Asn Ala Glu
                485                 490                 495

Asp Val Tyr Glu Ala Val Arg Thr Gln Ser Gln Leu Ala Val Gln Ile
                500                 505                 510

Arg Arg Gly Arg Glu Thr Leu Thr Leu Tyr Val Thr Pro Glu Val Thr
            515                 520                 525

Glu

<210> SEQ ID NO 6
<211> LENGTH: 10
<212> TYPE: PRT
<213> ORGANISM: Homo sapiens
<220> FEATURE:
<221> NAME/KEY: DOMAIN
<222> LOCATION: (1)...(10)
<223> OTHER INFORMATION: signal peptide site
<220> FEATURE:
<221> NAME/KEY: VARIANT
<222> LOCATION: (1)...(10)
<223> OTHER INFORMATION: Xaa = Any Amino Acid

<400> SEQUENCE: 6

Pro Arg Ala Xaa Xaa Thr Xaa Xaa Thr Pro
  1               5                  10

<210> SEQ ID NO 7
<211> LENGTH: 7
<212> TYPE: PRT
<213> ORGANISM: Homo sapiens
<220> FEATURE:
<221> NAME/KEY: DOMAIN
<222> LOCATION: (1)...(7)
<223> OTHER INFORMATION: SH3 domain

<400> SEQUENCE: 7

Pro Pro Pro Ala Ser Pro Arg
  1               5

<210> SEQ ID NO 8
<211> LENGTH: 4
<212> TYPE: PRT
<213> ORGANISM: Homo sapiens
<220> FEATURE:
<221> NAME/KEY: DOMAIN
<222> LOCATION: (1)...(4)
<223> OTHER INFORMATION: Mxi2/p38 kinase phosphorylateion site

<400> SEQUENCE: 8

Ser Pro Arg Ser
  1

<210> SEQ ID NO 9
```

```
<211> LENGTH: 2948
<212> TYPE: DNA
<213> ORGANISM: Homo sapiens
<220> FEATURE:
<221> NAME/KEY: CDS
<222> LOCATION: (1)...(2691)

<400> SEQUENCE: 9 atg aac atc tcg gga agc agc tgt gga agc cct aac tct gca gat aca      48
Met Asn Ile Ser Gly Ser Ser Cys Gly Ser Pro Asn Ser Ala Asp Thr
 1               5                  10                  15 tct agt gac ttt aag gac ctt tgg aca aaa cta aaa gaa tgt cat gat      96
Ser Ser Asp Phe Lys Asp Leu Trp Thr Lys Leu Lys Glu Cys His Asp
             20                  25                  30 aga gaa gta caa ggt tta caa gta aaa gta acc aag cta aaa cag gaa     144
Arg Glu Val Gln Gly Leu Gln Val Lys Val Thr Lys Leu Lys Gln Glu
         35                  40                  45 cga atc tta gat gca caa aga cta gaa gaa ttc ttc acc aaa aat caa     192
Arg Ile Leu Asp Ala Gln Arg Leu Glu Glu Phe Phe Thr Lys Asn Gln
     50                  55                  60 cag ctg agg gaa cag cag aaa gtc ctt cat gaa acc att aaa gtt tta     240
Gln Leu Arg Glu Gln Gln Lys Val Leu His Glu Thr Ile Lys Val Leu
 65                  70                  75                  80 gaa gat cgg tta aga gca ggc tta tgt gat cgc tgt gca gta act gaa     288
Glu Asp Arg Leu Arg Ala Gly Leu Cys Asp Arg Cys Ala Val Thr Glu
                 85                  90                  95 gaa cat atg cgg aaa aaa cag caa gag ttt gaa aat atc cgg cag cag     336
Glu His Met Arg Lys Lys Gln Gln Glu Phe Glu Asn Ile Arg Gln Gln
            100                 105                 110 aat ctt aaa ctt att aca gaa ctt atg aat gaa agg aat act cta cag     384
Asn Leu Lys Leu Ile Thr Glu Leu Met Asn Glu Arg Asn Thr Leu Gln
        115                 120                 125 gaa gaa aat aaa aag ctt tct gaa caa ctc cag cag aaa att gag aat     432
Glu Glu Asn Lys Lys Leu Ser Glu Gln Leu Gln Gln Lys Ile Glu Asn
    130                 135                 140 gat caa cag cat caa gca gct gag ctt gaa tgt gag gaa gac gtt att     480
Asp Gln Gln His Gln Ala Ala Glu Leu Glu Cys Glu Glu Asp Val Ile
145                 150                 155                 160 cca gat tca ccg ata aca gcc ttc tca ttt tct ggc gtt aac cgg cta     528
Pro Asp Ser Pro Ile Thr Ala Phe Ser Phe Ser Gly Val Asn Arg Leu
                165                 170                 175 cga aga aag gag aac ccc cat gtc cga tac ata gaa caa aca cat act     576
Arg Arg Lys Glu Asn Pro His Val Arg Tyr Ile Glu Gln Thr His Thr
            180                 185                 190 aaa ttg gag cac tct gtg tgt gca aat gaa atg aga aaa gtt tcc aag     624
Lys Leu Glu His Ser Val Cys Ala Asn Glu Met Arg Lys Val Ser Lys
        195                 200                 205 tct tca act cat cca caa cat aat cct aat gaa aat gaa att cta gta     672
Ser Ser Thr His Pro Gln His Asn Pro Asn Glu Asn Glu Ile Leu Val
    210                 215                 220 gct gac act tat gac caa agt caa tct cca atg gcc aaa gca cat gga     720
Ala Asp Thr Tyr Asp Gln Ser Gln Ser Pro Met Ala Lys Ala His Gly
225                 230                 235                 240 aca agc agc tat acc cct gat aag tca tct ttt aat tta gct aca gtt     768
Thr Ser Ser Tyr Thr Pro Asp Lys Ser Ser Phe Asn Leu Ala Thr Val
                245                 250                 255 gtt gct gaa aca ctt gga ctt ggt gtt caa gaa gaa tct gaa act caa     816
Val Ala Glu Thr Leu Gly Leu Gly Val Gln Glu Glu Ser Glu Thr Gln
            260                 265                 270 ggt ccc atg agc ccc ctt ggt gat gag ctc tac cac tgt ctg gaa gga     864
Gly Pro Met Ser Pro Leu Gly Asp Glu Leu Tyr His Cys Leu Glu Gly
```

```
              275                 280                 285
aat cac aag aaa cag cct ttt gag gaa tct aca aga aat act gaa gat        912
Asn His Lys Lys Gln Pro Phe Glu Glu Ser Thr Arg Asn Thr Glu Asp
    290                 295                 300 agt tta aga ttt tca gat tct act tca aag act cct cct caa gaa gaa        960
Ser Leu Arg Phe Ser Asp Ser Thr Ser Lys Thr Pro Pro Gln Glu Glu
305                 310                 315                 320 tta cct act cga gtg tca tct cct gta ttt gga gct acc tct agt atc       1008
Leu Pro Thr Arg Val Ser Ser Pro Val Phe Gly Ala Thr Ser Ser Ile
                325                 330                 335 aaa agt ggt tta gat ttg aat aca agt ttg tcc cct tct ctt tta cag       1056
Lys Ser Gly Leu Asp Leu Asn Thr Ser Leu Ser Pro Ser Leu Leu Gln
            340                 345                 350 cct ggg aaa aaa aaa cat ctg aaa aca ctc cct ttt agc aac act tgt       1104
Pro Gly Lys Lys Lys His Leu Lys Thr Leu Pro Phe Ser Asn Thr Cys
        355                 360                 365 ata tct aga tta gaa aaa act aga tca aaa tct gaa gat agt gcc ctt       1152
Ile Ser Arg Leu Glu Lys Thr Arg Ser Lys Ser Glu Asp Ser Ala Leu
    370                 375                 380 ttc aca cat cac agt ctt ggg tct gaa gtg aac aag atc att atc cag       1200
Phe Thr His His Ser Leu Gly Ser Glu Val Asn Lys Ile Ile Ile Gln
385                 390                 395                 400 tca tct aat aaa cag ata ctt ata aat aaa aat ata agt gaa tcc cta       1248
Ser Ser Asn Lys Gln Ile Leu Ile Asn Lys Asn Ile Ser Glu Ser Leu
                405                 410                 415 ggt gaa cag aat agg act gag tac ggt aaa gat tct aac act gat aaa       1296
Gly Glu Gln Asn Arg Thr Glu Tyr Gly Lys Asp Ser Asn Thr Asp Lys
            420                 425                 430 cat ttg gag ccc ctg aaa tca ttg gga ggc cga aca tcc aaa agg aag       1344
His Leu Glu Pro Leu Lys Ser Leu Gly Gly Arg Thr Ser Lys Arg Lys
        435                 440                 445 aaa act gag gaa gaa agt gaa cat gaa gta agc tgc ccc caa gct tct       1392
Lys Thr Glu Glu Glu Ser Glu His Glu Val Ser Cys Pro Gln Ala Ser
    450                 455                 460 ttt gat aaa gaa aat gct ttc cct ttt cca atg gat aat cag ttt tcc       1440
Phe Asp Lys Glu Asn Ala Phe Pro Phe Pro Met Asp Asn Gln Phe Ser
465                 470                 475                 480 atg aat gga gac tgt gtg atg gat aaa cct ctg gat ctg tct gat cga       1488
Met Asn Gly Asp Cys Val Met Asp Lys Pro Leu Asp Leu Ser Asp Arg
                485                 490                 495 ttt tca gct att cag cgt caa gag aaa agc caa gga agt gag act tct       1536
Phe Ser Ala Ile Gln Arg Gln Glu Lys Ser Gln Gly Ser Glu Thr Ser
            500                 505                 510 aaa aac aaa ttt agg caa gtg act ctt tat gag gct ttg aag acc att       1584
Lys Asn Lys Phe Arg Gln Val Thr Leu Tyr Glu Ala Leu Lys Thr Ile
        515                 520                 525 cca aag ggc ttt tcc tca agc cgt aag gcc tca gat ggc aac tgc acg       1632
Pro Lys Gly Phe Ser Ser Ser Arg Lys Ala Ser Asp Gly Asn Cys Thr
    530                 535                 540 ttg ccc aaa gat tcc cca ggg gag ccc tgt tca cag gaa tgc atc atc       1680
Leu Pro Lys Asp Ser Pro Gly Glu Pro Cys Ser Gln Glu Cys Ile Ile
545                 550                 555                 560 ctt cag ccc ttg aat aaa tgc tct cca gac aat aaa cca tca tta caa       1728
Leu Gln Pro Leu Asn Lys Cys Ser Pro Asp Asn Lys Pro Ser Leu Gln
                565                 570                 575 ata aaa gaa gaa aat gct gtc ttt aaa att cct cta cgt cca cgt gaa       1776
Ile Lys Glu Glu Asn Ala Val Phe Lys Ile Pro Leu Arg Pro Arg Glu
            580                 585                 590 agt ttg gag act gag aat gtt tta gat gac ata aag agt gct ggt tct       1824
Ser Leu Glu Thr Glu Asn Val Leu Asp Asp Ile Lys Ser Ala Gly Ser
```

```
                    Ser Leu Glu Thr Glu Asn Val Leu Asp Asp Ile Lys Ser Ala Gly Ser
                        595                 600                 605 cat gag cca ata aaa ata caa acc agg tca gac cat gga gga tgt gaa                  1872
His Glu Pro Ile Lys Ile Gln Thr Arg Ser Asp His Gly Gly Cys Glu
    610                 615                 620 ctt gca tca gtt ctt cag tta aat cca tgt aga act ggt aaa ata aag                  1920
Leu Ala Ser Val Leu Gln Leu Asn Pro Cys Arg Thr Gly Lys Ile Lys
625                 630                 635                 640 tct cta caa aac aac caa gat gta tcc ttt gaa aat atc cag tgg agt                  1968
Ser Leu Gln Asn Asn Gln Asp Val Ser Phe Glu Asn Ile Gln Trp Ser
                645                 650                 655 ata gat ccg gga gca gac ctt tct cag tat aaa atg gat gtt act gta                  2016
Ile Asp Pro Gly Ala Asp Leu Ser Gln Tyr Lys Met Asp Val Thr Val
            660                 665                 670 ata gat aca aag gat ggc agt cag tca aaa tta gga gga gag aca gtg                  2064
Ile Asp Thr Lys Asp Gly Ser Gln Ser Lys Leu Gly Gly Glu Thr Val
        675                 680                 685 gac atg gac tgt aca ttg gtt agt gaa acc gtt ctc tta aaa atg aag                  2112
Asp Met Asp Cys Thr Leu Val Ser Glu Thr Val Leu Leu Lys Met Lys
    690                 695                 700 aag caa gag cag aag gga gaa aaa agt tca aat gaa gaa aga aaa atg                  2160
Lys Gln Glu Gln Lys Gly Glu Lys Ser Ser Asn Glu Glu Arg Lys Met
705                 710                 715                 720 aat gat agc ttg gaa gat atg ttt gat cgg aca aca cat gaa gag tat                  2208
Asn Asp Ser Leu Glu Asp Met Phe Asp Arg Thr Thr His Glu Glu Tyr
                725                 730                 735 gaa tcc tgt ttg gca gac agt ttc tcc caa gca gca gat gaa gag gag                  2256
Glu Ser Cys Leu Ala Asp Ser Phe Ser Gln Ala Ala Asp Glu Glu Glu
            740                 745                 750 gaa ttg tct act gcc aca aag aaa cta cac act cat ggt gat aaa caa                  2304
Glu Leu Ser Thr Ala Thr Lys Lys Leu His Thr His Gly Asp Lys Gln
        755                 760                 765 gac aaa gtc aag cag aaa gcg ttt gtg gag ccg tat ttt aaa ggt gat                  2352
Asp Lys Val Lys Gln Lys Ala Phe Val Glu Pro Tyr Phe Lys Gly Asp
    770                 775                 780 gaa aga gag act agc ttg caa aat ttt cct cat att gag tgt gtt cgg                  2400
Glu Arg Glu Thr Ser Leu Gln Asn Phe Pro His Ile Glu Cys Val Arg
785                 790                 795                 800 aaa aaa gag gag aga aga aaa ctg ctt ggg cac acg tgt aag gaa tgt                  2448
Lys Lys Glu Glu Arg Arg Lys Leu Leu Gly His Thr Cys Lys Glu Cys
                805                 810                 815 gaa att tat tat gca gat atg cca gca gaa gaa aga gaa aag aaa ttg                  2496
Glu Ile Tyr Tyr Ala Asp Met Pro Ala Glu Glu Arg Glu Lys Lys Leu
            820                 825                 830 gct tcc tgc tca aga cac cga ttc cgc tac att cca ccc aac aca cca                  2544
Ala Ser Cys Ser Arg His Arg Phe Arg Tyr Ile Pro Pro Asn Thr Pro
        835                 840                 845 gag aat ttt tgg gaa gtt ggt ttt cct tcc act cag act tgt atg gaa                  2592
Glu Asn Phe Trp Glu Val Gly Phe Pro Ser Thr Gln Thr Cys Met Glu
    850                 855                 860 aga ggt tat att aag gaa gat ctt gat cct tgt cct cgt cca aaa aga                  2640
Arg Gly Tyr Ile Lys Glu Asp Leu Asp Pro Cys Pro Arg Pro Lys Arg
865                 870                 875                 880 cgt cag cct tac aac gca ata ttt tct cca aaa ggc aag gag cag aag                  2688
Arg Gln Pro Tyr Asn Ala Ile Phe Ser Pro Lys Gly Lys Glu Gln Lys
                885                 890                 895 aca tagacgttga aacagaaaca gaaggatgaa ggacagtttt ttccttctta                       2741
Thr gttatttata gttaaagttg gtactaaaca ttgattttttt tgatcttctg taaatggatt              2801
```

```
tataaatcag ttttctattg aaaatgtttg tgatattttg cttttgcacc tttaaaacaa    2861
taaggcgctt tcattttgca ctctaactta agagttttta ctttatgtag tgatacctaa    2921
tacaattttg aaaatacaaa aaaaaaa                                        2948
```

<210> SEQ ID NO 10
<211> LENGTH: 897
<212> TYPE: PRT
<213> ORGANISM: Homo sapiens

<400> SEQUENCE: 10

```
Met Asn Ile Ser Gly Ser Ser Cys Gly Ser Pro Asn Ser Ala Asp Thr
 1               5                  10                  15

Ser Ser Asp Phe Lys Asp Leu Trp Thr Lys Leu Lys Glu Cys His Asp
             20                  25                  30

Arg Glu Val Gln Gly Leu Gln Val Lys Val Thr Lys Leu Lys Gln Glu
         35                  40                  45

Arg Ile Leu Asp Ala Gln Arg Leu Glu Glu Phe Phe Thr Lys Asn Gln
     50                  55                  60

Gln Leu Arg Glu Gln Gln Lys Val Leu His Glu Thr Ile Lys Val Leu
 65                  70                  75                  80

Glu Asp Arg Leu Arg Ala Gly Leu Cys Asp Arg Cys Ala Val Thr Glu
                 85                  90                  95

Glu His Met Arg Lys Lys Gln Gln Glu Phe Glu Asn Ile Arg Gln Gln
            100                 105                 110

Asn Leu Lys Leu Ile Thr Glu Leu Met Asn Glu Arg Asn Thr Leu Gln
        115                 120                 125

Glu Glu Asn Lys Lys Leu Ser Glu Gln Leu Gln Gln Lys Ile Glu Asn
    130                 135                 140

Asp Gln His Gln Ala Ala Glu Leu Glu Cys Glu Glu Asp Val Ile
145                 150                 155                 160

Pro Asp Ser Pro Ile Thr Ala Phe Ser Phe Ser Gly Val Asn Arg Leu
                165                 170                 175

Arg Arg Lys Glu Asn Pro His Val Arg Tyr Ile Glu Gln Thr His Thr
            180                 185                 190

Lys Leu Glu His Ser Val Cys Ala Asn Glu Met Arg Lys Val Ser Lys
        195                 200                 205

Ser Ser Thr His Pro Gln His Asn Pro Asn Glu Asn Glu Ile Leu Val
    210                 215                 220

Ala Asp Thr Tyr Asp Gln Ser Gln Ser Pro Met Ala Lys Ala His Gly
225                 230                 235                 240

Thr Ser Ser Tyr Thr Pro Asp Lys Ser Ser Phe Asn Leu Ala Thr Val
                245                 250                 255

Val Ala Glu Thr Leu Gly Leu Gly Val Gln Glu Glu Ser Glu Thr Gln
            260                 265                 270

Gly Pro Met Ser Pro Leu Gly Asp Glu Leu Tyr His Cys Leu Glu Gly
        275                 280                 285

Asn His Lys Lys Gln Pro Phe Glu Glu Ser Thr Arg Asn Thr Glu Asp
    290                 295                 300

Ser Leu Arg Phe Ser Asp Ser Thr Ser Lys Thr Pro Pro Gln Glu Glu
305                 310                 315                 320

Leu Pro Thr Arg Val Ser Ser Pro Val Phe Gly Ala Thr Ser Ser Ile
                325                 330                 335

Lys Ser Gly Leu Asp Leu Asn Thr Ser Leu Ser Pro Ser Leu Leu Gln
```

-continued

```
                340                 345                 350
Pro Gly Lys Lys Lys His Leu Lys Thr Leu Pro Phe Ser Asn Thr Cys
            355                 360                 365

Ile Ser Arg Leu Glu Lys Thr Arg Ser Lys Ser Glu Asp Ser Ala Leu
370                 375                 380

Phe Thr His His Ser Leu Gly Ser Glu Val Asn Lys Ile Ile Ile Gln
385                 390                 395                 400

Ser Ser Asn Lys Gln Ile Leu Ile Asn Lys Asn Ile Ser Glu Ser Leu
            405                 410                 415

Gly Glu Gln Asn Arg Thr Glu Tyr Gly Lys Asp Ser Asn Thr Asp Lys
            420                 425                 430

His Leu Glu Pro Leu Lys Ser Leu Gly Gly Arg Thr Ser Lys Arg Lys
            435                 440                 445

Lys Thr Glu Glu Glu Ser Glu His Glu Val Ser Cys Pro Gln Ala Ser
450                 455                 460

Phe Asp Lys Glu Asn Ala Phe Pro Phe Pro Met Asp Asn Gln Phe Ser
465                 470                 475                 480

Met Asn Gly Asp Cys Val Met Asp Lys Pro Leu Asp Leu Ser Asp Arg
            485                 490                 495

Phe Ser Ala Ile Gln Arg Gln Glu Lys Ser Gln Gly Ser Glu Thr Ser
            500                 505                 510

Lys Asn Lys Phe Arg Gln Val Thr Leu Tyr Glu Ala Leu Lys Thr Ile
            515                 520                 525

Pro Lys Gly Phe Ser Ser Ser Arg Lys Ala Ser Asp Gly Asn Cys Thr
            530                 535                 540

Leu Pro Lys Asp Ser Pro Gly Glu Pro Cys Ser Gln Glu Cys Ile Ile
545                 550                 555                 560

Leu Gln Pro Leu Asn Lys Cys Ser Pro Asp Asn Lys Pro Ser Leu Gln
            565                 570                 575

Ile Lys Glu Glu Asn Ala Val Phe Lys Ile Pro Leu Arg Pro Arg Glu
            580                 585                 590

Ser Leu Glu Thr Glu Asn Val Leu Asp Asp Ile Lys Ser Ala Gly Ser
            595                 600                 605

His Glu Pro Ile Lys Ile Gln Thr Arg Ser Asp His Gly Gly Cys Glu
            610                 615                 620

Leu Ala Ser Val Leu Gln Leu Asn Pro Cys Arg Thr Gly Lys Ile Lys
625                 630                 635                 640

Ser Leu Gln Asn Asn Gln Asp Val Ser Phe Glu Asn Ile Gln Trp Ser
            645                 650                 655

Ile Asp Pro Gly Ala Asp Leu Ser Gln Tyr Lys Met Asp Val Thr Val
            660                 665                 670

Ile Asp Thr Lys Asp Gly Ser Gln Ser Lys Leu Gly Gly Glu Thr Val
            675                 680                 685

Asp Met Asp Cys Thr Leu Val Ser Glu Thr Val Leu Leu Lys Met Lys
690                 695                 700

Lys Gln Glu Gln Lys Gly Glu Lys Ser Ser Asn Glu Glu Arg Lys Met
705                 710                 715                 720

Asn Asp Ser Leu Glu Asp Met Phe Asp Arg Thr Thr His Glu Glu Tyr
            725                 730                 735

Glu Ser Cys Leu Ala Asp Ser Phe Ser Gln Ala Ala Asp Glu Glu Glu
            740                 745                 750

Glu Leu Ser Thr Ala Thr Lys Lys Leu His Thr His Gly Asp Lys Gln
            755                 760                 765
```

-continued

```
Asp Lys Val Lys Gln Lys Ala Phe Val Glu Pro Tyr Phe Lys Gly Asp
    770                 775                 780
Glu Arg Glu Thr Ser Leu Gln Asn Phe Pro His Ile Glu Cys Val Arg
785                 790                 795                 800
Lys Lys Glu Glu Arg Arg Lys Leu Leu Gly His Thr Cys Lys Glu Cys
                805                 810                 815
Glu Ile Tyr Tyr Ala Asp Met Pro Ala Glu Arg Glu Lys Lys Leu
                820                 825                 830
Ala Ser Cys Ser Arg His Arg Phe Arg Tyr Ile Pro Pro Asn Thr Pro
                835                 840                 845
Glu Asn Phe Trp Glu Val Gly Phe Pro Ser Thr Gln Thr Cys Met Glu
    850                 855                 860
Arg Gly Tyr Ile Lys Glu Asp Leu Asp Pro Cys Pro Arg Pro Lys Arg
865                 870                 875                 880
Arg Gln Pro Tyr Asn Ala Ile Phe Ser Pro Lys Gly Lys Glu Gln Lys
                885                 890                 895
Thr
```

<210> SEQ ID NO 11
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: RB family binding motif
<220> FEATURE:
<221> NAME/KEY: VARIANT
<222> LOCATION: (1)...(5)
<223> OTHER INFORMATION: Xaa = Any Amino Acid

<400> SEQUENCE: 11

```
Leu Xaa Cys Xaa Glu
 1               5
```

<210> SEQ ID NO 12
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: E1A/CtBP binding motif

<400> SEQUENCE: 12

```
Pro Leu Asp Leu Ser
 1               5
```

<210> SEQ ID NO 13
<211> LENGTH: 416
<212> TYPE: DNA
<213> ORGANISM: Homo sapiens

<400> SEQUENCE: 13

```
ttgtattttc aaaattgtat taggtatcac tacataaagt aaaaactctt aagttagagt      60
gcaaaatgaa agcgccttat tgttttaaag gtgcaaaagc aaaatatcac aaacattttc     120
aatagaaaac tgatttataa atccatttac agaagatcaa aaaaatcaat gtttagtacc     180
aactttaact ataataaact aagaaggaaa aaactgtcct tcatccttct gtttctgttt     240
caacgtctat gtcttctgct ccttgccttt tggagaaaat attgcgttgt aaggctgagc     300
```

```
tcttttttgga cgaggacaag gatcaagatc ttccttaata taacctcttt ccatacaagt    360
ctgagtggaa ggaaaaccaa cttcccaaaa attctctggt gtgttgggtg gaatgt        416
```

<210> SEQ ID NO 14
<211> LENGTH: 408
<212> TYPE: DNA
<213> ORGANISM: Homo sapiens
<220> FEATURE:
<221> NAME/KEY: misc_feature
<222> LOCATION: (1)...(408)
<223> OTHER INFORMATION: n = A,T,C or G

<400> SEQUENCE: 14

```
gcaccgatac cggcgcgggc acctggggag aaatggatgg agaagggacc tggcntggaa      60
acatttgccc cgctgctctg ctccgcccat aagaggaccc cntgaaatgt cccgtgcagt    120
ttgttcaagt cccntgtgt gatgaaatgt gcctctcgcc ttacccgtgt gagaatacct     180
gtggtgtggc agcgagtatt ttggtatttg acctgtccaa agacgacttg atacctctat    240
aatgtaacag aaaaggtcag aaaatattaa gcaagtagaa gtgtggagca tattaagcaa    300
gatgaacatc tcgggaagca gctgtggaag ccctaactct gcagatacat ctagtgactt    360
taaggacctt tggacaaaac taaagaatg tcatgataga gaagtacc                  408
```

<210> SEQ ID NO 15
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: leucine zipper domain

<400> SEQUENCE: 15

```
Leu Glu Cys Glu Glu
 1               5
```

<210> SEQ ID NO 16
<211> LENGTH: 307
<212> TYPE: PRT
<213> ORGANISM: Homo sapiens

<400> SEQUENCE: 16

```
Met Glu Ala Asp Lys Asp Asp Thr Gln Gln Ile Leu Lys Glu His Ser
 1               5                  10                  15

Pro Asp Glu Phe Ile Lys Asp Glu Gln Asn Lys Gly Leu Ile Asp Glu
                20                  25                  30

Ile Thr Lys Lys Asn Ile Gln Leu Lys Lys Glu Ile Gln Lys Leu Glu
        35                  40                  45

Thr Glu Leu Gln Glu Ala Thr Lys Glu Phe Gln Ile Lys Glu Asp Ile
    50                  55                  60

Pro Glu Thr Lys Met Lys Phe Leu Ser Val Glu Thr Pro Glu Asn Asp
65                  70                  75                  80

Ser Gln Leu Ser Asn Ile Ser Cys Ser Phe Gln Val Ser Ser Lys Val
                85                  90                  95

Pro Tyr Glu Ile Gln Lys Gly Gln Ala Leu Ile Thr Phe Glu Lys Glu
            100                 105                 110

Glu Val Ala Gln Asn Val Val Ser Met Ser Lys His His Val Gln Ile
        115                 120                 125

Lys Asp Val Asn Leu Glu Val Thr Ala Lys Pro Val Pro Leu Asn Ser
    130                 135                 140
```

-continued

```
Gly Val Arg Phe Gln Val Tyr Val Glu Val Ser Lys Met Lys Ile Asn
145                 150                 155                 160

Val Thr Glu Ile Pro Asp Thr Leu Arg Glu Asp Gln Met Arg Asp Lys
                165                 170                 175

Leu Glu Leu Ser Phe Ser Lys Phe Arg Asn Gly Gly Gly Glu Val Asp
            180                 185                 190

Arg Val Asp Tyr Asp Arg Gln Ser Gly Ser Ala Val Ile Thr Phe Val
        195                 200                 205

Glu Ile Gly Val Ala Asp Lys Ile Leu Lys Lys Lys Glu Tyr Pro Leu
    210                 215                 220

Tyr Ile Asn Gln Thr Cys His Arg Val Thr Val Ser Pro Tyr Thr Glu
225                 230                 235                 240

Ile His Leu Lys Lys Tyr Gln Ile Phe Ser Gly Thr Ser Lys Arg Thr
                245                 250                 255

Val Leu Leu Thr Gly Met Glu Gly Ile Gln Met Asp Glu Glu Ile Val
            260                 265                 270

Glu Asp Leu Ile Asn Ile His Phe Gln Arg Ala Lys Asn Gly Gly Gly
        275                 280                 285

Glu Val Asp Val Val Lys Cys Ser Leu Gly Gln Pro His Ile Ala Tyr
    290                 295                 300

Phe Glu Glu
305
```

CELL PROLIFERATION RELATED GENES

This application claims the benefit of provisional application No. 60/046,077 filed May 9, 1997.

BACKGROUND OF THE INVENTION

The invention relates to the Nmi, Omi and Rim genes, their products, and uses thereof.

SUMMARY OF THE INVENTION

Nmi Gene

The present invention is based, in part, on the discovery of the gene which encodes a protein which interacts with myc proteins.

Accordingly, the invention features, a recombinant, isolated, or substantially pure, preparation of an Nmi polypeptide. An Nmi polypeptide can be a full length or a fragment.

In preferred embodiments, the Nmi polypeptide has one or more of the following properties:

it is approximately 307 amino acids in length;

it has at least one activity of naturally occurring Nmi, e.g., it can bind to a Nmi ligand, e.g., a myc gene product, e.g., N-myc or C-myc;

it has a carboxy terminus which is has at least 15, more preferably 20, or 25% sequence identity with residues 79–264 of IFP 35 of SEQ ID NO:3 or at least 50, 60, 70, 80, 90, 95, 99 or 100% sequence identity with residues 102–307 of SEQ ID NO:1 on SEQ ID NO:16;

it has an amino terminus which is has at least 15, more preferably at least 20 or 22% sequence identity with the coiled coil heptad repeat of residues 104–188 of the *C. elegans* protein CEF59 of SEQ ID NO:2 or at least 50 60 70, 80, 90, 95, 99 or 100% sequence identity with residues 2–86 of SEQ ID NO:1 on SEQ ID NO:16;

it has at least 60, and more preferably at least 70, 80, 90, 95, 99, or 100% sequence identity with the protein encoded in SEQ ID NO:1 on SEQ ID NO:16.

In preferred embodiments, the polypeptide has biological activity, e.g., the polypeptide is either, an agonist or an antagonist, of a biological activity of a naturally occurring Nmi.

In preferred embodiments, the polypeptide is a vertebrate, e.g., a mammalian, e.g. a primate, e.g., a human, Nmi polypeptide.

In preferred embodiments, the Nmi polypeptide includes a domain, e.g., an amino terminal domain, which has at least 50, 60, 70, 80, 90, 99 or 100% sequence identity with residues 2–86 of the Nmi sequence of SEQ ID NO:1 on SEQ ID NO:16, or 50, 60, 70, 80, 90, 95, 99 or 100% sequence identity with residues 104–188 of the CEF59 sequence in SEQ ID NO:2.

In preferred embodiments, the polypeptide includes one or more of the following: a region which has at least 60, more preferably at least 70, 80, 90, or 100% sequence identity with residues 2–14 of SEQ ID NO:1 on SEQ ID NO:16 (or residues 104–116 of SEQ ID NO:2); a region which has at least 60, more preferably at least 70, 80, 90, or 100% sequence identity with residues 27–44 of SEQ ID NO:1 on SEQ ID NO:16 (or residues 129–146 of SEQ ID NO:2); a region which has at least 60, more preferably at least 70, 80, 90, or 100% sequence identity with residues 51–59 of SEQ ID NO:1 on SEQ ID NO:16 (or residues 153–161 of SEQ ID NO:2); or a region which has at least 60, more preferably at least 70, 80, 90, or 100% sequence identity with residues 76–86 of SEQ ID NO:1 on SEQ ID NO:16 (or residues 178–188 of SEQ ID NO:2).

In preferred embodiments, the Nmi polypeptide includes a coiled coil region, preferably in the carboxy terminus or half of the polypeptide, which has at least 50, 60, 70, 80, 90, 95, 99 or 100% sequence identity with the residues 102–288 of the Nmi sequence of SEQ ID NO:1 on SEQ ID NO:16 or 50, 60, 70, 80, 90, 95, 99 or 100% sequence identity with residues 79–264 of the IFP35 sequence in SEQ ID NO:3, or a segment of one of these regions sufficient to mediate binding to a Nmi ligand.

In preferred embodiments, the polypeptide includes one or more of the following: a region which has at least 60, more preferably at least 70, 80, 90, or 100% sequence identity with residues 103–126 of SEQ ID NO:1 on SEQ ID NO:16 (or residues 79–102 of SEQ ID NO:3); a region which has at least 60, more preferably at least 70, 80, 90, or 100% sequence identity with residues 133–142 of SEQ ID NO:1 on SEQ ID NO:16 (or residues 109–118 of SEQ ID NO:3); a region which has at least 60, more preferably at least 70, 80, 90, or 100% sequence identity with residues 149–168 of SEQ ID NO:1on SEQ ID NO:16 (or residues 125–144 of SEQ ID NO:3); a region which has at least 60, more preferably at least 70, 80, 90, or 100% sequence identity with residues 201–218 of SEQ ID NO:1 on SEQ ID NO:16 (or residues 177–194 of SEQ ID NO:3); a region which has at least 60, more, preferably at least 70, 80, 90, or 100% sequence identity with residues 233–250 of SEQ ID NO:1on SEQ ID NO:16 (or residues 209–226 of SEQ ID NO:3); a region which has at least 60, more preferably at least 70, 80, 90, or 100% sequence identity with residues 255–259 of SEQ ID NO:1on SEQ ID NO:16 (or residues 231–235 of SEQ ID NO:3); a region which has at least 60, more preferably at least 70, 80, 90, or 100% sequence identity with residues 270–275 of SEQ ID NO:1 on SEQ ID NO:16 (or residues 246–251 of SEQ ID NO:3); or a region which has at least 60, more preferably at least 70, 80, 90, or 100 % sequence identity with residues 281–288 of SEQ ID NO:1on SEQ ID NO:16 (or residues 257–264 of SEQ ID NO:3).

In a preferred embodiment, the Nmi polypeptide differs in amino acid sequence at up to 1, 2, 3, 5, or 10 residues, from the sequence in SEQ ID NO:1 on SEQ ID NO:16. In other preferred embodiments, the Nmi polypeptide differs in amino acid sequence at up to 1, 2, 3, 5, or 10% of the residues from a sequence in SEQ ID NO:1 on SEQ ID NO:16. In preferred embodiments, the differences are such that the Nmi polypeptide exhibits an Nmi biological activity. In other preferred embodiments the differences are such that the Nmi polypeptide does not have Nmi biological activity. In preferred embodiments,one or more, or all of the differences are conservative amino acid changes. In other preferred embodiments one or more, or all of the differences are other than conservative amino acid changes.

In preferred embodiments, the Nmi polypeptide includes a Nmi sequence described herein as well as other N-terminal and/or C-terminal amino acid sequence.

In yet other preferred embodiments, the Nmi polypeptide is a recombinant fusion protein having a first Nmi portion and a second polypeptide portion, e.g., a second polypeptide portion having an amino acid sequence unrelated to Nmi. The second polypeptide portion can be, e.g., any of glutathione-S-transferase, a DNA binding domain, or a polymerase activating domain. In preferred embodiment the fusion protein can be used in a two-hybrid assay.

In a preferred embodiment, there is at least 70, 80, 90, 95, 99, or 100% sequence identity between the Nmi polypeptide and the portions of SEQ ID NO:1 on SEQ ID NO:16 which share 100 sequence identity with the aligned SEQ ID NOS 2 and 3 of FIG. 2.

In another aspect, the invention features an Nmi polypeptide which is a fragment of a full length Nmi polypeptide, e.g., a fragment of a naturally occurring Nmi polypeptide, e.g., the polypeptide encoded in SEQ ID NO:1 on SEQ ID NO:16.

In preferred embodiments: the fragment is at least 5, 10, 20, 50, 100, or 150 amino acids in length; the fragment is equal to or less than 200, 150, 100, 50 amino acid residues in length; the fragment has a biological activity of a naturally occurring Nmi; the fragment is either, an agonist or an antagonist, of a biological activity of a naturally occurring Nmi; the fragment can inhibit, e.g., competitively or non competitively inhibit, the binding of Nmi to an Nmi-ligand, e.g., a myc protein.

In preferred embodiments, the fragment it has at least 60, and more preferably at least 70, 80, 90, 95, 99, or, 100% sequence identity with the corresponding amino acid sequence of SEQ ID NO:1 on SEQ ID NO:16.

In preferred embodiments, the fragment is a fragment of a vertebrate, e.g., a mammalian, e.g. a primate, e.g., a human, Nmi polypeptide.

In preferred embodiments, the Nmi fragment includes a domain, e.g., an amino terminal domain, which has at least 50, 60, 70, 80, 90, 95, 99 or 100% sequence identity with residues 2–86 of the Nmi sequence of SEQ ID NO:1 on SEQ ID NO:16, or 50, 60, 70, 80, 90, 95, 99 or 100% sequence identity with residues 104–188 of the CEF59 sequence in SEQ ID NO:2.

In preferred embodiments, the Nmi fragment includes one, two, three, or more amino terminal homology domains. The amino terminal homology domains are as follows: residues 2–14 of SEQ ID NO:1 on SEQ ID NO:16 (or residues 104–116 of SEQ ID NO:2); residues 27–44 of SEQ ID NO:1 on SEQ ID NO:16 (or residues 129–146 of SEQ ID NO:2); residues 51–59 of SEQ ID NO:1 on SEQ ID NO:16 (or residues 153–161 of SEQ ID NO:2); residues 76–86 of SEQ ID NO:1 on SEQ ID NO:16 (or residues 178–188 of SEQ ID NO:2). In preferred embodiments, the fragment includes a region which has at least 50, 60, 70, 80, 90, 95, 99 or 100% sequence identity with an amino terminal homology domain. In preferred embodiments, the fragment (which term includes terminal and internal deletions) lacks at least one amino terminal homology domain found in naturally occurring Nmi.

In preferred embodiments, the Nmi polypeptide includes a coiled coil region, preferably in the carboxy terminus or half of the polypeptide, which has at least 50, 60, 70, 80, 90, 95, 99 or 100% sequence identity with the residues 102–288 of the Nmi sequence of SEQ ID NO:1 or 50, 60, 70, 80, 90, 95, 99 or 100% sequence identity with residues 79–264 of the IFP35 sequence in SEQ ID NO:3, or a segment of one of these regions sufficient to mediate binding to a Nmi ligand.

In preferred embodiments, the Nmi fragment includes one, two, three, or more carboxy terminal homology domains. The carboxy terminal homology domains are as follows: residues 103–126 of SEQ ID NO:1 on SEQ ID NO:16 (or residues 79–102 of SEQ ID NO:3); residues 133–142 of SEQ ID NO:1 on SEQ ID NO:16 (or residues 109–118 of SEQ ID NO:3); residues 149–168 of SEQ ID NO:1 on SEQ ID NO:1 or residues 125–144 of SEQ ID NO:3); residues 201–218 of SEQ ID NO:1 on SEQ ID NO:16 (or residues 177–194 of SEQ ID NO:3); residues 233–250 of SEQ ID NO:1 on SEQ ID NO:1 (or residues 209–226 of SEQ ID NO:3); residues 255–259 of SEQ ID NO:1 (or residues 231–235 of SEQ ID NO:3); residues 270–275 of SEQ ID NO:1. on SEQ ID NO:16 (or residues 246–251 of SEQ ID NO:3); residues 281–288 of SEQ ID NO:1 on SEQ ID NO:16 (or residues 257–264 of SEQ ID NO:3).

In preferred embodiments, the fragment includes a region which has at least 50, 60, 70, 80, 90, 95, 99 or 100% sequence identity with a carboxy terminal homology domain. In preferred embodiments, the fragment (which term includes terminal and internal deletions) lacks at least one carboxy terminal homology domain found in naturally occurring Nmi.

In preferred embodiments, the fragment can inhibit an interaction, e.g., binding, between Nmi and an Nmi-ligand. In preferred embodiments, the fragment does not inhibit an interaction, e.g., binding, between Nmi and an Nmi-ligand.

In a preferred embodiment, the fragment differs in amino acid sequence at up to 1, 2, 3, 5, or 10 residues, from the corresponding residues in SEQ ID NO:1 on SEQ ID NO:16. In other preferred embodiments, the fragment differs in amino acid sequence at up to 1, 2, 3, 5, or 10% of the residues from the corresponding residues in SEQ ID NO:1 on SEQ ID NO:16. In preferred embodiments, the differences are such that the fragment exhibits an Nmi biological activity. In other preferred embodiments the differences are such that the fragment does not have Nmi biological activity. In preferred embodiments, one or more, or all of the differences are conservative amino acid changes. In other preferred embodiments one or more, or all of the differences are other than conservative amino acid changes.

In preferred embodiments, the fragment includes an Nmi sequence described herein as well as other N-terminal and/or C-terminal amino acid sequence.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed Nmi is expressed in a native cell, or in systems which result in the omission of postranslational modifications present when expressed in a native cell.

The invention includes an immunogen which includes a Nmi polypeptide in an immunogenic preparation, the immunogen being capable of eliciting an immune response specific for the Nmi polypeptide, e.g., a humoral response, an antibody response, or a cellular response. In preferred embodiments, the immunogen comprising an antigenic determinant, e.g., a unique determinant, from a protein represented by SEQ ID NO:1.

The present invention also includes an antibody preparation specifically reactive with an epitope of the Nmi immunogen or generally of a Nmi polypeptide, preferably an epitope which consists all or in part of residues from the amino terminal or coiled-coil domain, an epitope, which when bound to an antibody, results in the modulation of a biological activity, or carboxy or amino terminal homology domain described herein.

In another aspect, the invention features, a composition which includes a Nmi polypeptide (or a nucleic acid which encodes it) and one or more additional components, e.g., a carrier, diluent, adjuvent, or solvent. The additional component can be one which renders the composition useful for in vitro, in vivo, pharmaceutical, or veterinary use.

In another aspect, the invention provides a substantially pure nucleic acid having or comprising a nucleotide sequence which encodes a polypeptide, the amino acid sequence of which includes, or is, the sequence of a Nmi polypeptide.

In preferred embodiments, the encoded Nmi polypeptide has one or more of the following properties:

it is approximately 307 amino acids in length;

it has at least one activity of naturally occurring Nmi, e.g., it can bind to a Nmi ligand, e.g., a myc gene product, e.g., N-myc or C-myc;

it has a carboxy terminus which is has at least 15, more preferably 20, or 25% sequence identity with residues 79–264 of IFP 35 of SEQ ID NO:3 or at least 50, 60, 70, 80, 90, 95, 99 or 100% sequence identity with residues 102–307 of SEQ ID NO:1 on SEQ ID NO:16.

it has an amino terminus which is has at least 15, more preferably at least 20 or 22% sequence identity with the coiled coil heptad repeat of residues 104–188 of the *c. elegans* protein CEF59 of SEQ ID NO:2 or at least 50, 60, 70, 80, 90, 95, 99 or 100% sequence identity with residues 2–86 of SEQ ID NO:1 on SEQ ID NO:16;

it has at least 60, and more preferably at least 70, 80, 90, 95, 99, or 100% sequence identity with the protein encoded in SEQ ID NO:1 on SEQ ID NO:16.

In preferred embodiments, the encoded polypeptide has biological activity, e.g., the polypeptide is either, an agonist or an antagonist, of a biological activity of a naturally occurring Nmi.

In preferred embodiments, the encoded polypeptide is a vertebrate, e.g., a mammalian, e.g. a primate, e.g., a human, Nmi polypeptide.

In preferred embodiments, the encoded Nmi polypeptide includes a domain, e.g., an amino terminal domain, which has at least 50, 60, 70, 80, 95, 99 or 100% sequence identity with residues 2–86 of the Nmi sequence of SEQ ID NO:1 on SEQ ID NO:16, or 50, 60, 70, 80, 90, 95, 99 or 100% sequence identity with residues 104–188 of the CEF59 sequence in SEQ ID NO:2.

In preferred embodiments, the encoded polypeptide includes one or more of the following: a region which has at least 60, more preferably at least 70, 80, 90, or 100% sequence identity with residues 2–14 of SEQ ID NO:1 on SEQ ID NO:16 (or residues 104–116 of SEQ ID NO:2); a region which has at least 60, more preferably at least 70, 80, 90, or 100% sequence identity with residues 27–44 or SEQ ID NO:1 on SEQ ID NO:16 (or residues 129–146 of SEQ ID NO:2); a region which has at least 60, more preferably at least 70, 80, 90, or 100% sequence identity with residues 51–59 of SEQ ID NO:1 on SEQ ID NO:16 (or residues 153–161 of SEQ ID NO:2); or a region which has at least 60, more preferably at least 70, 80, 90, or 100% sequence identity with residues 76–86 of SEQ ID NO:1 on SEQ ID NO:16 (or residues 178–188 of SEQ ID NO:2).

In preferred embodiments, the encoded Nmi polypeptide includes a coiled coil region, preferably in the carboxy terminus or half of the polypeptide, which has at least 50, 60, 70, 80, 90, 95, 99 or 00%;,sequence identity with the residues 102–288 of the Nmi sequence of SEQ ID NO:1 on SEQ ID NO:16 or 50, 60, 70, 80, 90, 95, 99 or 100% sequence identity with residues 79–264 of the IFP35 sequence in SEQ ID NO:3, or a segment of one of these regions sufficient to mediate binding to a Nmi ligand.

In preferred embodiments, the encoded polypeptide includes one or more of the following: a region which has at least 60, more preferably at least 70, 80, 90, or 100% sequence identity with residues 103–126 of SEQ ID NO:1 on SEQ ID NO:16 (or residues 79–102 of SEQ ID NO:3); a region which has at least 60, more preferably at least 70, 80, 90, or 100% sequence identity with residues 133–142of: SEQ ID NO:1 on SEQ ID NO:16 (or residues 109–118 of SEQ ID NO:3); a region which has at least 60, more preferably at least 70, 80, 90, or 100% sequence identity with residues 149–168 of SEQ ID NO:1 on SEQ ID NO:16 (or residues 125–144 of SEQ ID NO:3); a region which has at least 60, more preferably at least 70, 80, 90, or 100% sequence identity with residues 201–218 of SEQ ID NO:1 on SEQ ID NO:16 (or residues 177–194 of SEQ ID NO:3); a region which has at least 60, more preferably at least 70, 80, 90, or 100% sequence identity with residues 233–250 of SEQ ID NO:1 on SEQ ID NO:16 (or residues 209–226 of SEQ ID NO:3); a region which has at least 60, more preferably at least 70, 80, 90, or 100% sequence identity with residues 255–259 of SEQ ID NO:1 on SEQ ID NO:16 (or residues 231–235 of SEQ ID NO:3); a region which has at least 60, more preferably at least 70, 80, 90, or 100% sequence identity with residues 270–275 of SEQ ID NO:1 on SEQ ID NO:16 (or residues 246–251 of SEQ ID NO:3); or a region which has at least 60, more preferably at least 70, 80, 90, or 100% sequence identity with residues 281–288 of SEQ ID NO:1 on SEQ ID NO:16 (or residues 257–264 of SEQ ID NO:3).

In a preferred embodiment, the encoded Nmi polypeptide differs in amino acid sequence at up to 1, 2, 3, 5, or 10 residues, from the sequence in SEQ ID NO:1 on SEQ ID NO:16. In other preferred embodiments, the Nmi polypeptide differs in amino acid sequence at up to 1, 2, 3, 5, or 10% of the residues from a sequence in SEQ ID NO:1 on SEQ ID NO:16. In preferred embodiments, the differences are such that the Nmi polypeptide exhibits an Nmi biological activity. In other preferred embodiments the differences are such that the Nmi polypeptide does not have Nmi biological activity. In preferred embodiments, one or more, or all of the differences are conservative amino acid changes. In other preferred embodiments, one or more, or all of the differences are other than conservative amino acid changes.

In preferred embodiments, the encoded Nmi polypeptide includes a Nmi sequence described herein as well as other N-terminal and/or C-terminal amino acid sequence.

In yet other preferred embodiments, the encoded Nmi polypeptide is a recombinant fusion protein having a first Nmi portion and a second polypeptide portion, e.g., a second polypeptide portion having an amino acid sequence unrelated to Nmi. The second polypeptide portion can be, e.g., any of glutathione-S-transferase, a DNA binding domain, or a polymerase activating domain. In preferred embodiment the fusion protein can be used in a two-hybrid assay.

In a preferred embodiment, there is at least 70, 80, 90, 95, 99 or 100% sequence identity between the encoded Nmi polypeptide and the portions of SEQ ID NO:1on SEQ ID NO:16 which share 100 sequence identity with the aligned SEQ ID NOS 2 and 3 of FIG. 2.

The encoded polypeptide can be a fragment of a full length Nmi polypeptide, e.g., a fragment of a naturally occurring Nmi polypeptide, e.g., the polypeptide encoded in SEQ ID NO:1.

In preferred embodiments: the encoded fragment is at least 5, 10, 20, 50, 100, or 150 amino acids in length; the encoded fragment is equal to or less than 200, 150, 100, 50 amino acid residues in length; the encoded fragment has a biological activity of a naturally occurring Nmi; the encoded fragment is either, an agonist or an antagonist, of a biological activity of a naturally occurring Nmi; the encoded fragment can inhibit, e.g., competitively or non competitively inhibit, the binding of Nmi to an Nmi-ligand, e.g., a myc protein.

In preferred embodiments, the encoded fragment it has at least 60, and more preferably at least 70, 80, 90, 95, 99, or 100% sequence identity with the corresponding amino acid sequence of SEQ ID NO:1 on SEQ ID NO:16.

In preferred embodiments, the encoded fragment is a fragment of a vertebrate, e.g., a mammalian, e.g. a primate, e.g., a human, Nmi polypeptide.

In preferred embodiments, the encoded Nmi fragment includes a domain, e.g., an amino terminal domain, which has at least 50, 60, 70, 80, 95, 99 or 100% sequence identity with residues 2–86 of the Nmi sequence of SEQ ID NO:1 on SEQ ID NO:16, or 50, 60, 70, 80, 90, 95, 99 or 100% sequence identity with residues 104–188 of the CEF59 sequence in SEQ ID NO:2.

In preferred embodiments, the encoded Nmi fragment includes one, two, three, or more amino terminal homology domains. The amino terminal homology domains are as follows: residues 2–1 of SEQ ID NO:1 on SEQ ID NO:16 (or residues 104–116 of SEQ ID NO:2); residues 27–44 of SEQ ID NO:1 on SEQ ID NO:16 (or residues 129–146 of SEQ ID NO:2); residues 51–59 of SEQ ID NO:1 on SEQ ID NO:16 (or residues 153–161 of SEQ ID NO:2); residues 76–86 of SEQ ID NO:1 on SEQ ID NO:16 (or residues 178–188 of SEQ ID NO:2). In preferred embodiments, the encoded fragment includes a region which has at least 50, 60, 70, 80, 90, 95, 99 or 100% sequence identity with an amino terminal homology domain. In preferred embodiments, the encoded fragment (which term includes terminal and internal deletions) lacks at least one amino terminal homology domain found in naturally occurring Nmi.

In preferred embodiments, the encoded Nmi polypeptide includes a coiled coil region, preferably in the carboxy terminus or half of the polypeptide, which has at least 50, 60, 70, 80, 90, 95, 99 or 100% sequence identity with the residues 102–288 of the Nmi sequence of SEQ ID NO:1 on SEQ ID NO:16 or 50, 60, 70, 80, 90, 95, 99 or 100% sequence identity with residues 79–264 of the IFP35 sequence in SEQ ID NO:3, or a segment of one of these regions sufficient to mediate binding to a Nmi ligand.

In preferred embodiments, the encoded Nmi fragment includes one, two, three, or more carboxy terminal homology domains. The carboxy terminal homology domains are as follows: residues 103–126 of SEQ ID NO:1 on SEQ ID NO:16 (or residues 79–102 of SEQ ID NO:3); residues 133–142 of SEQ ID NO:1 on SEQ ID NO:16 (or residues 109–118 of SEQ ID NO:3); residues 149–168of SEQ ID NO:1 on SEQ ID NO:16 (or residues 125–144 of SEQ ID NO:3); residues 201–218 of SEQ ID NO:1 on SEQ ID NO:16 (or residues 177–194 of SEQ ID NO:3); residues 233–250 of SEQ ID NO:1on SEQ ID NO:16 (or residues 209–226 of SEQ ID NO:3); residues 255–259 of SEQ ID NO:1 (or residues 231–235 of SEQ ID NO:3); residues 270–275 of SEQ ID NO:1 on SEQ ID NO:16 (or residues 246–251 of SEQ ID NO:3); residues 281–288 of SEQ ID NO:1 on SEQ ID NO:16 (or residues 257–264 of SEQ ID NO:3).

In preferred embodiments, the encoded fragment includes a region which has at least 50, 60, 70, 80, 90, 95, 99 or 100% sequence identity with a carboxy terminal homology domain. In preferred embodiments, the encoded fragment (which term includes terminal and internal deletions) lacks at least one carboxy terminal homology domain found in naturally occurring Nmi.

In preferred embodiments, the encoded fragment can inhibit an interaction, e.g., binding, between Nmi and an Nmi-ligand. In preferred embodiments, the encoded fragment does not inhibit an interaction, e.g., binding, between Nmi and an Nmi-ligand.

In a preferred embodiment, the encoded fragment differs in amino acid sequence at up to 1, 2, 3, 5, or 10 residues, from the corresponding residues in SEQ ID NO:1 on SEQ ID NO:16. In other preferred embodiments, the encoded fragment differs in amino acid sequence at up to 1, 2, 3, 5, or 10% of the residues from the corresponding residues in SEQ ID NO:1 on SEQ ID NO:16. In preferred embodiments, the differences are such that the encoded fragment exhibits an Nmi biological activity. In other preferred embodiments, the differences are such that the encoded fragment does not have Nmi biological activity. In preferred embodiments, one or more, or all of the differences are conservative amino acid changes. In other preferred embodiments, one or more, or all of the differences are other than conservative amino acid changes.

In preferred embodiments, the encoded fragment includes an Nmi sequence described herein as well as other N-terminal and/or C-terminal amino acid sequence.

In preferred embodiments, the subject Nmi nucleic acid includes a transcriptional regulatory sequence, e.g. at least one of a transcriptional promoter or transcriptional enhancer sequence, operably linked to the Nmi gene sequence, e.g., to render the Nmi gene sequence suitable for use as an expression vector.

In another aspect, the invention features a purified nucleic acid which hybridizes under stringent conditions to the sense or antisense nucleic acid sequence of SEQ ID NO:1. In preferred embodiments, the purified nucleic acid is at least 10, more preferably 20, 30, 40, 50 or 100 nucleotides in length. In preferred embodiments,the purified nucleic acid: is useful as a probe or primer; has at least 50%, 60%, 70%, 80%, 90%, 95%, 98%, or 99% homology with a sequence from SEQ ID NO:1; is at least 10, 20, 30, 50, 100, or 200 nucleotides in length; further includes a label group attached thereto. The label group can be, e.g., a radioisotope, a fluorescent compound, an enzyme, and/or an enzyme co-factor.

The invention provides a nucleic acid, e.g., RNA or DNA, encoding a polypeptide of the invention. This includes double stranded nucleic acids as well as coding and antisense single strands.

In another aspect, the invention includes: a vector including a nucleic acid which encodes a Nmi polypeptide; a host cell transfected with the vector; and a method of producing a recombinant Nmi polypeptide; including culturing the cell, e.g., in a cell culture medium, and isolating the Nmi polypeptide, e.g. from the cell or from the cell culture medium.

In another aspect, the invention features a cell or purified preparation of cells which include a Nmi transgene, or which otherwise misexpress a Nmi gene. The cell preparation can consist of human or non human cells, e.g., rodent cells, e.g., mouse or rat cells, rabbit cells, or pig cells. In preferred embodiments, the cell or cells include a Nmi transgene, e.g., a heterologous form of a Nmi gene, e.g., a gene derived from humans (in the case of a non-human cell). The Nmi transgene can be misexpressed, e.g., overexpressed or underexpressed. In other preferred embodiments, the cell or cells include a gene which misexpress an endogenous Nmi gene, e.g., a gene the expression of which is disrupted, e.g., a knockout. Such cells can serve as a model for studying disorders which are related to mutated or mis-expressed Nmi alleles or for use in drug screening.

In another aspect, the invention features a transgenic Nmi animal, e.g., a rodent, e.g., a mouse or a rat, a rabbit, or a pig. In preferred embodiments, the transgenic animal includes (and preferably express) a heterologous form of a Nmi gene, e.g., a gene derived from humans. In other preferred embodiments, the animal has an endogenous Nmi gene which is misexpressed, e.g., a knockout. Such a transgenic animal can serve as a model for studying disorders which are related to mutated or mis-expressed Nmi alleles or for use in drug screening.

For example, the invention includes a method of evaluating the effect of the expression or misexpression of a Nmi gene, on any of: a parameter related to cell growth or regulation of the cell cycle. The method includes: providing a transgenic animal having a Nmi transgene, or which otherwise misexpresses a Nmi gene; contacting the animal with an agent; and evaluating the effect of the transgene on a parameter related to cell growth or the regulation of the cell cycle (e.g., by comparing the value of the parameter for a transgenic animal with the value for a control, e.g., a wild type animal).

In another aspect, the invention provides, a method of determining if a subject mammal, e.g., a primate, e.g., a human, is at risk for a disorder related to a lesion in or the misexpression of a Nmi gene. Such disorders include, e.g., those characterized by abnormal or unwanted cell proliferation, e.g., cancer, e.g., leukemia, e.g., promyelocytic leukemia, chronic myelogenous leukemia, or lymphoblastic leukemia, lymphoma, e.g., Burkitts lymphoma, carcinoma, e.g., colorectal adenocarcinoma or lung carcinoma, colorectal cancer, melanoma, neuroblastoma, lung cancer, e.g., small cell lung cancer, or a disorder of the brain, e.g., mental retardation. The method includes detecting, in a tissue of the subject the mis-expression, or a mutation which results in misexpression, of a gene encoding a protein represented by SEQ ID NO:1 on SEQ ID NO:16. preferred embodiments: detecting the mutation or misexpression includes ascertaining the existence of at least one of: a mutation in the gene or in a region which controls expression of the gene; an alteration in the level of a messenger RNA transcript of the gene; the presence of a non-wild type splicing pattern of a messenger RNA transcript of the gene; or a non-wild type level of the protein.

In another aspect, the invention features, a method of determining if a subject mammal, e.g., a primate, e.g., a human, is at risk for a disorder, e.g., a disorder related to a lesion in, or the misexpression of, an Nmi gene. Such disorders include, e.g., those characterized by abnormal or unwanted cell proliferation, e g., cancer, e.g., leukemia, e.g., promyelocytic leukemia, chronic myelogenous leukemia, or lymphoblastic leukemia, lymphoma, e.g., Burkitts lymphoma, carcinoma, e.g., colorectal adenocarcinoma or lung carcinoma, colorectal cancer, melanoma, neuroblastoma, lung cancer, e.g., small cell lung cancer, or a disorder of the brain, e.g., mental retardation. The method includes detecting, in a tissue of the subject, the presence or absence of a mutation in a Nmi gene, or a homolog thereof. In preferred embodiments: detecting the mutation includes ascertaining the existence of at least one of: a deletion of one or more nucleotides from the gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 or naturally occurring mutants thereof or 5' or 3' flanking sequences naturally associated with a Nmi gene; (ii) contacting the probe/primer with nucleic acid of the tissue; and detecting, e.g., by hybridization, e.g., in situ hybridization, of the probe/primer to the nucleic acid, the presence or absence of the genetic lesion.

In another aspect, the invention provides, a method of determining if a subject mammal, e.g., a primate, e.g., a human, is at risk for a disorder related to a Nmi gene. Such disorders include, e.g., those characterized by abnormal or unwanted cell proliferation, e.g., cancer, e.g., cancer, e.g., leukemia, e.g., promyelocytic leukemia, chronic myelogenous leukemia, or lymphoblastic leukemia, lymphoma, e.g., Burkitts lymphoma, carcinoma, e.g., colorectal adenocarcinoma or lung carcinoma, colorectal cancer, melanoma, neuroblastoma, lung cancer, e.g., small cell lung cancer, or a disorder of the brain, e.g., mental retardation. The method includes detecting, in a tissue of the subject, a non-wild type level of a Nmi RNA or polypeptide.

Diagnostic methods disclosed herein can be performed prenatally, on infants, children, or adults.

The invention includes methods of determining the stage of a cancer, or the degree of resistance to a chemotherapy agent. Advanced stage, or resistance to chemotherapy, is correlated with amplification or overexpression of Nmi.

Thus, in another aspect, the invention provides, a method of determining if a subject mammal, e.g., a primate, e.g., a human, at risk for a disorder related to a Nmi gene, is resistant to chemotherapy. Such disorders include, e.g., those characterized by abnormal or unwanted cell proliferation, e.g., cancer, e.g., cancer, e.g., leukemia, e.g., promyelocytic leukemia, chronic myelogenous leukemia, or lymphoblastic leukemia, lymphoma, e.g., Burkitts lymphoma, carcinoma, e.g., colorectal adenocarcinoma or lung carcinoma, colorectal cancer, melanoma, neuroblastoma, lung cancer, e.g., small cell lung cancer, or a disorder of the brain. The method includes detecting, in a tissue of the subject, amplification of the Nmi gene or an a non-wild type, e.g., elevated, level of a Nmi RNA or polypeptide. Amplification of the Nmi gene or elevated (e.g., as compared to normal or control tissue) levels of Nmi mRNA or polypeptide is indicative of resistance to chemotherapy. In preferred embodiments: the subject has been administered a chemotherapeutic agent prior to detection of Nmi gene, RNA, or polypeptide levels; the subject has been administered a chemotherapeutic agent prior to detection of Nmi gene, RNA, or polypeptide levels and is administered a second different treatment modality, e.g., a different chemotherapeutic agent, or a non-chemotherapeutic treatment modality, after the detection of Nmi gene, RNA, or polypeptide levels; the subject is administered a non-chemotherapeutic treatment modality, after the detection of Nmi gene, RNA, or polypeptide levels.

In another aspect, the invention features, a method of evaluating a compound for the ability to interact with an Nmi polypeptide. The interaction can be any interaction between the compound and Nmi, e.g., binding of the compound with an Nmi polypeptide, alteration of the three dimensional structure of the compound or the Nmi polypeptide, or covalent or non-covalent modification of the compound or the Nmi polypeptide. The method includes: contacting the compound with the Nmi polypeptide; and evaluating the ability of the compound and the Nmi polypeptide to interact. This method can be performed in vitro, e.g., in a cell free system, or in vivo, e.g., in a two-hybrid interaction trap assay. This method can be used to identify naturally occurring or synthetic molecules which interact with Nmi polypeptides, and is useful for evaluating compounds for the ability to inhibit or mimic an Nmi.

In preferred embodiments, the compound is: a ligand of an Nmi polypeptide; a myc polypeptide, e.g., an N-myc, C-myc, Max, or Mxil protein; a protein having a basic-leucine zipper region, e.g., a fos protein; a daughterless protein; a transcription factor, e.g., a zip transcription factor; a polypeptide which includes any of a bHLH-Zip region, a bHLH region, a zip region; a polypeptide which binds DNA or RNA, e.g., a polypeptide which binds DNA or RNA is a sequence specific manner; a polypeptide which does not include a zinc-finger region. In particularly preferred embodiments the compound is a fragment or an analog of one of the above recited polypeptides.

The method is particularly useful for identifying compounds, e.g., fragments or analogs of Nmi ligands, which bind Nmi and which, e.g., are agonists or antagonists of a Nmi ligand.

In another aspect, the invention features, a method of evaluating a fragment or analog of the Nmi protein for a biological activity or for the ability to interact with a compound. The interaction can be any interaction between the compound and the fragment or analog, e.g., binding of the compound with the Nmi fragment or analog, alteration of the three dimensional structure of the compound or the Nmi fragment or analog, or covalent or non-covalent modification of the compound or the Nmi fragment or analog. The method includes: contacting the fragment or analog of the Nmi protein with the compound; and evaluating the ability of the compound and the Nmi fragment or analog to interact. This method can be performed in vitro, e.g., in a cell free system, or in vivo, e.g., in a two-hybrid interaction trap assay.

In preferred embodiments, the compound is: a ligand of an Nmi polypeptide; a myc polypeptide, e.g., an N-myc, C-myc, Max, Mxil, or protein; ; a protein having a basic-leucine zipper region, e.g., a fos protein; a daughterless protein; a transcription factor, e.g., a zip transcription factor; a polypeptide which includes any of a bHLH-Zip region, a bHLH region, a zip region, a polypeptide which binds DNA or RNA, e.g., a polypeptide which binds DNA or RNA is a sequence specific manner; a polypeptide which does not include a zinc-finger region. In particularly preferred embodiments the compound is a fragment or an analog, e.g., an Nmi-interacting fragment or analog, of one of the above recited polypeptides.

The method is particularly useful for identifying fragments or analogs of Nmi which have biological activity or which can bind a candidate compound. This method is useful for identifying fragments or analogs of Nmi which are agonists or antagonists of Nmi.

In yet another aspect, the invention features a method for evaluating a first compound, for the ability to modulate an interaction of an Nmi polypeptide with a second compound, e.g., a myc protein. The first compound can be, e.g., an inhibitor candidate, e.g., a fragment or analog of an Nmi-ligand e.g., a fragment of a myc protein. The method includes the steps of:

(i) providing a reaction mixture which includes the first compound (e.g., an inhibitor candidate), an Nmi polypeptide, and the second compound (e.g., a myc polypeptide), preferably under conditions wherein in the absence of the first compound, the Nmi polypeptide and the second compound, interact; and (ii) detecting an interaction between the Nmi polypeptide and the second compound, e.g., detecting the formation (or dissolution) of a complex which includes the second compound, and the Nmi polypeptide. A change, e.g., a decrease or increase in an interaction, e.g., in the formation of the complex in the presence of the first compound (relative to what is seen in the absence of the first compound), being indicative of a modulation.

The interaction can be any interaction between the second compound and Nmi, e.g., binding of the second compound with an Nmi polypeptide, alteration of the three dimensional structure of the compound or the Nmi polypeptide, or covalent or non-covalent modification of the second compound or the Nmi polypeptide.

In preferred embodiments, the one or more of the first compound (e.g., an inhibitor candidate), the Nmi polypeptide, and the second compound (e.g., a myc polypeptide), is a purified preparation.

In preferred embodiments, the second compound can be: a ligand of an Nmi polypeptide; a myc polypeptide, e.g., an N-myc, C-myc, Max, Mxii, or protein; a protein having a basic-leucine zipper region, e.g., a fos protein; a daughterless protein; a transcription factor, e.g., a zip transcription factor; a polypeptide which includes any of a bHLH-Zip region, a zip region; a bHLH region, a polypeptide which binds DNA or RNA, e.g., a polypeptide which binds DNA or RNA is a sequence specific manner; a polypeptide which does not include a zinc-finger region. In particularly preferred embodiments the compound is a fragment or an analog, e.g., an Nmi-interacting fragment or analog, of one of the above recited polypeptides.

The method can be performed in a cell-free system, e.g., a cell lysate or a reconstituted protein mixture. The Nmi polypeptide, and the second compound can be expressed in a cell, and the cell contacted with the first compound, e.g. in an interaction trap assay (e.g., a two-hybrid assay).

In yet another aspect, the invention features a two-phase method (e.g., a method having an in vitro, e.g., a cell free system, and an in vivo phase) for evaluating a compound, for the ability to modulate an interaction of an Nmi polypeptide, with a second compound.

The method includes steps in vitro evaluation method described herein, e.g., (i) and (ii) of the method described immediately above performed in vitro, and further includes: (iii) determining if the compound modulates the interaction in vitro, e.g., in a cell free system, and if so; (iv) administering the compound to a cell or animal; and optionally,(v) evaluating the in vivo effect of the compound on an interaction of an Nmi polypeptide, with a second compound, e.g., by the effect on cell growth or the regulation of the cell cycle, or by the effect on the expression of a reporter gene.

In another aspect, the invention features a method for evaluating a compound, e.g., for the ability to modulate, e.g., to inhibit or promote, a Nmi polypeptide-mediated phenomenon, e.g., an aspect of intracellular signaling, the cell cycle, or cell proliferation, or to evaluate test compounds for use as therapeutic agents. The method includes: contacting the test compound with a cell. or a cell free system, which includes a reporter gene functionally linked to a Nmi; polypeptide regulatory sequence, and detecting the modulation of the expression of the reporter gene, modulation of the expression of the reporter gene being correlated to efficacy of the compound.

In another aspect, the invention features a two-phase method (e.g., a method having a primary in vitro and a secondary in vivo phase) for evaluating a treatment. The method can be used to evaluate a treatment for the ability to modulate, e.g., to inhibit or promote, a Nmi polypeptide-mediated phenomenon, e. g., progression through the cell cycle or cell proliferation, or to evaluate test compounds for use as therapeutic agents. The method includes: (i) an in vitro phase in which the test compound is contacted with a cell, or a cell free system, which includes a reporter gene functionally linked to a Nmi polypeptide regulatory sequence, and detecting the modulation of the expression of the reporter gene and (ii) if the test compound modulates the expression, administering the test compound to an animal, and evaluating the in vivo effects of the compound on a parameter related to an Nmi-related parameter, e.g., progression through the cell cycle or cell proliferation, intracellular signaling, In another aspect, the invention features, a method of evaluating a compound for the ability to bind a nucleic acid encoding a Nmi polypeptide regulatory sequence. The method includes: contacting the compound with the nucleic acid; and evaluating ability of the compound to form a complex with the nucleic acid.

In another aspect, the invention features a method of making a fragment or analog of an Nmi polypeptide, e.g., a fragment or analog having a biological activity of a naturally occurring Nmi polypeptide. The method includes: altering the sequence, e.g., by substitution or deletion of one or more residues, of an Nmi polypeptide, e.g., altering the sequence of a non-conserved region, or a domain or region referred to herein, and, optionally testing the altered polypeptide for the desired activity.

In another aspect, the invention features, a method of evaluating a treatment for the ability to modulate the growth or regulation of the cell cycle of a cell which has a greater than wild type level of Nmi activity. The method is useful in assessing the usefulness of a particular treatment for disorders which are mediated by Nmi activity. The method includes: administering the treatment to a cell which over expresses Nmi, e,g., a cell which has been genetically engineered to over express the Nmi gene, e.g., a cell which has one or more additional copies of an Nmi encoding sequence, or an Nmi encoding sequence coupled to a control region which results in over expression (as compared to wild type for that cell); and determining if there is an effect on cell growth. The cell can be e.g., a microbial cell, e.g., a yeast cell, or an animal cell e.g., a mammalian cell, e.g., a rodent, e.g., rat or mouse, or a human cell. The cell can, e.g., be a cultured cell or a cell derived from a transgenic animal.

In another aspect, the invention features a method of treating a mammal, e.g., a human, at risk for a disorder, e.g., a disorder characterized by aberrant or unwanted level of Nmi activity. Such disorders include, e.g., those characterized by abnormal or unwanted cell proliferation, e. g., cancer, e.g., leukemia, e.g., promyelocytic leukemia, chronic myelogenous leukemia, or lymphoblastic leukemia, lymphoma, e.g., Burkitts lymphoma, carcinoma, e.g., colorectal adenocarcinoma or lung carcinoma, colorectal cancer, melanoma, neuroblastoma, or lung cancer, e.g., small cell lung cancer. The method includes reducing the activity of Nmi, e.g., by administering to the mammal a therapeutically effective amount of any of:

a Nmi polypeptide encoding nucleic acid, wherein the encoded polypeptide is an antagonist of Nmi, e.g., it inhibits the interaction of Nmi with an Nmi ligand;

a Nmi polypeptide, wherein the polypeptide is an antagonist of Nmi, e.g., it inhibits the interaction of Nmi with an Nmi ligand;

an anti-Nmi antibody, e.g., an intrabody, which, e.g., inhibits the interaction of Nmi with an Nmi ligand; or an antisense molecule, or a nucleic acid which encodes an antisense molecule, which inhibits the expression or activity of Nmi.

In preferred embodiments,the method includes further reducing the activity of a Nmi ligand, e.g., a myc gene product, e.g., by administering to the mammal a therapeutically effective amount of any of:

a Nmi ligand encoding nucleic acid, wherein the encoded polypeptide is an antagonist of the Nmi ligand, e.g., it inhibits the interaction of Nmi with a Nmi ligand;

a Nmi ligand fragment or analog, wherein the fragment of analog is an antagonist of the ligand, e.g., it inhibits the interaction of Nmi with an Nmi ligand;

an anti-Nmi ligand antibody, e,g., an intrabody, which, e.g., inhibits the interaction of Nmi with a Nmi ligand; or an antisense molecule, or a nucleic acid which encodes an antisense molecule, which inhibits the expression or activity of a Nmi ligand.

In another aspect, the invention features a method of treating a mammal, e.g., a human, at risk for a disorder, e.g., a disorder characterized by an insufficient level of Nmi activity. Such disorders include disorders of a tissue in which Nmi is not normally expressed, e.g., the brain. Such disorders include, e.g., mental retardation, and disorders characterized by unwanted cell proliferation, e.g., cancers of the brain or peripheral nervous system, and melanoma. The method includes increasing the activity of Nmi, e.g., by administering to the mammal a therapeutically effective amount of any of:

a Nmi polypeptide encoding nucleic acid; or a Nmi polypeptide.

In another aspect, the invention features a method of treating a mammal, e.g., a human, at risk for a disorder, e.g., a disorder characterized by aberrant or unwanted level of Nmi activity. The method includes administering to the mammal a treatment, e.g., a therapeutically effective amount a Nmi polypeptide.

In another aspect, the invention features, a human cell, e.g., a hematopoietic stem cell, transformed with a nucleic acid which encodes a Nmi polypeptide, or transformed with a nucleic acid which encodes an Nmi antisense molecule.

Nmi polypeptides and nucleic acids are useful for: identifying cells which express a Nmi gene; the production of peptides or antisense molecules which can modulate the cell cycle or cell proliferation, in vivo or in vitro; for the generation of anti-Nmi antibodies, which are useful for identifying cells which express Nmi or for evaluating levels of Nmi expression; for producing Nmi binding molecules; and for therapeutic and diagnostic applications.

Omi Gene

The present invention is based, in part, on the discovery of the gene which encodes the mammalian serine protease, Omi. Accordingly, the present invention features a purified or isolated preparation or a recombinant preparation of Omi, or an Omi polypeptide. An Omi polypeptide can be a full length sequence or a fragment of the full length of Omi.

In a preferred embodiment, Omi has at least about 60% to about 70%, more preferably at least about 80%, even more preferably at least about 90% to about 95%, and most preferably at least about 99% sequence identity with human Omi, e.g., the human Omi of SEQ ID NO:5. Omi can be identical to a human Omi sequence, e.g., that of SEQ ID NO:5. In another embodiment, Omi is encoded by a nucleic acid molecule which hybridizes under stringent conditions to a nucleic acid molecule of the nucleic acid sequence shown in SEQ ID NO:4. In addition, Omi can have substantially the same electrophoretic mobility as human Omi. Omi has a predicted molecular weight of about 57 kDa. Yet another preferred embodiment of the invention features an Omi which is reactive with an Omi-specific antibody, e.g., an antibody which binds to the epitope recognized by a monoclonal antibody, or a polyclonal antibody. Antibodies against Omi can be made by methods exemplified herein.

In another preferred embodiment, Omi is expressed by a recombinant cell, e.g., a bacterial cell, a cultured cell (e.g., a cultured eukaryotic cell) or a cell of a non-human transgenic organism, e.g., a transgenic animal or transgenic plant.

Cultured cells can include CHO cells or SF8 cells. Expression of Omi in a transgenic animal can be general or can be under the control of a tissue specific promoter. Preferably, one or more sequences which encode Omi or a fragment thereof are expressed in a preferred cell-type by a tissue specific promoter. Exemplary sequences encoding fragments of Omi include, e.g., a sequence encoding the amino terminal regulatory domain of Omi, e.g., a signal peptidase site, a domain that includes one of more of consensus sequence PRAXXTXXTP (SEQ ID NO:6), where X can be any amino acid residue (triple repeat), a sequence encoding an SH3 binding domain, a sequence encoding a consensus phosphorylation site, e.g., a consensus phosphorylation site for Mxi2 kinase, and/or a carboxy terminal serine protease catalytic domain.

In a preferred embodiment, the recombinant Omi differs from Omi isolated from tissue in one or more of the following: its pattern of glycosylation, myristilation, phosphorylation, or other posttranslational modifications.

In a preferred embodiment, the recombinant Omi preparation is free of other placental proteins, pancreatic proteins, tumor proteins, or other human proteins.

In a preferred embodiment, the recombinant Omi preparation contains at least 1, 10, or 100 μg of Omi, or an Omi polypeptide.

In a preferred embodiment, the recombinant Omi preparation contains at least 1, 10, or 100 mg of Omi, or an Omi polypeptide.

In a preferred embodiment, the Omi polypeptide has one or more of the following biological activities: 1) it is phosphorylated by the Mxi2 kinase; 2) it interacts with, e.g., binds to, the Mxi2 kinase; 3) it interacts with, e.g., binds to, a target, e.g., a serine protease inhibitor; 4) it proteolytically cleaves a substrate, e.g., a protein; 5) it is a serine protease; 6) it is a member of the MAP kinase cell signalling pathway; 7) it is involved in mammalian pathologies, e.g., ischemia of the kidney, the heart, or the forebrain; inflammatory response; septic shock; and 8) it modulates a cellular response to stress.

In other preferred embodiments: the Omi polypeptide includes an amino acid sequence with at least 60%, 80%, 90%, 95%, 98%, or 99% sequence identity to an amino acid sequence from SEQ ID NO:5; the Omi polypeptide includes an amino acid sequence essentially the same as the amino acid sequence in SEQ ID NO:5; the Omi polypeptide is at least 5, 10, 20, 50, 100, or 150, 200, 250 amino acids in length; the Omi polypeptide includes at least 5, preferably at least 10, more preferably at least 20, most preferably at least 50, 100, or 150, 200, 250 contiguous amino acids from SEQ ID NO:5; the Omi polypeptide is either, an agonist or an antagonist, of a biological activity of naturally occurring Omi; the Omi polypeptide is a vertebrate, e.g., a mammalian, e.g. a primate, e.g., a human, Omi polypeptide.

In preferred embodiments, the Omi polypeptide is encoded by the nucleic acid in SEQ ID NO:4, or by a nucleic acid having at least about 50%, more preferably at least about 60% to about 70%, and most preferably at least about 75% sequence identity with the nucleic acid from SEQ ID NO:4.

In preferred embodiments, the Omi polypeptide includes an amino terminal regulatory domain (RD) which includes a putative signal peptidase cleavage site, a triple repeat sequence of consensus sequence PRAXXTXXTP (SEQ ID NO:6), where X can be any amino acid residue), an SH3 domain (PPPASPR, SEQ ID NO:7), a potential consensus Mxi2/p38 kinase phosphorylation site (SPRS, SEQ ID NO:8), and a carboxy terminal serine protease catalytic domain.

In preferred embodiments, the Omi polypeptide includes at least one putative signal peptidase cleavage site. Generally, the domain is about 2 residues in length, and preferably, has about 50, 60, 70, 80, 90, or 95% sequence identity with the protein .sequence shown in SEQ ID NO:5 (between amino acid residues 26 and 27).

In preferred embodiments, the Omi polypeptide includes a consensus amino acid sequence P-R-A-X-X-T-X-X-T-P (SEQ ID NO:6), where X can be any amino acid. In preferred embodiments, the Omi polypeptide includes at least one consensus sequence, more preferably 2 consensus sequences, and most preferably about 3 consensus sequences, e.g., a triple repeat sequence. Generally, the consensus sequence is about 10 residues in length, and preferably, has about 70, 80, 90, or 95% sequence identity with the protein sequence shown in SEQ ID NO:5 (amino acid residues 117–126, 139–148 and 150–159).

In preferred embodiments, the Omi polypeptide includes at least one SH3 binding domain (e.g., a domain having the consensus sequence PPPASPR, SEQ ID NO:7). Generally, the domain is about 7 residues in length, and preferably, has about 70, 80, 90, or 95% sequence identity with the protein sequence shown in SEQ ID NO:5 (amino acid residues 209–215). In other embodiments, the SH3 binding domain overlaps with one or both the RD and the putative Mxi2/p38 kinase consensus phosphorylation site.

In preferred embodiments, the Omi polypeptide includes at least one potential consensus phosphorylation site for Mxi2/p38 kinase (e.g., a domain having the consenus sequence SPRS, SEQ ID NO:8). Generally, the phosphorylation site is about 4 residues in length, and preferably, has about 70, 80, 90, or 95% sequence identity with the protein sequence shown in SEQ ID NO:5 (amino acid residues 213–216).

In preferred embodiments, the Omi polypeptide includes a serine protease catalytic domain similar to L56 and HtrA serine protease catalytic domains. Generally, the serine protease catalytic domain is about 312 residues, and preferably has about 50, 60, 70, 80, 90, or 95% sequence identity with the protein sequence shown in SEQ ID NO:5 (amino acid residues 217–529).

In a preferred embodiment, the Omi polypeptide differs in amino acid sequence at up to 1, 2, 3, 5, or 10 residues, from a sequence in SEQ ID NO:5. In other preferred embodiments, the Omi polypeptide differs in amino acid sequence at up to 1, 2, 3, 5, or 10% of the residues from a sequence in SEQ ID NO:5. Preferably, the differences are such that: the Omi polypeptide exhibits an Omi biological activity, e.g., the Omi polypeptide retains a biological activity of a naturally occurring Omi. A position differs if it is a different amino acid, is deleted, or is an insertion, as compared to the sequence in SEQ ID NO:5.

In preferred embodiments, the Omi polypeptide includes an Omi sequence described herein as well as other N-terminal, and/or a C-terminal amino acid sequence.

In preferred embodiments, the Omi polypeptide includes all or a fragment of an amino acid sequence from SEQ ID NO:5, fused, in reading frame, to additional amino acid residues, preferably to residues encoded by genomic DNA 5' to the genomic DNA which encodes a sequence from SEQ ID NO:5.

In yet other preferred embodiments, the Omi polypeptide is a recombinant fusion protein having a first Omi portion and a second polypeptide portion, e.g., a second polypeptide portion having an amino acid sequence unrelated to Omi. The second polypeptide portion can be, e.g., any of glutathione-S-transferase, a DNA binding domain, or a polymerase activating domain. In a preferred embodiment, the fusion protein can be used in a two-hybrid assay.

For example, a first Omi portion, e.g., an Omi portion containing a serine protease catalytic domain, e.g., amino acids 209 to end encoded by the last exon, can be fused to a DNA binding domain. In a two hybrid assay, the first Omi portion is co-expressed in a cell with a second polypeptide portion containing a transcription activation domain fused to an expression library, e.g., a HeLa cervical carcinoma expression library.

In a preferred embodiment, the Omi polypeptide includes: amino acid residues 1–116, or a sequence that has 80, 90, 95, 99% sequence identity with 1–116, of SEQ ID NO:5; amino acid residues 117–126, or a sequence that has 80, 90, 95, 99% sequence identity with 117–126, of SEQ ID NO:5; amino acid residues 139–148, or a sequence that has 80, 90, 95, 99% sequence identity with 139–148, of SEQ ID NO:5; amino acid residues 150–159, or a sequence has that 80, 90, 95, 99% sequence identity with 150–159, of SEQ ID NO:5; amino acid residues 209–215, or a sequence that has 80, 90, 95, 99% sequence identity with 209–215, of SEQ ID NO:5; amino acid residues 213–216, or a sequence that has 80, 90, 95, 99% sequence identity with amino acids 213–216, of SEQ ID NO:5; and/or amino acid residues 217–529, or a sequence has 80, 90, 95, 99% sequence identity with amino acids 217–529, of SEQ ID NO:5.

In preferred embodiments, the Omi polypeptide has an antagonistic activity or agonistic activity, and is capable of: modulating a cellular response to stress.

In a preferred embodiment, the Omi polypeptide is a fragment of a naturally occurring Omi which inhibits a cellular response to stress.

In another aspect, the invention features an Omi polypeptide which is a fragment of a full length Omi polypeptide, e.g., a fragment of a naturally occurring Omi polypeptide, e.g., the polypeptide encoded by the nucleic acid of SEQ ID NO:4.

In preferred embodiments: the fragment is at least 5, 10, 20, 50, 100, or 150 amino acids in length; the fragment is equal to or less than 200, 150, 100, 50 amino acid residues in length; the fragment has a biological activity of a naturally occurring Omi; the fragment is either, an agonist or an antagonist, of a biological activity of a naturally occurring Omi; the fragment can inhibit, e.g., competitively or non competitively inhibit, the binding of Omi to an Omi-interacting protein, e.g., an Mxi2 protein.

In preferred embodiments, the fragment it has at least 60, and more preferably at least 70, 80, 90, 95, 99, or 100% sequence identity with the corresponding amino acid sequence of SEQ ID NO:5.

In preferred embodiments, the fragment is a fragment of a vertebrate, e.g., a mammalian, e.g. a primate, e.g., a human, Omi polypeptide.

In preferred embodiments, the Omi fragment includes an amino terminal regulatory domain, which has at least 50, 60, 70, 80, 90, 95, 99 or 100% sequence identity with residues 1–216 of the Omi sequence of SEQ ID NO:5.

In preferred embodiments, the Omi fragment includes a signal peptidase site, which has at least 50, 60, 70, 80, 90, 95, 99 or 100% sequence identity with residues 26–27 of the Omi sequence of SEQ ID NO:5.

In preferred embodiments, the Omi fragment includes includes a consensus amino acid sequence P-R-A-X-X-T-X-X-T-P (SEQ ID NO:6), where X can be any amino acid. In preferred embodiments, the Omi fragment includes at least one consensus sequence, more preferably 2 consensus sequences, and most preferably about 3 consensus sequences (e.g., a triple repeat sequence) having at least 50, 60, 70, 80, 90, 95, 99 or 100% sequence identity with residues 117–126, 139–148 and 150–159 of the Omi sequence of SEQ ID NO:5.

In preferred embodiments, the Omi fragment includes an SH3 binding domain, which has at least 50, 60, 70, 80, 90, 95, 99 or 100% sequence identity with residues 209–215 of the Omi sequence of SEQ ID NO:5.

In preferred embodiments, the Omi fragment includes a potential consensus Mxi2/p38 kinase phosphorylation site, which has at least 50, 60, 70, 80, 90, 95, 99 or 100% sequence identity with residues 213–216 of the Omi sequence of SEQ ID NO:5.

In preferred embodiments, the Omi fragment includes a carboxy terminal serine protease catalytic domain, which has at least 50, 60, 70, 80, 90, 95, 99 or 100% sequence identity with residues 217–529 of the Omi sequence of SEQ ID NO:5.

In preferred embodiments, the fragment can inhibit an interaction, e.g., binding, between Omi and an Omi-interacting protein.

In a preferred embodiment, the fragment differs in amino acid sequence at up to 1, 2, 3, 5, or 10 residues, from the corresponding residues in SEQ ID NO:5. In other preferred embodiments, the fragment differs in amino acid sequence at up to 1, 2, 3, 5, or 10% of the residues from the corresponding residues in SEQ ID NO:5. In preferred embodiments, the differences are such that the fragment exhibits an Omi biological activity. In other preferred embodiments, the differences are such that the fragment does not have Omi biological activity. In preferred embodiments, one or more, or all of the differences are conservative amino acid changes. In other preferred embodiments, one or more, or all of the differences are other than conservative amino acid changes.

In a preferred embodiment, the Omi polypeptide, or fragment thereof, differs in amino acid sequence from the amino acid sequence encoded by the EST fragments shown in Table 1 herein.

By "differs" is meant an amino acid sequence other than the amino acid sequence encoded by those EST fragments shown in Table 1, e.g., it differs from the amino acid sequence encoded by those EST fragments shown in Table 1 by at least one amino acid residue, e.g., the Omi polypeptide is at least one amino acid residue shorter, one amino acid residue longer, differs in sequence at least at one position, has a different N terminus, or has a different C terminus, as compared with the amino acid sequence encoded by those EST fragments shown in Table 1.

Polypeptides of the invention include those which arise as a result of the existence of multiple genes, alternative transcription events, alternative RNA splicing events, and alternative translational and postranslational events. The Omi polypeptide can be expressed in systems, e.g., cultured cells, which result in substantially the same postranslational modifications present when expressed Omi is expressed in a native cell, or in systems which result in the omission of postranslational modifications present when expressed in a native cell.

The invention includes an immunogen which includes an Omi polypeptide in an immunogenic preparation, the immunogen being capable of eliciting an immune response specific for the Omi polypeptide, e.g., a humoral response, an antibody response, or a cellular response. In preferred embodiments, the immunogen comprises an antigenic determinant, e.g., a unique determinant, from a protein represented by SEQ ID NO:5.

The present invention also includes an antibody preparation specifically reactive with an epitope of the Omi immunogen or generally of an Omi polypeptide, preferably an epitope which consists all or in part of residues from the the amino acid sequence of SEQ ID NO:5, or an epitope, which when bound to an antibody, results in the modulation of a biological activity.

In preferred embodiments,the Omi-like polypeptide, as expressed in the cells in which it is normally expressed or in other eukaryotic cells, has a molecular weight of about 57 kDa as estimated from the nucleic acid sequence SEQ ID NO:1.

In another embodiment, the Omi polypeptide comprises amino acid residues 1–529 of FIG. 4a (SEQ ID NO:5).

In a preferred embodiment, the recombinant Omi polypeptide has one or more of the following characteristics:
  (i) it is approximately 529 amino acids in length;
  (ii) it has the ability to cleave a substrate, e.g., a protein;
  (iii) it binds to Mxi2 in vivo and in vitro;
  (iv) it does not bind to p38;
  (v) it has a molecular weight, amino acid composition or other physical characteristic of Omi of SEQ ID NO:5;
  (vi) it has an overall sequence similarity of at least 50%, preferably at least 60%, more preferably at least 70, 80, 90, or 95%, with an Omi polypeptide of SEQ ID NO:5;
  (vii) it is found in all human tissues;
  (viii) it is most abundantly found in the placenta and the pancreas;
  (ix) it is found in tumor cell lines, e.g., promyelocytic leukemia HL-60 cells, chronic myelogenous leukemia K-562, Burkitt's lymphoma Raji,and human colorectal carcinoma SW480 cell lines;
  (x) it is translated from at least two species of mRNA, one abundant transcript is about 2.1 kb, and another less abundant transcript of about 4.5 kb;
  (xi) it is encoded by a gene localized on the human chromosome 2p12;
  (xii) it has at least one signal peptidase site which is preferably about 70%, 80%, 90% or 95% identical to amino acid residues 26–27 of SEQ ID NO:5;
  (xiii) it has a domain that includes a consensus amino acid sequence P-R-A-X-X-T-X-X-T-P (SEQ ID NO:6), more preferably 2, and most preferably about 3 consensus sequences (e.g., a triple repeat sequence), each of which is preferably about 70%, 80%, 90%, or 95% identical to amino acid residues 117–126, 139–148 and 150–159 of SEQ ID NO:5;
  (xiv) it has at least one SH3 binding domain which is preferably about 70%, 80%, 90% or 95% identical to amino acid residues 209–215 of SEQ ID NO:5;
  (xv) it has a putative consensus phosphorylation site for Mxi2/p38 kinase kinase which is preferably about 70%, 80%, 90% or 95% identical to amino acid residues 213–216 of SEQ ID NO:5; and
  (xvi) it has a carboxy terminal serine protease catalytic domain containing at least one site of serine protease activity which is preferably about 70%, 80%, 90% or 95% identical to amino acid residues 181–529 of SEQ ID NO:5.

Also included in the invention is a composition which includes an Omi polypeptide (or a nucleic acid which encodes it) and one or more additional components, e.g., a carrier, diluent, or solvent. The additional component can be one which renders the composition useful for in vitro and in vivo pharmaceutical or veterinary use.

In another aspect, the invention provides an isolated or substantially pure nucleic acid having or comprising a nucleotide sequence which encodes a polypeptide, the amino acid of which includes, or is, the sequence of an Omi polypeptide.

In preferred embodiments, the encoded Omi polypeptide has one or more of the following properties:
  (i) it is approximately 529 amino acids in length;
  (ii) it has the ability to cleave a substrate, e.g., a protein;
  (iii) it binds to Mxi2 in vivo and in vitro;
  (iv) it does not bind to p38;
  (v) it has a molecular weight, amino acid composition or other physical characteristic of Omi of SEQ ID NO:5;
  (vi) it has an overall sequence similarity of at least 50%, preferably at least 60%, more preferably at least 70, 80, 90, or 95%, with an Omi polypeptide of SEQ ID NO:5;
  (vii) it is found in all human tissues;
  (viii) it is most abundantly found in the placenta and the pancreas;
  (ix) it is found in tumor cell lines, e.g., promyelocytic leukemia HL-60 cells, chronic myelogenous leukemia K-562, Burkitt's lymphoma Raji,and human colorectal carcinoma SW480 cell lines;
  (x) it is translated from at least two species of mRNA, one abundant transcript is about 2.1 kb, and another less abundant transcript of about 4.5 kb;
  (xi) it is encoded by a gene localized on the human chromosome 2p12;
  (xii) it has at least one signal peptidase site which is preferably about 70%, 80%, 90% or 95% identical to amino acid residues 26–27 of SEQ ID NO:5;
  (xiii) it has a domain that includes a consensus amino acid sequence P-R-A-X-X-T-X-X-T-P (SEQ ID NO:6), more preferably 2, and most preferably about 3 consensus sequences (e.g., a triple repeat sequence), each of which is preferably about 70%, 80%, 90%, or 95% identical to amino acid residues 117–126, 139–148 and 150–159 of SEQ ID NO:5;
  (xiv) it has at least one SH3 binding domain which is preferably about 70%, 80%, 90% or 95% identical to amino acid residues 209–215 of SEQ ID NO:5;
  (xv) it has a putative consensus phosphorylation site for Mxi2/p38 kinase kinase which is preferably about 70%, 80%, 90% or 95% identical to amino acid residues 213–216 of SEQ ID NO:5; and
  (xvi) it has a carboxy terminal serine protease catalytic domain containing at least one site of serine protease activity which is preferably about 70%, 80%, 90% or 95% identical to amino acid residues 181–529 of SEQ ID NO:5.

In preferred embodiments, the encoded polypeptide has a biological activity, e.g., the polypeptide is either, an agonist or an antagonist, of a biological activity of a naturally occurring Omi.

In preferred embodiments,the encoded polypeptide is a vertebrate, e.g., a mammalian, e.g. a primate, e.g., a human, Omi polypeptide.

In preferred embodiments, the encoded Omi polypeptide includes a signal peptidase site which has at least 60, more preferably at least 70, 80, 90, or 100% sequence identity with at nucleotides 325–326 of SEQ ID NO:4 (or residues 26–27 of SEQ ID NO:5).

In preferred embodiments, the encoded Omi polypeptide includes a consensus amino acid sequence P-R-A-X-X-T-X-X-T-P (SEQ ID NO:6), where X can be any amino acid. In preferred embodiments, the Omi polypeptide includes at least one consensus sequence, more preferably 2 consensus sequences, and most preferably about 3 consensus sequences. Preferably, each consensus amino acid sequence is at least 60, more preferably at least 70, 80, 90, or 100% sequence identity with nucleotides 596–624, 661–691 and 695–724 of SEQ ID NO:4 (or residues I 17–126, 139–148 and 150–159 of SEQ ID NO:5).

In preferred embodiments, the encoded Omi polypeptide includes an SH3 binding domain which has at least 60, more preferably at least 70, 80, 90, or 100% sequence identity with nucleotides 872–891 of SEQ ID NO:4 (or residues 209–215 of SEQ ID NO:5).

In preferred embodiments, the encoded Omi polypeptide includes a potential consensus Mxi2/p38 kinase phosphorylation site which has at least 60, more preferably at least 70, 80, 90, or 100% sequence identity with nucleotides 885–891 of SEQ ID NO:4 (or residues 213–216 of SEQ ID NO:5).

In preferred embodiments, the encoded Omi polypeptide includes a carboxy terminal serine protease catalytic domain, which has at least 50, 60, 70, 80, 90, 95, 99 or 100% sequence identity with residues 217–529 of the Omi sequence of SEQ ID NO:5.

In a preferred embodiment, the encoded Omi polypeptide differs in amino acid sequence at up to 1, 2, 3, 5, or 10 residues, from the sequence in SEQ ID NO:5. In other preferred embodiments, the Omi polypeptide differs in amino acid sequence at up to 1, 2, 3, 5, or 10% of the residues from a sequence in SEQ ID NO:5. In preferred embodiments, the differences are such that the Omi polypeptide exhibits an Omi biological activity. In other preferred embodiments the differences are such that the Omi polypeptide does not have Omi biological activity. In preferred embodiments, one or more, or all of the differences are conservative amino acid changes. In other preferred embodiments one or more, or all of the differences are other than conservative amino acid changes.

In preferred embodiments, the encoded Omi polypeptide includes an Omi sequence described herein as well as other N-terminal and/or C-terminal amino acid sequence.

In yet other preferred embodiments, the encoded Omi polypeptide is a recombinant fusion protein having a first Omi portion and a second polypeptide portion, e.g., a second polypeptide portion having an amino acid sequence unrelated to Omi. The second polypeptide portion can be, e.g., any of glutathione-S-transferase, a DNA binding domain, or a polymerase activating domain. In preferred embodiment, the fusion protein can be used in a two-hybrid assay.

In preferred embodiments, there is at least 70, 80, 90, 95, 99, or 100% sequence identity between the encoded Omi polypeptide and the amino acid sequence of SEQ ID NO:5.

The encoded polypeptide can be a fragment of a full length Omi polypeptide, e.g., a fragment of a naturally occurring Omi polypeptide, e.g., the polypeptide encoded in SEQ ID NO:5.

In preferred embodiments, the encoded fragment is at least 5, 10, 20, 50, 100, or 150 amino acids in length; the encoded fragment is equal to or less than 200, 150, 100, 50 amino acid residues in length; the encoded fragment has a biological activity of a naturally occurring Omi; the encoded fragment is either, an agonist or an antagonist, of a biological activity of a naturally occurring Omi; the encoded fragment can inhibit, e.g., competitively or non competitively inhibit, the binding of Omi to an Omi interacting protein, e.g., Mxi2.

In preferred embodiments, the encoded fragment it has at least 60, and more preferably at least 70, 80, 90, 95, 99, or 100% sequence identity with the corresponding amino acid sequence of SEQ ID NO:5.

In preferred embodiments, the encoded fragment is a fragment of a vertebrate, e.g., a mammalian, e.g. a primate, e.g., a human, Omi polypeptide.

In preferred embodiments, the encoded Omi fragment includes a domain, e.g., an amino terminal domain, which has at least 50, 60, 70, 80, 90, 95, 99 or 100% sequence identity with residues 1–216 of the Omi sequence of SEQ ID NO:5.

In preferred embodiments, the encoded Omi fragment includes an amino terminal regulatory domain. The amino terminal regulatory domain is as follows: residues 1–117 of SEQ ID NO:5; residues 26–27 of SEQ ID NO:5; residues 117–126 of SEQ ID NO:5; residues 139–148 of SEQ ID NO:5; residues 150–159 of SEQ ID NO:5; residues 160–208 of SEQ ID NO:5; residues 209–215 of SEQ ID NO:5; and residues 213–216 of SEQ ID NO:5. In preferred embodiments, the encoded fragment includes a region which has at least 50, 60, 70, 80, 90, 95, 99 or 100% sequence identity with an amino terminal regulatory domain. In preferred embodiments, the encoded fragment (which term includes terminal and internal deletions) lacks at least one amino terminal regulatory domain found in naturally occurring Omi.

In preferred embodiments, the encoded Omi fragment includes a carboxy terminal serine protease catalytic domain. The carboxy terminal serine protease catalytic domain is as follows: residues 217–529 of SEQ ID NO:5.

In preferred embodiments, the encoded fragment includes a region which has at least 50, 60, 70, 80, 90, 95, 99 or 100% sequence identity with a carboxy terminal serine protease catalytic domain. In preferred embodiments, the encoded fragment (which term includes terminal and internal deletions) lacks at least one carboxy terminal serine protease catalytic domain found in naturally occurring Omi.

In preferred embodiments, the encoded fragment can inhibit an interaction, e.g., binding, between Omi and an Omi interacting protein. In preferred embodiments, the encoded fragment does not inhibit an interaction, e.g., binding, between Omi and an Omi interacting protein.

In a preferred embodiment, the encoded fragment differs in amino acid sequence at up to 1, 2, 3, 5, or 10 residues, from the corresponding residues in SEQ ID NO:5. In other preferred embodiments, the encoded fragment differs in amino acid sequence at up to 1, 2, 3, 5, or 10% of the residues from the corresponding residues in SEQ ID NO:5. In preferred embodiments, the differences are such that the encoded fragment exhibits an Omi biological activity. In other preferred embodiments the differences are such that the encoded fragment does not have Omi biological activity. In preferred embodiments, one or more, or all of the differences are conservative amino acid changes. In other preferred embodiments one or more, or all of the differences are other than conservative amino acid changes.

In preferred embodiments, the encoded fragment includes an Omi sequence described herein as well as other N-terminal and/or C-terminal amino acid sequence.

In a preferred embodiment, the nucleic acid encodes a polypeptide or fragment thereof which differs by at least one amino acid residue from the amino acid sequence encoded by those EST fragments shown in Table 1.

In a preferred embodiment, the nucleic acid differs by at least one nucleotide from the nucleotide sequence in those EST fragments shown in Table 1.

By "differs" is meant a nucleic acid which has a nucleotide sequence other than a nucleotide sequence which encodes the amino acid sequence encoded by those EST fragments shown in Table 1, e.g., it differs from the sequence encoded by those EST fragments shown in Table 1 by at least one nucleotide, e.g., the Omi encoding nucleic acid is at least one nucleotide shorter, one nucleotide longer, differs in sequence at least one position, has a different 5' terminus, or has a different 3' terminus, as compared with a sequence encoded by those EST fragments shown in Table 1.

In preferred embodiments, the subject Omi nucleic acid includes a transcriptional regulatory sequence, e.g. at least one of a transcriptional promoter or transcriptional enhancer sequence, operably linked to the Omi gene sequence, e.g., to render the Omi gene sequence suitable for use as an expression vector.

A preferred embodiment of the invention features a nucleic acid molecule having a nucleotide sequence at least about 85% sequence identity to a nucleotide sequence of SEQ ID NO:4. In other preferred embodiments, the Omi polypeptide is encoded by a nucleic acid molecule having a nucleotide sequence with at least about 90% to about 95%, and more preferably about 98% to about 99% sequence identity to the nucleotide sequence from SEQ ID NO:4. In another preferred embodiment, the Omi polypeptide is encoded by the nucleic acid molecule of SEQ ID NO:4.

In yet a further preferred embodiment, the nucleic acid which encodes an Omi polypeptide of the invention, hybridizes under stringent conditions to a nucleic acid probe corresponding to at least 12 consecutive nucleotides of SEQ ID NO:4. In preferred embodiments, the purified nucleic acid is at least 10, more preferably 20, 30, 40, 50 or 100 nucleotides in length.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:4, or naturally occurring mutants thereof. In preferred embodiments,the purified nucleic acid: is useful as a probe or primer; has at least 50%, 60%, 70%, 80%, 90%, 95%, 98%, or 99% homology with a sequence from SEQ ID NO:4; is at least 10, 20, 30, 50, 100, or 200 nucleotides in length. In preferred embodiments, the probe or primer further includes a label group attached thereto. The label group can be, e.g., a radioisotope, a fluorescent compound, an enzyme, and/or an enzyme co-factor.

The invention involves nucleic acids, e.g., RNA or DNA, encoding an Omi polypeptide of the invention. This includes double stranded nucleic acids as well as coding and antisense single strands.

In another aspect, the invention features a cell or purified preparation of cells which include an Omi transgene, or which otherwise misexpress an Omi gene. The cell preparation can consist of human or non human cells, e.g., rodent cells, e.g., mouse or rat cells, rabbit cells, or pig cells. In preferred embodiments, the cell or cells include an Omi transgene, e.g., a heterologous form of an Omi gene, e.g., a gene derived from humans (in the case of a non-human cell). The Omi transgene can be misexpressed, e.g., overexpressed or underexpressed. In other preferred embodiments, the cell or cells include a gene which misexpress an endogenous Omi gene, e.g., a gene the expression of which is disrupted, e.g., a knockout. Such cells can serve as a model for studying disorders which are related to mutated or mis-expressed Omi alleles or for use in drug screening.

In another aspect, the invention features a transgenic Omi animal, e.g., a rodent, e.g., a mouse or a rat, a rabbit, a pig, a goat, or a cow. In preferred embodiments, the transgenic animal includes (and preferably express) a heterologous form of an Omi gene, e.g., a gene derived from humans. In a further embodiment, the Omi transgene includes a tissue specific promoter, e.g., a kidney-specific promoter, a cardiac-specific promotor, a neuronal specific promotor, e.g., neuron specific enolase. In other preferred embodiments, the animal has an endogenous Omi gene which is misexpressed, e.g., a knockout. Such a transgenic animal can serve as a model for studying disorders which are related to mutated or mis-expressed Omi alleles or for use in drug screening.

In another aspect, the invention features, a method of modulating, e.g., increasing or decreasing, a stress response in a subject animal or cell. The method includes modulating the activity and/or expression of Omi gene or Omi polypeptide by contacting said cell with an Omi agent. The Omi agent can be an agonist, e.g., an Omi polypeptide or nucleic acid encoding an Omi polypeptide, or an antagonist of Omi activity. Most preferably, the method decreases the stress response in the subject animal or cell, e.g., by using an antagonist of Omi activity. Preferred Omi antagonists include, e.g., a drug, e.g., a protease inhibitor; an antisense oligonucleotide; or an antibody against Omi. The method can be performed in vivo, or in vitro. In in vivo methods the Omi agent is administered to the subject. The administration can be directed to the site where a decrease in cellular stress response is desired, e.g., by topical application or by injection, or administered in a systemic fashion.

In preferred embodiments, the Omi agent is exogenous (e.g., administered to a subject) or is recombinant.

The administration of the Omi agent can be repeated.

In preferred embodiment, the cell is a mammalian cell or a human cell. Exemplary cells include e.g., immune cells; tumor cells, e.g., leukemic or carcinoma cells; or heart cells.

In another aspect, the invention features, a method of rendering a tumor cell more susceptible to chemotherapeutic agents. The method includes modulating, e.g., decreasing, activity and/or expression of an Omi gene or polypeptide by contacting said tumor cell with an Omi agent. The Omi agent can be an agonist, e.g., an Omi polypeptide or nucleic acid encoding an Omi polypeptide, or an antagonist of Omi activity. Most preferably, the Omi agent renders the tumor more suceptible to chemotherapeutic agents by using an antagonist of Omi activity. Preferred antagonists include, e.g., a drug, e.g., a protease inhibitor; an antisense oligonucleotide; or an antibody against Omi. The method can be performed in vivo, or in vitro. In in vivo methods, the Omi agent is administered to the subject. The administration can be directed to the site where an increased suceptibility to hemotherapeutic agents is desired, e.g., by topical application or by injection, or administered in a systemic fashion.

In preferred embodiments, the tumor cell is a leukemic cell, a Burkitt's lymphoma cell, a carcinoma, e.g., colorectal adenocarcinoma or lung carcinoma, colorectal cancer, melanoma, neuroblastoma, or lung cancer, e.g., small cell lung cancer, In preferred embodiments, the Omi agent is exogenous (e.g., administered to a subject) or is recombinant.

The administration of the Omi agent can be repeated.

In another aspect, the invention features, a method of modulating an inflammatory response, e.g., a response to septic shock; a response to ischemia, e.g., very early ischemic injury or post-ischemic injury of an organ, e.g., a kidney, heart, forebrain, e.g., global forebrain ischemia. The method includes modulating, e.g., decreasing, the activity and/or expression of an Omi gene or polypeptide by contacting said tumor cell with an Omi agent. The Omi agent can be an agonist or an antagonist of Omi activity. Most preferably, the method decreases an inflammatory response by, e.g., using an antagonist to Omi activity, e.g., a drug, e.g., a protease inhibitor; an antisense oligonucleotide; or an antibody against Omi. The method can be performed in vivo, or in vitro. In in vivo, methods the Omi agent is administered to the subject. The administration can be directed to the site where a decrease in an inflammatory response is desired, e.g., by topical application or by injection, or administered in a systemic fashion.

In preferred embodiments, the Omi agent is exogenous (e.g., administered to a subject) or is recombinant.

The administration of Omi can be repeated.

In another aspect, the invention provides, a method of treating or preventing in a subject an Omi-related disorder. The method includes: administering to the subject an effective amount of Omi agent, effective to treat or prevent the Omi-related disorder in the subject. The Omi agent can be an agonist, e.g., an Omi polypeptide or nucleic acid encoding an Omi polypeptide, or an antagonist of Omi activity. The administration can be directed to the site where treatment or prevention is desired, e.g., by topical application or by injection, or administered in a systemic fashion.

In preferred embodiments, an Omi-related disorder includes, e.g., a disorder associated with the misexpression of Omi; a disorder associated with aberrant stress response; a cancer e.g., a leukemia, e.g., promyelocytic leukemia, chronic myelogenous leukemia, Burkitt's lymphoma, or carcinoma, e.g., colorectal adenocarcinoma or lung carcinoma, colorectal cancer, melanoma, neuroblastoma, or lung cancer, e.g., small cell lung cancer; a disorder associated with a genetic lesion at chromosome 2, region p12; a disorder associated with abnormal proteolysis of proteins; a disorder associated with septic shock; or an inflammatory condition, e.g., ischemia, e.g., ischemia of the heart, the kidney, or the forebrain.

In preferred embodiments, the subject is a mammal, e.g., human or non-human.

In preferred embodiments, the Omi agent is exogenous (e.g., administered to a subject) or is recombinant.

The administration of the Omi agent can be repeated.

In another aspect, the invention provides, a method of determining if a subject is at risk for a disorder related to a lesion in or the misexpression of a gene which encodes an Omi described herein.

Such Omi-related disorders include, e.g., a disorder associated with the misexpression of Omi; a disorder associated with aberrant stress response; a cancer, e.g., a leukemia, e.g., promyelocytic leukemia, chronic myelogenous leukemia, Burkitt's lymphoma, or carcinoma, e.g., colorectal adenocarcinoma or lung carcinoma, colorectal cancer, melanoma, neuroblastoma, or lung cancer, e.g., small cell lung cancer; a disorder associated with a genetic lesion at chromosome 2, region p12; a disorder associated with abnormal proteolysis of proteins; a disorder associated with septic shock; or an inflammatory condition, e.g., ischemia, e.g., ischemia of the heart, the kidney, or the forebrain.

In preferred embodiments, the molecule is exogenous (e.g., administered to a subject) or is recombinant.

The administration of Omi can be repeated.

The method includes one or more of the following:

detecting, in a tissue of the subject, the presence or absence of a mutation which affects the expression of the Omi gene, or other gene which encodes a subunit of Omi, e.g., detecting the presence or absence of a mutation in a region which controls the expression of the gene, e.g., a mutation in the 5' control region;

detecting, in a tissue of the subject, the presence or absence of a mutation which alters the structure of the Omi gene;

detecting, in a tissue of the subject, the misexpression of the Omi gene, at the mRNA level, e.g., detecting a non-wild type level of an Omi mRNA;

detecting, in a tissue of the subject, the misexpression of the Omi gene, at the protein level, e.g., detecting a non-wild type level of an Omi polypeptide.

In preferred embodiments, the method includes: ascertaining the existence of at least one of: a deletion of one or more nucleotides from the Omi gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:4, or naturally occurring mutants thereof or 5' or 3' flanking sequences naturally associated with the Omi gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments, detecting the misexpression includes ascertaining the existence of at least one of: an alteration in the level of a messenger RNA transcript of the Omi gene; the presence of a non-wild type splicing pattern of a messenger RNA transcript of the Omi gene; or a non-wild type level of Omi.

Methods of the invention can be used prenatally or to determine if a subject's offspring will be at risk for a disorder.

In preferred embodiments, the method includes determining the structure of an Omi gene, an abnormal structure being indicative of risk for the disorder.

In preferred embodiments, the method includes contacting a sample form the subject with an antibody to the Omi protein or a nucleic acid which hybridizes specifically with the Omi gene.

In another aspect, the invention features, a method of evaluating a compound for the ability to interact with, e.g., bind to, a subject Omi polypeptide, e.g., Omi or a fragment thereof, e.g., a regulatory amino terminal domain, a triple repeat motif, an SH3 binding domain, a consensus Mxi2/p38 kinase phosphorylation site, and/or a carboxy terminal serine protease catalytic domain of Omi. The method includes: contacting the compound with the subject Omi polypeptide; and evaluating ability of the compound to interact with, e.g., to bind or form a complex with the subject Omi polypeptide. This method can be performed in vitro, e.g., in a cell free system, or in vivo, e.g., in a two-hybrid interaction trap assay. This method can be used to identify naturally occurring molecules which interact with subject Omi polypeptide. It can also be used to find natural or synthetic inhibitors of subject Omi polypeptide.

In another aspect, the invention features, a method of evaluating a compound, e.g., a polypeptide, e.g., a naturally occurring ligand of, or a naturally occuring substrate which binds to, a subject Omi polypeptide, e.g., Omi or a fragment thereof, e.g., a regulatory amino terminal domain, a signal peptidase site, a triple repeat motif, an SH3 binding domain, a consensus Mxi2/p38 kinase phosphorylation site, and/or a carboxy terminal serine protease catalytic domain, of Omi, for the ability to bind a subject Omi polypeptide. The method includes: contacting the compound with the subject Omi polypeptide; and evaluating the ability of the compound to interact with, e.g., to bind or form a complex with the subject Omi polypeptide, e.g., the ability of the compound to inhibit a subject Omi polypeptide/ligand interaction. This method can be performed in vitro, e.g., in a cell free system, or in vivo, e.g., in a two-hybrid interaction trap assay. This method can be used to identify compounds, e.g., fragments or analogs of a subject Omi polypeptide, which are agonists or antagonists of a subject Omi polypeptide.

In another aspect, the invention features, a method of evaluating a first compound, e.g., a subject Omi polypeptide, e.g., Omi or a fragment thereof, e.g., a regulatory amino terminal domain, a triple repeat motif, a signal peptidase site, an SH3 binding domain, a consensus Mxi2/p38 kinase phosphorylation site, and/or a carboxy terminal serine protease catalytic domain, of Omi, for the ability to bind a second compound, e.g., a second polypeptide, e.g., a naturally occurring ligand of an Omi polypeptide, or substrate which binds to a subject Omi polypeptide. The method includes: contacting the first compound with the second compound; and evaluating the ability of the first compound to form a complex with the second compound. This method can be performed in vitro, e.g., in a cell free system, or in vivo, e.g., in a two-hybrid interaction trap assay. This method can be used to identify compounds, e.g., fragments or analogs of a subject Omi polypeptide, which are agonists or antagonists of a subject Omi polypeptide.

In yet another aspect, the invention features a method for evaluating a compound, e.g., for the ability to modulate an interaction, e.g., the ability to inhibit an interaction of a subject Omi polypeptide, e.g., Omi or a fragment thereof, e.g., a regulatory amino terminal domain, a signal peptidase site, a triple repeat motif, an SH3 binding domain, a consensus Mxi2/p38 kinase phosphorylation site, and/or a carboxy terminal serine protease catalytic domain, of Omi, with a second polypeptide, e.g., a polypeptide, e.g., a natural ligand of a subject Omi polypeptide or a substrate which binds to a subject Omi polypeptide, or a fragment thereof. The method includes the steps of (i) combining the second polypeptide (or preferably a purified preparation thereof), a subject Omi polypeptide, (or preferably a purified preparation thereof), and a compound, e.g., under conditions wherein in the absence of the compound, the second polypeptide, and the subject Omi polypeptide, are able to interact, e.g., to bind or form a complex; and (ii) detecting the interaction, e.g., detecting the formation (or dissolution) of a complex which includes the second polypeptide, and the subject Omi polypeptide. A change, e.g., a decrease or increase, in the formation of the complex in the presence of a compound (relative to what is seen in the absence of the compound) is indicative of a modulation, e.g., an inhibition or promotion, of the interaction between the second polypeptide, and the subject Omi polypeptide. In preferred embodiments: the second polypeptide, and the subject Omi polypeptide, are combined in a cell-free system and contacted with the compound; the cell-free system is selected from a group consisting of a cell lysate and a reconstituted protein mixture; the subject Omi polypeptide, and the second polypeptide are simultaneously expressed in a cell, and the cell is contacted with the compound, e.g. in an interaction trap assay (e.g., a two-hybrid assay).

In yet another aspect, the invention features a two-phase method (e.g., a method having an in vitro, e.g., in a cell free system, and an in vivo phase) for evaluating a compound, e.g., for the ability to modulate, e.g., to inhibit or promote, an interaction of a subject Omi polypeptide subject Omi polypeptide, e.g., Omi or a fragment thereof, e.g., a regulatory amino terminal domain, a signal peptidase site, a triple repeat motif, an SH3 binding domain, a consensus Mxi2/p38 kinase phosphorylation site, and/or a carboxy terminal serine protease catalytic domain, of Omi, with a second compound, e.g., a second polypeptide, e.g., a naturally occurring ligand of an Omi polypeptide, or a substrate which binds to a subject Omi polypeptide, or a fragment thereof. The method includes steps (i) and (ii) of the method described immediately above performed in vitro, and further includes: (iii) determining if the compound modulates the interaction in vitro, e.g., in a cell free system, and if so; (iv) administering the compound to a cell or animal; and (v) evaluating the in vivo effect of the compound on an interaction, e.g., inhibition, of a subject Omi polypeptide, with a second polypeptide.

In another aspect, the invention features, a method of evaluating a compound for the ability to bind a nucleic acid encoding a subject Omi polypeptide, e.g., Omi or a fragment thereof, e.g., a regulatory amino terminal domain, a signal peptidase site, a triple repeat motif, an SH3 binding domain, a consensus Mxi2/p38 kinase phosphorylation site, and/or a carboxy terminal serine protease catalytic domain, of Omi. The method includes: contacting the compound with the nucleic acid; and evaluating ability of the compound to form a complex with the nucleic acid.

In another aspect, the invention features a method of making an Omi polypeptide, e.g., a peptide having a non-wild type activity, e.g., an antagonist, agonist, or super agonist of a naturally occurring Omi polypeptide, e.g., a naturally occurring Omi polypeptide. The method includes: altering the sequence of an Omi polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of an Omi polypeptide having a biological activity of a naturally occurring Omi polypeptide. The method includes: altering the sequence, e.g., by substitution or deletion of one or more residues, of an Omi polypeptide, e.g., altering the sequence of a non-conserved region, or a domain or residue described herein, and testing the altered polypeptide for the desired activity.

In another aspect, the invention features, a human cell, e.g., a tumor cell, a blood cell, e.g., a white blood cell, e.g., an immune cell, e.g., lymphocyte, transformed with nucleic acid which encodes a subject Omi polypeptide.

In another aspect, the invention includes: an Omi nucleic acid, e.g., an Omi nucleic acid inserted into a vector; a cell transformed with an Omi nucleic acid; an Omi made by culturing a cell transformed with an Omi nucleic acid; and a method of making an Omi polypeptide including culturing a cell transformed with an Omi nucleic acid.

Rim Gene

The present invention is based, in part, on the discovery of the gene which encodes a retinoblastoma-interacting Myosin-like polypeptide, Rim polypeptide. Accordingly, the present invention features a purified or isolated preparation or a recombinant preparation of Rim, or a Rim polypeptide. A Rim polypeptide can be a full length Rim or a fragment.

In a preferred embodiment, Rim has at least 60% to about 70%, more preferably at least about 80%, even more preferably at least about 90% to about 95%, and most preferably at least about 99% sequence identity with human Rim, e.g., the human Rim of SEQ ID NO:10. Rim can be identical to a human Rim sequence, e.g., that of SEQ ID NO:10. In another embodiment, Rim is encoded by a nucleic acid molecule which hybridizes under stringent conditions to a nucleic acid molecule of the nucleic acid sequence shown in SEQ ID NO:9. In addition, Rim can have substantially the same electrophoretic mobility as human Rim. Rim has a predicted molecular weight of about 102 kDa. Yet another preferred embodiment of the invention features a Rim which is reactive with a Rim-specific antibody, e.g., an antibody which binds to the epitope recognized by a monoclonal antibody, or a polyclonal antibody. Antibodies against Rim can be made by methods exemplified herein.

In another preferred embodiment, Rim is expressed by a recombinant cell, e.g., a bacterial cell, a cultured cell (e.g., a cultured eukaryotic cell) or a cell of a non-human transgenic organism, e.g., a transgenic plant or animal. Cultured cells can include CHO cells or SF8 cells. Expression of Rim in a transgenic animal can be general or can be under the control of a tissue specific promoter. Preferably, one or more sequences which encode Rim or a fragment thereof are expressed in a preferred cell-type by a tissue specific promoter. Exemplary sequences encoding fragments of Rim include, e.g., two potential coiled-coil leucine zipper structures, an RB family binding motif, an E1A/CtBP binding motif, and four putative nuclear localization sequences.

In a preferred embodiment, the recombinant Rim differs from Rim isolated from tissue in one or more of the following: its pattern of glycosylation, myristilation, phosphorylation, or other posttranslational modifications.

In a preferred embodiment, the recombinant Rim preparation is free of other keratinocyte proteins, lymphocyte proteins, pancreatic proteins, blood cell proteins, or other human proteins.

In a preferred embodiment, the recombinant Rim preparation contains at least 1, 10, or 100 µg of Rim, or a Rim polypeptide.

In a preferred embodiment, the recombinant Rim preparation contains at least 1, 10, or 100 mg of Rim, or a Rim polypeptide.

In a preferred embodiment, the Rim polypeptide has one or more of the following biological acitivities: 1) it binds to a retinoblastoma (RB) protein in vitro and in vivo; 2) it modifies the activity of the RB; 3) it regulates the cell cycle; and/or 4) it mediates oncogenic transformation of a cell.

In other preferred embodiments: the Rim polypeptide includes an amino acid sequence with at least 60%, 80%, 90%, 95%, 98%, or 99% sequence identity to an amino acid sequence from SEQ ID NO:10; the Rim polypeptide includes an amino acid sequence essentially the same as the amino acid sequence in SEQ ID NO:10; the Rim polypeptide is at least 5, 50, 100, 200, 500, 600 or 750 amino acids in length; the Rim polypeptide includes at least 5, preferably at least 10, more preferably at least 20, most preferably at least 5, 50, 100, 200, 500, 600 or 750 contiguous amino acids from SEQ ID NO:10; the Rim polypeptide is either, an agonist or an antagonist, of a biological activity of naturally occurring Rim; the Rim polypeptide is a vertebrate, e.g., a mammalian, e.g. a primate, e.g., a human, Rim polypeptide.

In preferred embodiments: the Rim polypeptide is encoded by the nucleic acid in SEQ ID NO:9, or by a nucleic acid having at least about 50%, more preferably at least about 60% to about 70%, and most preferably at least about 75% sequence identity with the nucleic acid from SEQ ID NO:9.

In preferred embodiments, the Rim polypeptide includes two or more potential coiled-coil leucine zipper motifs, an RB family binding motif, an E1A/CtBP binding motif, and four putative nuclear localization sequences.

In preferred embodiments, the Rim polypeptide includes a leucine zipper motif. In other preferred embodiments, the Rim polypeptide includes two leucine zipper motifs. Generally, the leucine zipper motif is about 21 residues in length, and preferably, has about 70, 80, 90, or 95% sequence identity with the protein sequence shown in SEQ ID NO:10 (amino acid residues 120–141 and 740–761). Preferably, each leucine zipper motif folds into two independent structural domains, one at the amino terminus and the other closer to the carboxy terminus of the protein.

In preferred embodiments, the Rim polypeptide includes an RB family binding motif, e.g., a motif having the amino acid sequence LXCXE (SEQ ID NO:11), wherein X can be any amino acid. Generally, the consensus RB family binding motif is about 5 amino acids, and preferably has about 70, 80, 90, or 95% sequence identity with the protein sequence shown in SEQ ID NO:10 (amino acid residues 153–157). Preferably, the RB family binding motif mediates binding of Rim to an RB polypeptide.

In preferred embodiments, the Rim polypeptide includes an E1A/CtBP binding motif, e.g., a motif having the amino acid sequence PLDLS (SEQ ID NO:12). Generally, the E1A/CtBP binding motif is about 4 amino acids, and preferably has about 70, 80, 90, or 95% sequence identity with the protein sequence shown in SEQ ID NO:10 (amino acid residues 490–494). Preferably, the E1A/CtBP binding motif mediates the binding of Rim to CtBP, and/or CtBP-like moieties.

In preferred embodiments, the Rim polypeptide includes a putative nuclear localization sequence. In other preferred embodiments, it includes up to four nuclear localization sequence. Generally, the putative nuclear localization sequences are about 3 amino acids, and preferably has about 70, 80, 90, or 95% sequence identity with the protein sequence shown in SEQ ID NO:10 (amino acid residues 355–358, 446–449, 877–880 and 878–881). Preferably, the putative nuclear localization sequences mediate nuclear localization of this protein.

In yet another embodiment, the invention features a Rim polypeptide that does not include or has an inactivation in at least one domain, e.g., the amino terminal domain, which serves as an antagonist to one or more Rim biological activities.

In a preferred embodiment, the Rim polypeptide differs in amino acid sequence at up to 1, 2, 3, 5, or 10 residues, from a sequence in SEQ ID NO:10. In other preferred embodiments, the Rim polypeptide differs in amino acid sequence at up to 1, 2, 3, 5, or 10% of the residues from a sequence in SEQ ID NO:10. Preferably, the differences are such that: the Rim polypeptide exhibits a Rim biological activity, e.g., the Rim polypeptide retains a biological activity of a naturally occurring Rim. A position differs if it is a different amino acid, is deleted, or is an insertion, as compared to the sequence of SEQ ID NO:10.

In preferred embodiments,the Rim polypeptide includes a Rim sequence described herein as well as other N-terminal, and/or a C-terminal amino acid sequence.

In preferred embodiments, the Rim polypeptide includes all or a fragment of an amino acid sequence from SEQ ID NO:10, fused, in reading frame, to additional amino acid residues, preferably to residues encoded by genomic DNA 5' to the genomic DNA which encodes a sequence from SEQ ID NO:10.

In yet other preferred embodiments, the Rim polypeptide is a recombinant fusion protein having a first Rim portion and a second polypeptide portion, e.g., a second polypeptide portion having an amino acid sequence unrelated to Rim. The second polypeptide portion can be, e.g., any of glutathione-S-transferase, a DNA binding domain, or a polymerase activating domain. In a preferred embodiment the fusion protein can be used in a two-hybrid assay.

For example, a Rim portion, e.g., a Rim portion containing a coiled-coil leucine zipper domain, e.g., amino acid residues 120–141 and 740–761 of SEQ ID NO:10, can be fused to a DNA binding domain. Alternatively, a Rim portion can be an RB family binding motif, e.g., amino acids 153–157 of SEQ ID NO:10; or an E1A/CtBP binding motif, e.g., amino acids 490–494 of SEQ ID NO:10. In a two hybrid assay, the Rim portion is co-expressed in a cell with a second polypeptide portion containing a transcription activation domain fused to an expression library, e.g., a keratinocyte library.

In a preferred embodiment, the Rim polypeptide includes: amino acid residues 120–141, or a sequence that has 80, 90, 95, 99% sequence identity with 120–141, of SEQ ID NO:10; amino acid residues 740–761, or a sequence that has 80, 90, 95, 99% sequence identity with 740–761 of SEQ ID NO:10; amino acid residues 153–157, or a sequence that has 80, 90, 95, 99% sequence identity with 153–157, of SEQ ID NO:10; amino acid residues 490–494, or a sequence that has 80, 90, 95, 99% sequence identity with 490–494, of SEQ ID NO:10; amino acids 355–358, or a sequence that has 80, 90, 95, 99% sequence identity with 355–358, of SEQ ID NO:10; amino acids 446–449, or a sequence that has 80, 90, 95, 99% sequence identity with 446–449, of SEQ ID NO:10; amino acids 877–880, or a sequence that has 80, 90, 95, 99% sequence identity with 877–880, of SEQ ID NO:10; or amino acids 878–881, or a sequence that has 80, 90, 95, 99% sequence identity with 878–881, of SEQ ID NO:10.

In preferred embodiments, the Rim polypeptide may have an antagonistic or agonists activity, and is capable of: binding to an RB protein.

In a preferred embodiment, the Rim polypeptide is a fragment of a naturally occurring Rim which binds RB protein.

In another aspect, the invention features an Rim polypeptide which is a fragment of a full length Rim polypeptide, e.g., a fragment of a naturally occurring Rim polypeptide, e.g., the polypeptide encoded in SEQ ID NO:10.

In preferred embodiments: the fragment is at least 5, 10, 20, 50, 100, or 150 amino acids in length; the fragment is equal to or less than 200, 150, 100, 50 amino acid residues in length; the fragment has a biological activity of a naturally occurring Rim; the fragment is either, an agonist or an antagonist, of a biological activity of a naturally occurring Rim; the fragment can inhibit, e.g., competitively or non competitively inhibit, the binding of Rim to an Rim-interacting protein, e.g., an RB protein.

In preferred embodiments,the fragment it has at least 60, and more preferably at least 70, 80, 90, 95, 99, or 100% sequence identity with the corresponding amino acid sequence of SEQ ID NO:10.

In preferred embodiments,the fragment is a fragment of a vertebrate, e.g., a mammalian, e.g. a primate, e.g., a human, Rim polypeptide.

In preferred embodiments, the Rim fragment includes a domain, e.g., an RB binding motif, e.g., a motif having the sequence LXCXE (SEQ ID NO:11), wherein X can be any amino acid, which has at least 50, 60, 70, 80, 90, 95, 99 or 100% sequence identity with residues 153–157 of the Rim sequence of SEQ ID NO:10.

In preferred embodiments, the Rim fragment includes an E1A/CtBP binding motif, which has at least 50, 60, 70, 80, 90, 95, 99 or 100% sequence identity with residues 490–494 of the Rim sequence of SEQ ID NO:10.

In preferred embodiments, the Rim fragment includes at least one leucine zipper domain, and preferably about 2 leucine zipper domains, having at least 50, 60, 70, 80, 90, 95, 99 or 100% sequence identity with residues 120–141 or 740–761 of the Rim sequence of SEQ ID NO:10.

In preferred embodiments, the Rim fragment includes at least one nuclear localization signal domain, more preferably 2 to 3 nuclear localization signal domains, and most preferably about 4 nuclear localization signal domains, having at least 50, 60, 70, 80, 90, 95, 99 or 100% sequence identity with residues 355–358, 446–449, 877–880 or 878–881 of the Rim sequence of SEQ ID NO:10.

In preferred embodiments,the fragment can inhibit an interaction, e.g., binding, between Rim and an Rim-interacting protein, e.g., an RB protein.

In a preferred embodiment, the fragment differs in amino acid sequence at up to 1, 2, 3, 5, or 10 residues, from the corresponding residues in SEQ ID NO:10. In other preferred embodiments, the fragment differs in amino acid sequence at up to 1, 2, 3, 5, or 10% of the residues from the corresponding residues in SEQ ID NO:10. In preferred embodiments, the differences are such that the fragment exhibits a Rim biological activity. In other preferred embodiments, the differences are such that the fragment does not have Rim biological activity. In preferred embodiments, one or more, or all of the differences are conservative amino acid changes. In other preferred embodiments, one or more, or all of the differences are other than conservative amino acid changes.

In a preferred embodiment the Rim polypeptide, or fragment thereof, differs in amino acid sequence from the amino acid sequence encoded by EST AA172171 (SEQ ID NO14), EST AA172324 (SEQ ID NO:15), or EST clone 610839.

By "differs" is meant an amino acid sequence other than the amino acid sequence encoded by EST AA172171 (SEQ ID NO:14), EST AA172324 (SEQ ID NO:15), or EST clone 610839, e.g., it differs from the amino acid sequence encoded by EST AA172171 (SEQ ID NO:14), EST AA172324 (SEQ ID NO:15), or EST clone 610839 by at least one amino acid residue, e.g., the Rim polypeptide is at least one amino acid residue shorter, one amino acid residue longer, differs in sequence at least at one position, has a different N terminus, or has a different C terminus, as compared with the amino acid sequence encoded by EST AA172171 (SEQ ID NO:14), EST AA172324 (SEQ ID NO:15), or EST clone 610839.

Polypeptides of the invention include those which arise as a result of the existence of multiple genes, alternative transcription events, alternative RNA splicing events, and alternative translational and postranslational events. The Rim polypeptide can be expressed in systems, e.g., cultured cells, which result in substantially the same postranslational modifications present when expressed Rim is expressed in a native cell, or in systems which result in the omission of postranslational modifications present when expressed in a native cell.

The invention includes an immunogen which includes a Rim polypeptide in an immunogenic preparation, the immunogen being capable of eliciting an immune response specific for the Rim polypeptide, e.g., a humoral response, an antibody response, or a cellular response. In preferred embodiments, the immunogen comprising an antigenic determinant, e.g., a unique determinant, from a protein represented by SEQ ID NO:10.

The present invention also includes an antibody preparation specifically reactive with an epitope of the Rim immunogen or generally of a Rim polypeptide, preferably an epitope which consists all or in part of residues from the the amino acid sequence of SEQ ID NO:10, or an epitope, which when bound to an antibody, results in the modulation of a biological activity.

In preferred embodiments, the Rim-like polypeptide, as expressed in the cells in which it is normally expressed or in other eukaryotic cells, has a molecular weight of about 102 kDa as predicted from SEQ ID NO:9.

In another embodiment, the Rim polypeptide comprises amino acid residues 1–897 of FIG. 7 (SEQ ID NO:10).

In a preferred embodiment, the recombinant Rim polypeptide has one or more of the following characteristics:
(i) it interacts, e.g., binds to, the retinoblastoma (RB) protein;
(ii) it regulates the cell cycle;
(iii) it has a molecular weight, amino acid composition or other physical characteristic of Rim of SEQ ID NO:10;
(iv) it has an overall sequence similarity of at least 50%, preferably at least 60%, more preferably at least 70, 80, 90, or 95%, with a Rim polypeptide of SEQ ID NO:10;
(v) it is found in all human adult tissues;
(vi) it is found at high levels in the pancreas;
(vii) it is found at high levels in tumor cell lines, e.g., promyelocytic leukemia HL-60, chronic myelogenous leukemia K-562, lymphoblastic leukemia MOLT-4, Burkitt's lymphoma Raji, and human colorectal carcinoma SW480 cell lines;
(viii) it has at least one, and preferably two potential coiled-coil leucine zipper structures, which is preferably about 70%, 80%, 90% or 95% identical to amino acid residues 120–141 and 740–761 of SEQ ID NO:10;
(ix) it has an RB family binding motif, which is preferably about 70%, 80%, 90% or 95% identical to amino acid residues 153–157 of SEQ ID NO:10;
(x) it has an E1A/CtBP binding motif, which is preferably about 70%, 80%, 90% or 95% identical to amino acid residues 490–494 of SEQ ID NO:10; and
(xi) it has up to four putative nuclear localization sequences which are preferably about 70%, 80%, 90% or 95% identical to amino acid residues 355–358, 446–449 and 877–880 and 878–881 of SEQ ID NO:10.

Also included in the invention is a composition which includes a Rim polypeptide (or a nucleic acid which encodes it) and one or more additional components, e.g., a carrier, diluent, or solvent. The additional component can be one which renders the composition useful for in vitro and in vivo pharmaceutical or veterinary use.

In another aspect, the invention provides an isolated or substantially pure nucleic acid having or comprising a nucleotide sequence which encodes a polypeptide, the amino acid of which includes, or is, the sequence of an Rim polypeptide.

In a preferred embodiment, the encoded Rim polypeptide has one or more of the following characteristics:
(i) it interacts, e.g., binds to, the retinoblastoma (RB) protein;
(ii) it regulates the cell cycle;
(iii) it has a molecular weight, amino acid composition or other physical characteristic of Rim of SEQ ID NO:10;
(iv) it has an overall sequence similarity of at least 50%, preferably at least 60%, more preferably at least 70, 80, 90, or 95%, with a Rim polypeptide of SEQ ID NO:10;
(v) it is found in all human adult tissues;
(vi) it is found at high levels in the pancreas;
(vii) it is found at high levels in tumor cell lines, e.g., promyelocytic leukemia HL-60, chronic myelogenous leukemia K-562, lymphoblastic leukemia MOLT-4, Burkitt's lymphoma Raji, and human colorectal carcinoma SW480 cell lines;
(viii) it has at least one, and preferably two potential coiled-coil leucine zipper structures, which is preferably about 70%, 80%, 90% or 95% identical to amino acid residues 120–141 and 740–761 of SEQ ID NO:10;
(ix) it has an RB family binding motif, which is preferably about 70%, 80%, 90% or 95% identical to amino acid residues 153–157 of SEQ ID NO:10;
(x) it has an E1A/CtBP binding motif, which is preferably about 70%, 80%, 90% or 95% identical to amino acid residues 490–494 of SEQ ID NO:10; and
(xi) it has up to four putative nuclear localization sequences which are preferably about 70%, 80%, 90% or 95% identical to amino acid residues 355–358, 446–449 and 877–880 and 878–881 of SEQ ID NO:10.

In preferred embodiments, the encoded polypeptide has a biological activity, e.g., the polypeptide is either, an agonist or an antagonist, of a biological activity of a naturally occurring Rim.

In preferred embodiments, the encoded polypeptide is a vertebrate, e.g., a mammalian, e.g. a primate, e.g., a human, Rim polypeptide.

In preferred embodiments, the encoded Rim polypeptide includes two potential coiled-coil leucine zipper motifs, an RB family binding motif, an E1/CtBP binding motif, and four putative nuclear localization sequences.

In preferred embodiments, the encoded Rim polypeptide includes a leucine zipper domain. In other preferred embodiments, the encoded Rim polypeptide includes two leucine zipper domains, each one having at least 60, more preferably at least 70, 80, 90, or 100% sequence identity with nucleotides 358–423 and 2218–2283 of SEQ ID NO:9 (or residues 120–141 and 740–161 of SEQ ID NO:10).

In preferred embodiments, the encoded Rim polypeptide includes an RB binding motif, e.g., a motif having the amino acid sequence LXCXE (SEQ ID NO:11), wherein X can be any amino acid, which has at least 60, more preferably at least 70, 80, 90, or 100% sequence identity with nucleotides 457–471 of SEQ ID NO:9 (or residues 153–157 of SEQ ID NO:10).

In preferred embodiments, the encoded Rim polypeptide includes an E1A/CtBP binding motif, which has at least 60, more preferably at least 70, 80, 90, or 100% sequence identity with nucleotides 1568–1582 of SEQ ID NO:9 (or residues 490–494 of SEQ ID NO:10).

In preferred embodiments, the encoded Rim polypeptide includes a nuclear localization signal domain. In other preferred embodiments, the encoded Rim polypeptide includes up to 4 nuclear localization signal domains, each of them having at least 60, more preferably at least 70, 80, 90, or 100% sequence identity with nucleotides 1063–1074, 1336–1347, 2628–2640 and 2632–2643 of SEQ ID NO:9 (or residues 355–358, 446–449, 877–880 and 878–881 of SEQ ID NO:10).

In a preferred embodiment, the encoded Rim polypeptide differs in amino acid sequence at up to 1, 2, 3, 5, or 10 residues, from the sequence in SEQ ID NO:10. In other preferred embodiments, the Rim polypeptide differs in amino acid sequence at up to 1, 2, 3, 5, or 10% of the residues from a sequence in SEQ ID NO:10. In preferred embodiments,the differences are such that the Rim polypeptide exhibits an Rim biological activity. In other preferred embodiments the differences are such that the Rim polypeptide does not have Rim biological activity. In preferred embodiments,one or more, or all of the differences are conservative amino acid changes. In other preferred embodiments one or more, or all of the differences are other than conservative amino acid changes. A position differs if it is a different amino acid, is deleted, or is an insertion, as compared to the sequence of SEQ ID NO:10.

In preferred embodiments, the encoded Rim polypeptide includes an Rim sequence described herein as well as other N-terminal and/or C-terminal amino acid sequence.

In yet other preferred embodiments, the encoded Rim polypeptide is a recombinant fusion protein having a first Rim portion and a second polypeptide portion, e.g., a second polypeptide portion having an amino acid sequence unrelated to Rim. The second polypeptide portion can be, e.g., any of glutathione-S-transferase, a DNA binding domain, or a polymerase activating domain. In preferred embodiment the fusion protein can be used in a two-hybrid assay.

In preferred embodiments, there is at least 70, 80, 90, 95, 99, or 100% sequence identity between the encoded Rim polypeptide and the amino acid sequence of SEQ ID NO:10.

The encoded polypeptide can be a fragment of a full length Rim polypeptide, e.g., a fragment of a naturally occurring Rim polypeptide, e.g., the polypeptide encoded in SEQ ID NO:10.

In preferred embodiments: the encoded fragment is at least 5, 10, 20, 50, 100, or 150 amino acids in length; the encoded fragment is equal to or less than 200, 150, 100, 50 amino acid residues in length; the encoded fragment has a biological activity of a naturally occurring Rim; the encoded fragment is either, an agonist or an antagonist, of a biological activity of a naturally occurring Rim; the encoded fragment can inhibit, e.g., competitively or non competitively inhibit, the binding of Rim to an Rim interacting protein,e.g., an RB protein.

In preferred embodiments, the encoded fragment it has at least 60, and more preferably at least 70, 80, 90, 95, 99, or 100% sequence identity with the corresponding amino acid sequence of SEQ ID NO:10.

In preferred embodiments, the encoded fragment is a fragment of a vertebrate, e.g., a mammalian, e.g. a primate, e.g., a human, Rim polypeptide.

In preferred embodiments, the encoded Rim fragment includes: amino acid residues 120–141, or a sequence that has 80, 90, 95, 99% sequence identity with 120–30 141, of SEQ ID NO:10; amino acid residues 740–761, or a sequence that has 80, 90, 95, 99% sequence identity with 740–761 of SEQ ID NO:I0; amino acid residues 153–157, or a sequence that has 80, 90, 95, 99% sequence identity with 153–157, of SEQ ID NO:10; amino acid residues 490–494, or a sequence that has 80, 90, 95, 99% sequence identity with 490–494, of SEQ ID NO:10; amino acids 355–358, or a sequence that has 35 80, 90, 95, 99% sequence identity with 355–358, of SEQ ID NO:10; amino acids 446–449, or a sequence that has 80, 90, 95, 99% sequence identity with 446–449, of SEQ ID NO:10; amino acids 877–880, or a sequence that has 80, 90, 95, 99% sequence identity with 877–880, of SEQ ID NO:10; or amino acids 878–881, or a sequence that has 80, 90, 95, 99% sequence identity with 878–88 1, of SEQ ID NO:10.

In preferred embodiments, the encoded fragment includes a region which has at least 50, 60, 70, 80, 90, 95, 99 or 100% sequence identity with a Rim polypeptide. In preferred embodiments,the encoded fragment (which term includes terminal and internal deletions)lacks at least one domain found in naturally occurring Rim.

In preferred embodiments, the encoded fragment can inhibit an interaction, e.g., binding, between Rim and an Rim interacting protein. In preferred embodiments,the encoded fragment does not inhibit an interaction, e.g., binding, between Rim and an Rim interacting protein, e.g., an RB protein.

In a preferred embodiment, the encoded fragment differs in amino acid sequence at up to 1, 2, 3, 5, or 10 residues, from the corresponding residues in SEQ ID NO:10. In other preferred embodiments, the encoded fragment differs in amino acid sequence at up to 1, 2, 3, 5, or 10% of the residues from the corresponding residues in SEQ ID NO:10. In preferred embodiments, the differences are such that the encoded fragment exhibits an Rim biological activity. In other preferred embodiments, the differences are such that the encoded fragment does not have Rim biological activity. In preferred embodiments,one or more, or all of the differences are conservative amino acid changes. In other preferred embodiments one or more, or all of the differences are other than conservative amino acid changes.

In preferred embodiments, the encoded fragment includes an Rim sequence described herein as well as other N-terminal and/or C-terminal amino acid sequence.

In a preferred embodiment, the nucleic acid encodes a polypeptide or fragment thereof which differs by at least one amino acid residue from the amino acid sequence encoded by those EST AA172171 (SEQ ID NO:13), EST AA172324 (SEQ ID NO:14), or EST clone 610839.

In a preferred embodiment, the nucleic acid differs by at least one nucleotide from the nucleotide sequence in those EST AA172171 (SEQ ID NO:13), EST AA172324 (SEQ ID NO:14), or EST clone 610839.

By "differs" is meant a nucleic acid sequence other than a nucleic acid sequence which encodes the amino acid sequence encoded by those EST AA172171 (SEQ ID NO:13), EST AA172324 (SEQ ID NO:14), or EST clone 610839, e.g., it differs from the sequence encoded by those EST AA172171 (SEQ ID NO:13), EST AA172324 (SEQ ID NO:14), or EST clone 610839, by at least one nucleotide, e.g., the Rim encoding nucleic acid is at least one nucleotide shorter, one nucleotide longer, differs in sequence at least one position, has a different 5' terminus, or has a different 3' terminus, as compared with a sequence encoded by those EST AA172171 (SEQ ID NO:13), EST AA172324 (SEQ ID NO:14), or EST clone 610839.

In preferred embodiments, the subject Rim nucleic acid includes a transcriptional regulatory sequence, e.g. at least one of a transcriptional promoter or transcriptional enhancer sequence, operably linked to the Rim gene sequence, e.g., to render the Rim gene sequence suitable for use as an expression vector.

A preferred embodiment of the invention features a nucleic acid molecule having a nucleotide sequence at least about 85% sequence identity to a nucleotide sequence of SEQ ID NO:9. In other preferred embodiments, the Rim polypeptide is encoded by a nucleic acid molecule having a nucleotide sequence with at least about 90% to about 95%, and more preferably about 98% to about 99% sequence identity to the nucleotide sequence from SEQ ID NO:9. In another preferred embodiment, the Rim polypeptide is encoded by the nucleic acid molecule of SEQ ID NO:9.

In preferred embodiments, the subject Rim nucleic acid will include a transcriptional regulatory sequence, e.g. at least one of a transcriptional promoter or transcriptional enhancer sequence, operably linked to the Rim gene sequence, e.g., to render the Rim gene sequence suitable for use as an expression vector.

In yet a further preferred embodiment, the nucleic acid which encodes a Rim polypeptide of the invention, hybridizes under stringent conditions to a nucleic acid probe corresponding to at least 12 consecutive nucleotides of SEQ ID NO:9. In preferred embodiments,the purified nucleic acid is at least 10, more preferably 20, 30, 40, 50 or 100 nucleotides in length.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:9, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a Rim polypeptide of the invention. This includes double stranded nucleic acids as well as coding and antisense single strands.

In another aspect, the invention features a cell or purified preparation of cells which include a Rim transgene, or which otherwise misexpress a Rim gene. The cell preparation can consist of human or non human cells, e.g., rodent cells, e.g., mouse or rat cells, rabbit cells, or pig cells. In preferred embodiments, the cell or cells include a Rim transgene, e.g., a heterologous form of a Rim gene, e.g., a gene derived from humans (in the case of a non-human cell). The Rim transgene can be misexpressed, e.g., overexpressed or underexpressed. In other preferred embodiments, the cell or cells include a gene which misexpress an endogenous Rim gene, e.g., a gene the expression of which is disrupted, e.g., a knockout. Such cells can serve as a model for studying disorders which are related to mutated or mis-expressed Rim alleles or for use in drug screening.

In another aspect, the invention features a transgenic Rim organism, e.g., an animal, e.g., a rodent, e.g., a mouse or a rat, a rabbit, a pig, a goat, or a cow; or a plant. In preferred embodiments, the transgenic animal includes (and preferably expresses) a heterologous form of a Rim gene, e.g., a gene derived from humans. In a further embodiment, the Rim transgene includes a tissue specific promoter. In other preferred embodiments, the animal has an endogenous Rim gene which is misexpressed, e.g., a knockout. Such a transgenic animal can serve as a model for studying disorders which are related to mutated or mis-expressed Rim alleles or for use in drug screening.

In another aspect, a method of modulating, e.g., increasing or decreasing, the cell cycle in a subject animal or cell. The method includes modulating expression and/or activity of Rim gene or Rim polypeptide by contacting said cell with a Rim agent. The Rim agent can be a Rim agonist, e.g., a Rim polypeptide or nucleic acid encoding a Rim polypeptide, or a Rim antagonist, e.g., a drug; e.g., a competitive inhibitor of the interaction of Rim with an RB protein; an antisense oligonucleotide; or an antibody against Rim. The method can be performed in vivo, or in vitro. In in vivo methods the Rim agent is administered to the subject. The administration can be directed to the site where a decrease in cellular stress response is desired, e.g., by topical application or by injection, or administered in a systemic fashion.

In preferred embodiments, the Rim agent is exogenous (e.g., administered to a subject) or is recombinant.

The administration of the Rim agent can be repeated.

In preferred embodiment, the cell is a mammalian cell or a human cell. Exemplary cells include e.g., tumor cells, e.g., leukemic or carcinoma cells, e.g., a cell found in colorectal adenocarcinoma or lung carcinoma, colorectal cancer, melanoma, neuroblastoma, or lung cancer, e.g., small cell lung cancer.

In another aspect, the invention provides, a method of treating or preventing in a subject a Rim-related disorder. The method includes: administering to the subject an effective amount of Rim agent, effective to treat or prevent the Rim-related disorder in the subject. The Rim agent can be an agonist, e.g., a Rim polypeptide or nucleic acid encoding an Rim polypeptide, or an antagonist of Rim activity. The administration can be directed to the site where treatment or prevention is desired, e.g., by topical application or by injection, or administered in a systemic fashion.

In preferred embodiments, a Rim-related disorder includes, e.g., a disorder associated with the misexpression of Rim; a disorder associated with oncogenic transformation, e.g., a cancer e.g., an osteosarcoma, a retinoblastoma, carcinoma, e.g., colorectal adenocarcinoma or lung carcinoma, colorectal cancer, melanoma, neuroblastoma, or lung cancer, e.g., small cell lung cancer, bladder cancer, a leukemia, e.g., promyelocytic leukemia, chronic myelogenous leukemia, Burkitt's lymphoma; a disorder associated with a genetic lesion at chromosome 18, region q11.2; and a disorder associated with cell cycle deregulation.

In preferred embodiments, the subject is a mammal, e.g., human or non-human.

In preferred embodiments, the Rim agent is exogenous (e.g., administered to a subject) or is recombinant.

The administration of the Rim agent can be repeated.

In another aspect, the invention provides, a method of determining if a subject is at risk for a disorder related to a lesion in or the misexpression of a gene which encodes a Rim described herein.

Such disorders include, e.g., a disorder associated with the misexpression of Rim; a disorder associated with oncogenic transformation, e.g., a cancer e.g., an osteosarcoma, a retinoblastoma, a carcinoma, e.g., colorectal adenocarcinoma or lung carcinoma, colorectal cancer, melanoma, neuroblastoma, or lung cancer, e.g., small cell lung cancer, bladder cancer, a leukemia, e.g., promyelocytic leukemia, chronic myelogenous leukemia, Burkitt's lymphoma; a disorder associated with a genetic lesion at chromosome 18, region q11.2; and a disorder associated with cell cycle deregulation.

The method includes one or more of the following:

detecting, in a tissue of the subject, the presence or absence of a mutation which affects the expression of the Rim gene, or other gene which encodes a fragment of Rim, e.g., detecting the presence or absence of a mutation in a region which controls the expression of the gene, e.g., a mutation in the 5' control region;

detecting, in a tissue of the subject, the presence or absence of a mutation which alters the structure of the Rim gene;

detecting, in a tissue of the subject, the misexpression of the Rim gene, at the mRNA level, e.g., detecting a non-wild type level of a Rim mRNA;

detecting, in a tissue of the subject, the misexpression of the Rim gene, at the protein level, e.g., detecting a non-wild type level of a Rim polypeptide.

In preferred embodiments,the method includes: ascertaining the existence of at least one of: a deletion of one or more nucleotides from the Rim gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:9, or naturally occurring mutants thereof or 5' or 3' flanking sequences naturally associated with the Rim gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments,detecting the misexpression includes ascertaining the existence of at least one of: an alteration in the level of a messenger RNA transcript of the Rim gene; the presence of a non-wild type splicing pattern of a messenger RNA transcript of the Rim gene; or a non-wild type level of Rim.

Methods of the invention can be used prenatally or to determine if a subject's offspring will be at risk for a disorder.

In preferred embodiments,the method includes determining the structure of a Rim gene, an abnormal structure being indicative of risk for the disorder.

In preferred embodiments,the method includes contacting a sample form the subject with an antibody to the Rim protein or a nucleic acid which hybridizes specifically with the Rim gene.

In another aspect, the invention features, a method of evaluating a compound for the ability to interact with, e.g., to bind to, a subject Rim polypeptide, e.g., Rim or a fragment thereof, e.g., a leucine zipper motif, an RB family binding motif, an E1A/CtBP binding motif, and/or a nuclear localization sequence, of Rim. The method includes: contacting the compound with the subject Rim polypeptide; and evaluating ability of the compound to interact with, e.g., to bind to, or form a complex with the subject Rim polypeptide. This method can be performed in vitro, e.g., in a cell free system, or in vivo, e.g., in a two-hybrid interaction trap assay. This method can be used to identify naturally occurring molecules which interact with the subject Rim polypeptide. It can also be used to find natural or synthetic inhibitors of the subject Rim polypeptide.

In another aspect, the invention features, a method of evaluating a compound, e.g., a polypeptide, e.g., a naturally occurring ligand of or a naturally occuring substrate which binds to a subject Rim polypeptide, e.g., Rim or a fragment thereof, e.g., a leucine zipper motif, an RB family binding motif, an E1A/CtBP binding motif, and/or a nuclear localization sequence, of Rim, for the ability to bind a subject Rim polypeptide. The method includes: contacting the compound with the subject Rim polypeptide; and evaluating the ability of the compound to interact with, e.g., to bind to, or form a complex with the subject Rim polypeptide, e.g., the ability of the compound to inhibit a subject Rim polypeptide/ligand interaction. This method can be performed in vitro, e.g., in a cell free system, or in vivo, e.g., in a two-hybrid interaction trap assay. This method can be used to identify compounds, e.g., fragments or analogs of a subject Rim polypeptide, which are agonists or antagonists of a subject Rim polypeptide.

In another aspect, the invention features, a method of evaluating a first compound, e.g., a subject Rim polypeptide, e.g., Rim or a fragment thereof, e.g., a leucine zipper motif, an RB family binding motif, an E1A/CtBP binding motif, and/or a nuclear localization sequence, of Rim, for the ability to bind a second compound, e.g., a second polypeptide, e.g., a naturally occurring ligand of or substrate which binds to a subject Rim polypeptide. The method includes: contacting the first compound with the second compound; and evaluating the ability of the first compound to form a complex with the second compound. This method can be performed in vitro, e.g., in a cell free system, or in vivo, e.g., in a two-hybrid interaction trap assay. This method can be used to identify compounds, e.g., fragments or analogs of a subject Rim polypeptide, which are agonists or antagonists of a subject Rim polypeptide.

In yet another aspect, the invention features a method for evaluating a compound, e.g., for the ability to modulate an interaction, e.g., the ability to inhibit an interaction of a subject Rim polypeptide, e.g., Rim or a fragment thereof, e.g., a leucine zipper motif, an RB family binding motif, an E1A/CtBP binding motif, and/or a nuclear localization sequence, of Rim, with a second polypeptide, e.g., a polypeptide, e.g., a natural ligand of the Rim polypeptide or a substrate which binds to a subject Rim polypeptide, or a fragment thereof. The method includes the steps of (i) combining the second polypeptide (or preferably a purified preparation thereof), a subject Rim polypeptide, (or preferably a purified preparation thereof), and a compound, e.g., under conditions wherein in the absence of the compound, the second polypeptide, and the subject Rim polypeptide, are able to interact, e.g., to bind or form a complex; and (ii) detecting the interaction, e.g., detecting the formation (or dissolution) of a complex which includes the second polypeptide, and the subject Rim polypeptide. A change, e.g., a decrease or increase, in the formation of the complex in the presence of a compound (relative to what is seen in the absence of the compound) is indicative of a modulation, e.g., an inhibition or promotion, of the interaction between the second polypeptide, and the subject Rim polypeptide. In preferred embodiments: the second polypeptide, and the subject Rim polypeptide, are combined in a cell-free system and contacted with the compound; the cell-free system is selected from a group consisting of a cell lysate and a reconstituted protein mixture; the subject Rim polypeptide, and the second polypeptide are simultaneously expressed in a cell, and the cell is contacted with the compound, e.g. in an interaction trap assay (e.g., a two-hybrid assay).

In yet another aspect, the invention features a two-phase method (e.g., a method having an in vitro, e.g., in a cell free system, and an in vivo phase) for evaluating a compound, e.g., for the ability to modulate, e.g., to inhibit or promote, an interaction of a subject Rim polypeptide, e.g., Rim or a fragment thereof, e.g., a leucine zipper motif, an RB family binding motif, an E1A/CtBP binding motif, and/or a nuclear localization sequence, of Rim, with a second compound, e.g., a second polypeptide, e.g., a naturally occurring ligand of a Rim polypeptide or a substrate which binds to a subject Rim polypeptide, or a fragment thereof. The method includes steps (i) and (ii) of the method described immediately above performed in vitro, and further includes: (iii) determining if the compound modulates the interaction in vitro, e.g., in a cell free system, and if so; (iv) administering the compound to a cell or animal; and (v) evaluating the in vivo effect of the compound on an interaction, e.g., inhibition, of a subject Rim polypeptide, with a second polypeptide.

In another aspect, the invention features, a method of evaluating a compound for the ability to bind a nucleic acid encoding a subject Rim polypeptide, e.g., Rim or a fragment thereof, e.g., a leucine zipper motif, an RB family binding motif, an E1A/CtBP binding motif, and/or a nuclear localization sequence, of Rim. The method includes: contacting the compound with the nucleic acid; and evaluating ability of the compound to form a complex with the nucleic acid.

In another aspect, the invention features a method of making a Rim polypeptide, e.g., a peptide having a non-wild type activity, e.g., an antagonist, agonist, or super agonist of a naturally occurring Rim polypeptide, e.g., a naturally occurring Rim polypeptide. The method includes: altering the sequence of a Rim polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a Rim polypeptide having a biological activity of a naturally occurring Rim polypeptide. The method includes: altering the sequence, e.g., by substitution or deletion of one or more residues, of a Rim polypeptide, e.g., altering the sequence of a non-conserved region, or a domain or residue described herein, and testing the altered polypeptide for the desired activity.

In another aspect, the invention features, a human cell, e.g., a tumor cell, e.g., a white blood cell, e.g., a lymphocyte, transformed with nucleic acid which encodes a subject Rim polypeptide.

In another aspect, the invention includes: a Rim nucleic acid, e.g., a Rim nucleic acid inserted into a vector; a cell transformed with a Rim nucleic acid; a Rim made by culturing a cell transformed with a Rim nucleic acid; and a method of making a Rim polypeptide including culturing a a cell transformed with a Rim nucleic acid.

A "heterologous promoter", as used herein is a promoter which is not naturally associated with a gene or a purified nucleic acid.

A "purified" or "substantially pure" or isolated "preparation" of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 Hg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

As used herein, the term "subject" refers to human and non-human animals. In preferred embodiments, the subject is a a human, e.g., person, e.g., a person having an Omi related disorder. The term "non-human animals" of the invention includes all vertebrates, e.g., mammals and non-mammals, such as non-human primates, ruminants, birds, amphibians, reptiles.

An "isolated" or "pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA can also includes a recombinant DNA which is part of a hybrid gene encoding sequence.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithim. Preferably, the alignment can be performed using the Clustal Method. Multiple alignment paramethers include GAP Penalty=10, Gap Length Penalty=10. For DNA alignments, the pairwise alignment paramenters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

Additional non-limiting example of a mathematical algorithim utilized for the comparison of sequences is the algorithm of Karlin and Altschul 1990 Proc. Natl. Acad. Sci. USA 87:2264–68, modified as in Karlin and Altschul 1993 Proc. Natl. Acad. Sci. USA 90:5873–77. Such an algorithm is incorporated into the NBLAST and XBLAST programs (version 2.0) of Altschul, et al. 1990 J. Mol. Biol. 215:403–10. BLAST nucleotide searches can be performed performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., 1997 Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS 1989. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The terms "peptides", "proteins", and "polypeptides" are used interchangeably herein.

As used herein, the term "transgene" means a nucleic acid sequence (encoding, e.g., one or more subject Nmi, Omi or Rim polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as mammary tissue. The term also covers so-called "leaky" promoters, which regulate expression of a selected DNA primarily in one tissue, but cause expression in other tissues as well.

"Unrelated to an Nmi, Omi or Rim amino acid or nucleic acid sequence" means having less than 30% sequence identity, less than 20% sequence identity, or, preferably, less than 10% homology with a naturally occuring Nmi, Omi or Rim sequence disclosed herein.

A polypeptide has Nmi, Omi or Rim biological activity if it has one or more of the properties of Nmi, Omi or Rim disclosed herein. A polypeptide has biological activity if it is an antagonist, agonist, or super-agonist of a polypeptide having one of the properties of Nmi, Omi or Rim disclosed herein. "Misexpression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

As described herein, one aspect of the invention features a substantially pure (or recombinant) nucleic acid which includes a nucleotide sequence encoding an Nmi, Omi or Rim polypeptide and/or equivalents of such nucleic acids. The term nucleic acid as used herein can include fragments and equivalents. The term equivalent refers to nucleotide sequences encoding functionally equivalent polypeptides. Equivalent nucleotide sequences will include sequences that differ by one or more nucleotide substitutions, additions or deletions, such as allelic variants, and include sequences that differ from the nucleotide sequences disclosed herein by degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* 1984; the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DETAILED DESCRIPTION

The drawings are briefly described.

FIG. 1 is a depiction of the sequence of an Nmi cDNA and protein, SEQ ID NO:1. The sequence of a 1,426-nucleotide cDNA was determined by sequencing cDNA clones isolated from the Hela cDNA library.

FIG. 2 is a comparison of the Nmi amino acid (SEQ ID NO:1) with sequence of human IFP 35 (SEQ ID NO:3) and sequence of *C. elegans* CEF 59 (SEQ ID NO:2). Sequences from human Nmi, IFP 35 and *C. elegans* were aligned by the BLAST program. Identical amino acids are shown connected with "|", and similar residues with "+". Similar residues are residues wherein both residues are hydrophobic, both residues are hydrophilic, both residues are acidic, or both residues are basic. Numbers on the top right refer to amino acid positions in the Nmi protein and the numbers on the bottom of the sequences refer to amino acid positions in the CEF59 or IFP35, respectively.

FIG. 3 is an autoradiogram which depicts the expression of C-myc and Nmi in different cancer cell lines. each lane contains 2 μg of poly(A)+mRNA (A) the blot was probed with for C-myc. It was then reprobed for Nmi expression (B). Lane 1, promyelocytic leukemia HL-60; Lane 2, Hela cell S3; Lane 3, chronic myelogenous leukemia K-562; Lane 4, lymphoblastic leukemia MOLT-4; Lane 5, Burkitt's lymphoma Raji; Lane 6, colorectal adenocarcinoma SW480; Lane 7, lung carcinoma A549; and Lane 8, melanoma G361.

FIG. 4A depicts the nucleotide and deduced amino acid sequence of Omi cDNA and protein.

FIG. 5A depicts a comparison of the amino acid sequences of Omi, L56 and HtrA.

FIG. 7 depicts the nucleotide and deduced amino acid sequences of the Rim cDNA.

The NMI Locus

Figure 3:
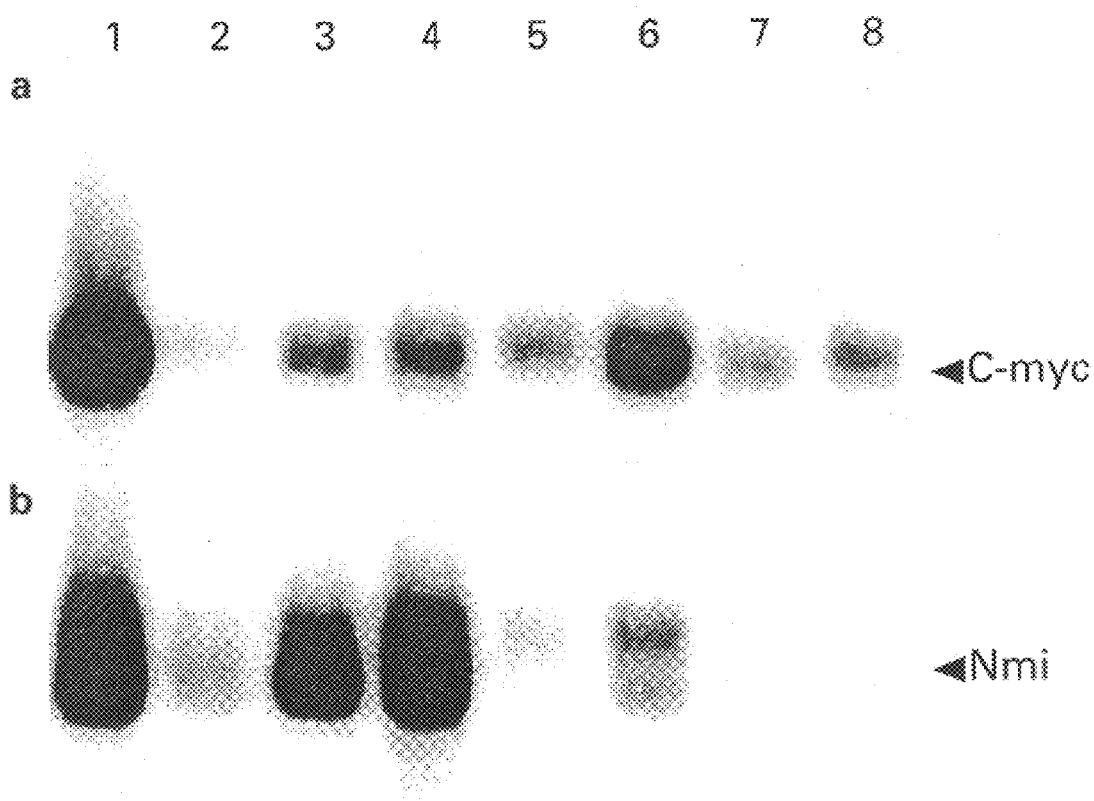

The carboxyl terminus of N-myc that includes the bHLH-Zip region was used as bait in a yeast two-hybrid screen. Among the different interactors identified was a novel gene, Nmi, that represents a 307 amino acid protein. Nmi, in yeast, interacts with the carboxyl terminus of N-myc or C-myc. It also associates with full length N- or C-myc in mammalian cells and the association is strong enough for these proteins to co-precipitate.

Nmi also binds, equally well, to other bHLH-Zip, bHLH or Zip transcription factors but not zinc-finger proteins. Nmi, at its carboxyl terminus, has homology to a coiled-coil heptad repeat region found in CEF 59, a *C. elegans* protein, recently reported with unknown function. This coiled-coil region of Nmi is required for its interactions with the different transcription factors. At the amino terminus, Nmi has homology with yet another protein, IFP 35. IFP 35 encodes a 282-amino acid protein that has a leucine zipper domain at its carboxyl terminus, but lacks a basic region. IFP 35 is found in the cell nucleus, after interferon treatment, and is expressed in a wide variety of cell types including fibroblasts, macrophages, and epithelial cells (Bange et al., 1994, *J. Biol Chem,* 269, 1091–1098).

The observation that Nmi and Myc proteins can form stable heterocomplexes provides the first evidence that the C-terminus of Myc interacts with proteins other than Max. Unlike the Myc/Max heterodimers that bind DNA and activate transcription, the Nmi/Myc heterodimers probably have a different function. Nmi has no basic region or any well defined structural motif and interacts with a diverse class of transcription factors. Thus, Nmi appears to have a more general function and could be involved in promoting dimerization of bHLH-Zip, bHLH, and bZip proteins. Nmi may work as an adapter molecule stabilizing dimerisation and/or modifying DNA site selection. This is comparable to HTLV-I Tax protein or the high mobility group protein HMG I(Y) that interact with the basic domains of bZip transcription factors of considerable sequence diversity, increase dimer stability and modify their choice of DNA binding sites (Baranger et al., 1995, *Nature,* 376, 606–608; Du and Maniatis, 1994, *Proc. Natl. Acad Sci. USA,* 91, 11318–11322; Perini et al., 1995, *Nature,* 376, 602–605).

The pattern of Nmi expression is interesting since it is expressed everywhere except brain, both in fetal and adult human tissues. It is also not expressed in the skin and melanoma was the only cancer, found so far, not to express Nmi1. Both brain and skin are tissues derived from ectoderm. The presence of Nmi in the original human fetal brain yeast cDNA,library can only be explained, if the brain tissue used also contained non-brain material. Interestingly, the low levels of Nmi expression in normal tissues are in contrast with the high levels of Nmi observed in transformed cell lines. Among eight cancer lines tested, highest levels were observed in four leukemia cell lines. The same lines were also observed to be expressing high levels of C-myc mRNA. Nmi is localized on human chromosome 22q13.3. Chromosome 22, also known as the Philadelphia chromosome, where the fusion of c-ABL (9q34) to the BCR gene (22q11) is a typical cause of some leukemias (Rabbitts, 1991 *Cell,* 67, 641–644; Sawyers, and Denny, 1994, *Cell,* 77, 171–173). Deletions and rearrangements of the same chromosomal location as Nmi are also involved in cases of mental retardation expressed in brain it would be of interest to see whether ectopic expression of Nmi caused by chromosomal rearrangement might be involved in any of these clinical conditions.

Isolation and Characterization of Nmi

The carboxyl terminal region of N-myc containing the bHLH-Zip motif was used as bait in a two-hybrid system to isolate N-myc interacting proteins. Because N-myc is mainly expressed in the developing brain, a yeast expression cDNA library made from human fetal brain was used. The selection was performed with an EGY48 yeast strain containing the LexA-N-myc bait plus the pJK103, a medium-sensitive LexAop-lacZ reporter. The first 200 Leu$^+$ clones that appeared on galactose-Leu$^-$selection plates were picked and 80 showed galactose-dependent blue color on X-gal plates. These were further classified according to the intensity of blue color. Thirty-one were classified as strong interactors, the rest were classified as weak interactors. Restriction digests and DNA sequence analysis showed they represented 13 distinct families. One of these families consisted of six members and was named Nmi. The longest cDNA of this family contained an insert of 1,164 nucleotides, corresponding to nucleotides 262 to 1426 in FIG. 1 (SEQ ID NO:1). This sequence encodes a protein consisting of 307 amino acids fused in frame with the acidic transcription activation domain of the pJG4-5 vector. To determine whether there were any longer forms of Nmi, two human cDNA libraries, a HeLa and a Jurkat cDNA library, were screened. Eight clones were isolated from the Hela library, and two from the Jurkat. Four out of these ten positive clones represented longer inserts than the original Nmi cDNA that was isolated from the yeast screen. The longest cDNA clone had an insert of 1,426 nucleotides and is shown in FIG. 1, SEQ ID NO:1. It has an ATG at position 280 that was assigned as the initiating methionine because it conforms well to the consensus Kozak sequence established for sites of translational initiation (Kozak, 1987, *Nucleic Acids Res.,* 15, 8125–8132). A sequence homology search revealed that the carboxyl-terminus of Nmi is 25% identical and 46% similar to a human interferon-induced leucine zipper protein, IFP 35 (Bange et al., 1994, *J Biol Chem,* 269, 1091–1098) Its amino terminus is 22% identical and 48% similar to the coiled-coil heptad repeat regions of a *Caenorhabditis elegans* protein, CEF59, see FIG. 2. In order to test the specificity of Nmi, a panel of baits was used. In yeast, Nmi interacted strongly not only with LexA-N-myc, but also LexA-C-myc, LexA-Max, all of which have a bHLH-Zip motif. Nmi also interacted strongly with LexA-daughterless which has a bHLH motif; and LexA-C-fos which has a basic-leucine zipper motif. However, Nmi did not interact with LexA-Cdc2, LexA-Cyclin, or LexA-R4c which is a TGF b type I receptor.

Interaction of Nmi with Myc proteins in yeast was evaluated as follows. The full length Nmi cDNA fused in-frame with the transcriptional activator B42 in JG4-5 vector was transformed into EGY 48 yeast strain containing one of the following baits: LexA-N-myc (N-myc), LexA-C-myc (C-myc), LexA-daughterless (DA), LexA-C-fos (C-fos), LexA-Max (Max), LexA-cdc2 (cdc), LexA-cyclin C (cyc), or LexA-R4CK230R (R4C). Transformants were tested for specific interaction on glucose or galactose X-gal plates. Blue color indicates a positive protein-protein interaction.

The methods are discussed in more detail below.

Interaction trap. An interaction "hunt" for N-myc interactors was performed essentially as previously described (Zervos et al., 1993, Cell, 72, 223–232). EGY48 MATa trp1 ura3 his3 LEU2:pLexAop6-LEU2 was used as a host for all two-hybrid experiments as described (Zervos et al., 1993, Cell, 72, 223–232). For the 5-bromo-4-chloro-3-indolyl b-D-galactoside (X-gal) assay, a reporter pJK103 was used, which directs expression of a Gal1-lacZ gene from two high affinity ColE1 LexA operators (Kamens et al., 1990, Mol. Cell. Biol., 10, 2840–2847). This reporter presumably binds four LexA dimers, but it is not as sensitive as the LexAop-LEU2 reporter in EGY48. All plasmids used to express the different baits were based on pL202PI (Gyuris et al., 1993, Cell, 75, 791–803), which carries the HIS3$^+$marker and a 2m replicator. All baits were fused to LexA DNA-binding domain and the C-terminal dimerization domain. The LexA-N-myc bait contains the carboxyl-terminal 224 amino acids of human N-myc, this includes both the bHLH and LZ domains. The Lex-C-myc bait contains the carboxy-terminal 176 amino acids of human C-myc. Control baits, LexA-C-fos, LexA-daughterless, LexA-Cdc2, LexA-Cyclin C, LexA-bicoid, and LexA-R4CK230R were as described (Zervos et al., 1993, Cell, 72, 223–232; Wang et al., 1994, Science, 256, 674— 676). The oligo(dT)-primed human fetal brain cDNA library was a gift from Dr. D. Krainc. The cDNA is cloned unidirectionally into vector pJG4-5 which directs the synthesis of library-encoded proteins as fusions to the influenza hemagglutinin epitope (HA), the B42 acidic activation domain, and the SV40 nuclear localization signal.

Selection of N-myc interactors. pJK103 and PL-LexA-N-myc were introduced into the yeast strain, EGY48, by transformation using a variation of the lithium acetate method (Ito et al., 1983, J. Bacteriol, 153, 163–168). This strain was maintained under selection for the URA3 and HIS3 markers and was transformed with the human fetal brain library. A total of about $2.5\times10^6$ primary yeast transformants were selected on twelve 25×25 cm Ura$^-$His$^-$Trp$^-$ glucose plates, scraped, pooled, and stored at −70° C. Plating efficiency was determined on Ura$^-$His$^-$Trp$^-$ galactose plates and 10 colony-forming units per original transformant, approximately $2.5\times10^7$ cells, were plated on two standard Ura$^-$His$^-$Trp$^-$Leu$^-$– galactose plates. Three days later, colonies appeared; these were restreaked and tested on Ura$^-$His$^-$Trp$^-$X-gal glucose and Ura$^-$His$^-$Trp$^-$X-gal galactose. Plasmids from colonies that grew on Leu$^-$ plates and turned blue on X-gal medium were isolated and introduced into KC8 cells by electroporation. cDNAs were analyzed by restriction analysis and DNA sequencing.

Analysis of cDNAs encoding Nmi. The complete sequence of Nmi cDNA clones isolated from the yeast expression cDNA library was determined by sequencing both strands using a commercially available kit (US Biochemicals). Nmi cDNA was used to probe two human cDNA libraries, a human Hela cDNA library (Clontech) and a Jurkat lambda ZAP library (Stratagene) in order to isolate longer cDNAs. Sequence homology searches were performed using the BLAST program on the NCBI network server.

Expression of Nmi in normal and cancer cell lines.

To monitor Nmi expression, two Northern blots containing poly(A) RNA from different human fetal or adult human tissues were probed. (Each lane contained 2 mg of poly(A)$^+$ mRNA from corresponding tissue. Nmi mRNA runs with an apparent mobility of 1.35 kb.) In fetal tissues, expression of Nmi is relatively high in liver, and present in lung and kidney, but absent in brain. In adult tissues, expression of Nmi is similar to that in fetal tissues; Nmi expression is also absent in the adult brain, slightly high in spleen, lung and liver. Adult expression was also seen in the pancreas, skeletal muscle and placenta. Both fetal and adult blots were hybridized with the same radiolabeled Nmi probe, the fetal blot was exposed for 24 hours whereas the adult blot was exposed for 48 hours. Given the relative densities of the autoradiograms, it could be seen that Nmi mRNA is more abundant in fetal tissues.

Because overexpression of Myc genes is often associated with various human cancers, the expression of C-myc and Nmi in eight different cancer cell lines was compared. C-myc was expressed in all eight cancer cell lines. See FIG. 3. High levels of Nmi were found in promyelocytic leukemia HL-60, chronic myelogenous leukemia K-562, colorectal, and lymphoblastic leukemia MOLT-4 and Burkitt's lymphoma Raji. Interestingly, high expression of Myc was also found in the same cancer cell lines.

Northern blot analysis was performed essentially as follows. Human mRNA tissue blots (Clontech) were hybridized at 42° C. with a radiolabeled Nmi cDNA probe as described (Sambrook et al., 1989, Molecular Cloning—a laboratory manual, Cold Spring Harbor Laboratory Press, NY). Blots were washed twice with 0.1% SSC, 0.1% SDS solution at 65° C. for 40 minutes and subjected to autoradiography. The cancer blot (Clontech) was probed with radiolabeled Nmi fragment, then stripped and reprobed with full length radiolabeled C-myc cDNA.

Interaction of Nmi with Myc genes in mammalian cells

To investigate the molecular interactions of Nmi with Myc proteins in vivo, their interactions in mammalian cells were studied. Full length N-myc, C-myc, and Nmi were cloned into mammalian expression vectors, and transiently transfected in different combinations into 293 cells. Cell lysates were prepared from transfected cells and association of the different proteins was monitored using antibodies against HA-tagged proteins. Nmi was expressed as a single protein band on a Western-blot with an approximate size of about 40 kD. It was co-precipitated with N-myc or C-myc.

Full-length His-tagged N-myc was subcloned into pCMV8 vector (Andersson et al., 1989, J Biol Chem, 264, 8222–8229), GST-C-myc into pEBG vector (Mizushima and Nagata, 1990, Nucl. Acids Res., 18, 5322–5326), and Nmi-HA into pMT3 vector (Grove et al., 1991, Mol. Cell. Biol., 11, 5541–5550). 293 cells were transfected with the above vectors in various combinations. Cell lysates from cells transfected with 10 mg of Nmi-pMT3 vector, 10 mg of C-myc-pEBG vector, 10 mg of Nmi-pMT3 and 10 mg of C-myc-pEBG vectors, 10 mg of Nmi-pMT3 and 10 mg of N-myc-pCMV8 vectors, and 10 mg of N-myc-pCMV8 vector were passed through GST-resin or His-resin columns. Proteins specifically bound to the column were eluted, and detected using anti-HA monoclonal antibody.

Co-precipitation in mammalian cells was performed essentially as follows. 293T cells, an adenoviral transformed human embryonic kidney cell line, were grown in Dulbecco's modified Eagle's medium (DMEM, Sigma) containing 10% (vol/vol) fetal calf serum (FCS, Sigma). All transient transfections were done on 100-mm dishes using the calcium phosphate method (Pear et al., 1993, Proc. natl. Acad. Sci. USA, 90, 8392–35 8396). Briefly, the transfection cocktail was prepared by mixing 10 to 20 mg DNA in 438 ml H₂O with 62 ml 2M CaCl₂, then adding 500 ml 2×HBS-PO₄ (pH 7.05) and mixing it by bubbling air through it. Three days after transfection, cells were washed once with phosphate-buffered saline (PBS), scraped and lysed in 200 ml of 50 mM HEPES, pH7.5, 150 mM NaCl, 1% Triton X-100, 1.5 mM MgCl₂, 1 mM EDTA, 10 mM sodium pyrophosphate, 100 mM sodium orthovanadate, 100 mM NaF, 30 mM p-nitrophenyl phosphate, 10 mg/ml aprotinin, and 10 mg/ml leupeptin. Lysates were centrifuged for 5 min at 14,000×g. For glutathione S-transferase (GST) experiment, the supernatant was mixed with 200 ml of a 50% suspension of glutathione-agarose beads (Sigma) in PBS and left on a shaker for 2 hours. The resin was collected by centrifugation (1000 rpm, 10 min) and washed five times with PBS, and then with elution buffer (20 mM HEPES, 0.5 M NaCl, 20 mM glutathione, 100 mM KCl, 0.2 mM EDTA). For the histidine (His) tagged constructs, the supernatant was mixed with His-Bind resin, and purified using a commercially available kit (Novagen). 10 ml of eluted proteins was boiled 5 min in 10 ml 2×SDS-sample buffer and resolved by 10% SDS polyacrylamide gel electrophoresis (SDS-PAGE). Proteins separated by SDS-PAGE were electro-transferred (Bio-Rad, 20 min at 5 V/cm²) to PVDF membranes (NEN Research Products). Blocking, washing and incubation of the membrane with antibodies were carried out in PBS containing 5% non-fat dry milk. The blot was probed using mouse monoclonal antibody against the HA epitope tagged (Pharmacia) as described (Zervos et al., 1995, *Proc. Natl. Acad. Sci. USA*, 92, 10531–10534).

Genomic Cloning and Chromosome localisation of Nmi

A human cosmid library was screened with a radiolabled Nmi DNA fragment as described herein. Three positive clones were isolated. These genomic clones containing about 30 kb of genomic DNA, were digested with EcoRI, and analyzed on Southern blot. A DNA fragment of about 10 kb consistently showed strong signal upon Nmi hybridization and was subcloned into pGEM-4Z vector and partially sequenced. It corresponded to sequence present at the carboxy-terminal of Nmi. This cosmid was used for FISH analysis by BIOS (New Haven, Conn.). Specific labelling was found on human chromosome 22 band q13.3.

For genomic mapping of human Nmi, an Nmi cosmid clone was hybridized to normal metaphase human chromosomes derived from PHA stimulated peripheral blood lymphocytes. Hybridization to the q terminus of chromosomes 22 was observed. The assignment of band position was based on detailed analysis of images from 64 individual chromosomes.

Isolation of genomic clones and FISH analysis was performed essentially as follows. Genomic clones of human Nmi were isolated from a human cosmid library in pWE15 vector (Clontech) using standard procedures (Sambrook et al., 1989, Molecular Cloning—a laboratory manual, Cold Spring Harbor Laboratory Press, NY). Positive clones were digested with EcoR1, separated on a 1% agarose gel, and transferred to a nylon membrane. Southern hybridization was done as described above for Northern analysis. A DNA fragment with a strong hybridization signal with Nmi was subcloned into pGEM-4Z (Promega), and its identity further confirmed by partial DNA sequence. This cosmid clone was used for FISH analysis by BIOS (New Haven,Conn.).

The Nmi nucleotide sequence is accessible under GenBank number U32849.

Isolation and Cloning of Omi cDNA

To isolate Mxi2 interacting proteins, a modified yeast two-hybrid system to screen a HeLa cDNA library was used (Gyuris et al. *Cell* 75:791–803, 1993; Zervos et al. *PNAS USA* 92:10531–10534, 1995). The full length Mxi2 fused to LexA$_{1-220}$ was used as a bait. EGY48 (MATatrp1ura3his3leu2::p3LexA$_{op}$-Leu2) yeast strain was used, with an integrated LEU reporter gene and upstream LexA operators as well as a pSH18-34 (LexA$_{op}$-lacZ) 2μ plasmid that directs the synthesis of β-galactosidase (Gyuris et al. *Cell* 75:791–803, 1993). One million primary yeast colonies were screened, 88 colonies were initially isolated by their ability to grow on Gal-Ura⁻-His⁻-Trp⁻-Leu⁻ selective plates and thus contain a potential interactor. When these were tested on Ura⁻-His⁻-Trp⁻X-gal glucose and Ura⁻-His⁻-Trp⁻X-gal galactose plates only two colonies had an unambiguous galactose-dependent phenotype.

The cDNA library plasmids were isolated from these two colonies and introduced into KC8 *E. coli* by electroporation. Both yeast colonies were shown to have the same cDNA by PCR analysis and partial restriction digest, although one had a longer 3' untranslated sequence. The partial cDNA encoded a polypeptide of 313 amino acids fused in frame to the B42 activation domain of the pJG-4.5 vector (corresponds to nucleotides 898–1834 in FIG. 4a). The complete sequence of the cDNA was determined by sequencing both strands with a commercially available kit (US Biochemicals).

This partial cDNA was used to screen a human fetal brain cDNA library (Clontech) and isolated several clones, the longest of which was 2,040 nucleotides long corresponding to the full length protein called Omi (FIG. 4a). Sequence searches were performed using the BLAST program on the NCBI network server. The sequence data of the human Omi cDNA is accessible under GenBank number AF020760.

This cDNA clone encodes a polypeptide of 529 amino acids and is called Omi with an estimated M$_r$ of 57,073. This cDNA contains an open reading frame of 1626 nucleotides from which the amino acid sequence was deduced. Using point mutations and in vitro transcription-translation experiments it was confirmed that the ATG localized at nucleotide 248 is the initiator methionine. There are stop codons in all three reading frames within the 247 nucleotides of 5' UTR (8 total), including an in frame termination 40 bases upstream of the initiation codon. Two alternatively spliced forms of Omi that encode the same polypeptide were isolated but they have different 3' UTR lengths.

Figure 4B:
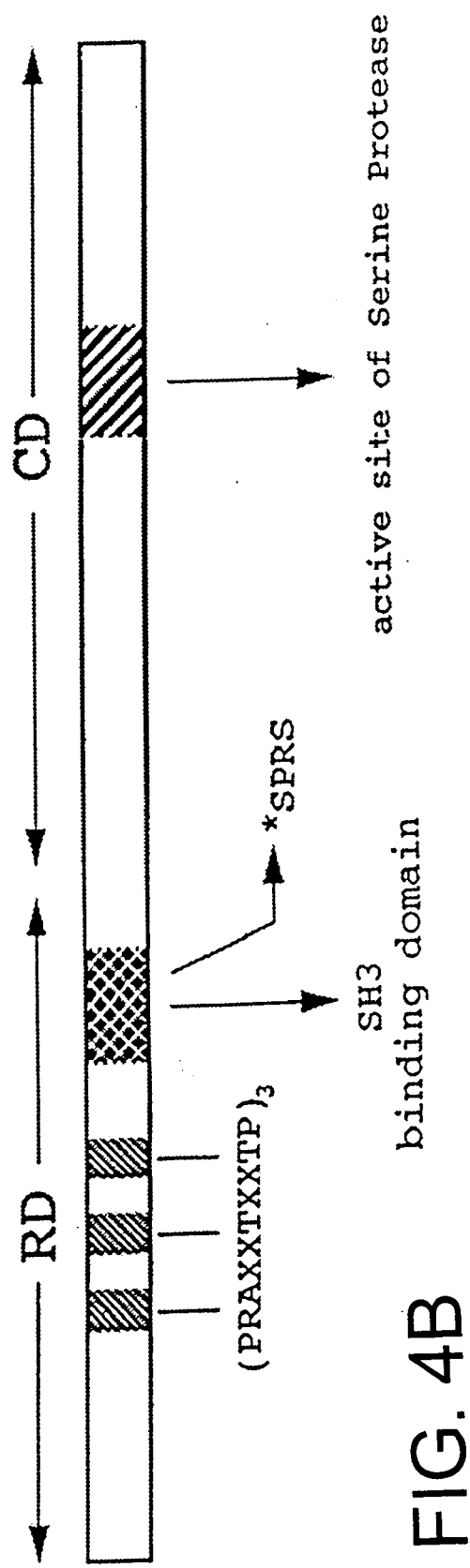
FIG. 4B depicts a schematic diagram of the domain structure of Omi.

Based on homology with other known polypeptides, two domains to the protein were arbitrarily assigned: an amino terminal regulatory domain (RD) and a carboxy terminal serine protease catalytic domain (CD) (FIG. 4b). The regulatory domain has a potential phosphorylation site for Mxi2/p38 kinase kinases at position 215 (S-P-R-S) SEQ ID NO:.

Overlapping with the phosphorylation site there is an SH3 binding domain (P-P-P-A-S-P-R, SEQ ID NO:6) (Cohen et al. *Cell* 80:237–248, 1995; Koch et al. *Science* 252:668–674, 1991). Upstream of this site there is a sequence motif P-R-A-X-X-T-X-X-T-P (where X can be any amino acid) SEQ ID NO:6 which is present three times in the regulatory domain (FIG. 4b).

There is a putative signal peptidase cleavage site between amino acid residues 26 and 27 as predicted according to the rules of Von Heijine (Heijne *Nucleic Acid Research* 14:4683–4690, 1986).

Figure 5B:
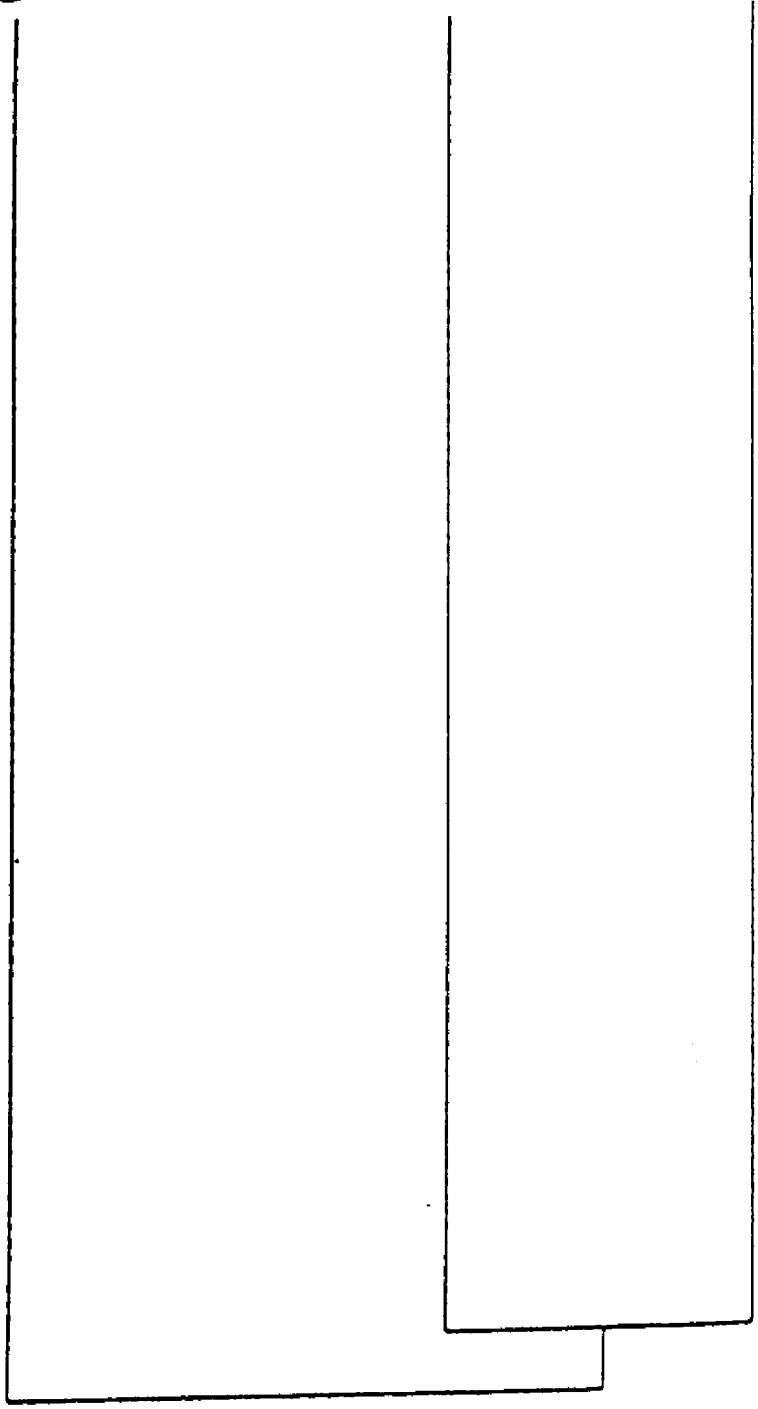
FIG. 5B depicts a phylogram comparing the amino acids of Omi, HtrA and L56 proteases.

The serine protease catalytic domain of Omi shows extensive homology with *E.coli* heat shock protease, HtrA, as well as with a mammalian protein called L56 (Zumbrunn and Trueb *FEBS Lett.* 398:187–192, 1996) (FIG. 5a). No homology is found in the regulatory domains The catalytic domain of Omi has 51% identity and 68% similarity with the corresponding domain of L56, and 36% identity and 58% similarity with HtrA, (FIG. 5b).

Protein sequences were aligned using the Genetics Computer Group (Madison, Wis.) GAP program. The amino acid sequences of Omi, HtrA and L56 proteases were compared using the CLUSTAL W 1.6 program.

Expression of the Omi Gene

To investigate Omi gene expression, Northern blot analyses were performed using mRNA from different human tissues as well as from a number of tumor cell lines. A membrane containing 2 µg of mRNA from the indicated human tissues and with 2 µg of mRNA from different tumor cell lines (Clontech) was probed with $^{32}$P-labeled full length Omi cDNA, as previously described (Bao and Zervos *Oncogene* 12:2171–2176, 1996). Blots were washed at 65° C. with 2% SSC, 0.1% SDS for 10 min. following by 0.1%SSC, 0.1%SDS for 30 min. The blots were then subjected to autoradiography.

Omi has two distinct mRNAs that are expressed ubiquitously, a major one of approximately 2.1 kb and a minor one of 4.5 kb. The highest level of Omi expression is found in placenta and pancreas. In tumor cell lines, high expression of Omi was found in promyelocytic leukemia HL-60, chronic myelogenous leukemia K-562, Burkitt lymphoma Raji and human colorectal carcinoma SW480 cell lines.

Chromosomal Localization

Lymphocytes isolated from human peripheral blood were cultured in a-minimal essential medium (MEM) supplemented with 10% fetal calf serum and phytohemagglutinin (PHA) at 37° C. for 68–72 hr. The lymphocyte cultures were treated with BrdU (0.18 mg/ml Sigma) to synchronize the cell population. The synchronized cells were washed three times with serum-free medium to release the block and recultured at 37° C. for 6 hr in a-MEM with thymidine (2.5 mg/ml Sigma). Cell were harvested and slides were made by using standard procedures including hypotonic treatment, fixed and air dried.

2 kb Omi cDNA probe was biotinylated with dATP using the BRL BioNick labeling kit (15° C., 1 hr) (Heng et al. *PNAS USA* 89:95009–95013, 1992). The procedure for FISH detection was performed according to (Heng et al. *PNAS USA* 89:95009–95013, 1992; Heng and Tsui *Chromosoma* 102:325–332, 1993).

Slides were baked at 55° C. for 1 hr. and after RNase treatment, they were denatured in 70% formamide in 2×SSC for 2 min. at 70° C. and then dehydrated with ethanol. Probe was denatured at 75° C. for 5 min. in a hybridization mix consisting of 50% formamide, 10% dextran sulphate and human cot1 DNA. Probe was loaded on the denatured chromosomal slides. After overnight hybridization, slides were washed and processed for photography. FISH signals and the DAPI banding pattern was recorded separately by taking photographs, and the assignment of the FISH mapping data with chromosomal bands was achieved by superimposing FISH signals with DAPI banded chromosomes (Heng and Tsui "FISH detection of DAPI banded chromosomes". Humana Press, Clinton, N.J., 1994).

The Omi gene is localized on human chromosome 2, region p 12. Translocations and deletions of this region are found in acute and chronic lymphocytic leukemias as well as non-lymphocytic leukemia and Hodgkin disease (Shapiro et al. *Genomics* 23:282–285, 1994).

Production of an Omi Specific Antibody

A polyclonal antibody were raised against Omi to precipitate the endogenous protein. Anti-Omi antibodies were prepared by immunizing rabbits with the C-terminal region of Omi protein (residues 287–529) fused to the Maltose Binding Protein (MBP) (New England Biolabs). The fusion protein was expressed in *E. Coli* and purified using maltose-amylose resin. Affinity purified MBP-Omi was resolved on polyacrylamide gels. The gel pieces containing the MBP-Omi fusion protein were excised and used to inject rabbits (Cocalico Biologicals, Inc). Anti-Omi antibodies were affinity purified on a column of MBP-Omi covalently linked to Sepharose. Immunoblotting was performed using the anti-Omi antiserum at 1:1000 dilution.

The secondary antibody used was a goat anti-rabbit horseradish peroxidase conjugate (Biorad). Visualization of antibody binding was carried out using the ECL detection system (Amersham).

In Vivo Association of Omi with Mxi2

Co-immunoprecipitation (co-IP) experiments using 293 cells transiently transfected with plasmids expressing Mxi2 or p38 as a hemaglutinin epitope-tagged fusions (Mxi2-HA) or (p38-HA), respectively, were performed to study the interaction of Mxi2 and Omi 293 cells were maintained in Dulbecco's modified Eagle's medium (DMEM, Sigma) containing 10% (vol/vol) fetal calf serum (Sigma). All transient transfections were done on 100 mm dishes using the calcium phosphate method (Pear et al., 1993). Briefly, the transfection cocktail was prepared by resuspending 10 µg of DNA in 500 µl of 250 mM $CaCl_2$ and incubating for 30 min at room temperature; the $CaCl_2$ mix was then added to 500 µl of Hepes buffer pH 7.2 while bubbling air through it. The mix was left at RT for 20 minutes and then added to the cells. To evaluate the effect of anisomycin, a known p38 activator, or SB205380, a p38 inhibitor, on the Mxi2-Omi interaction, three days after transfection cells were treated with 10 µg/µl of anisomycin (Calbiochem) for 30 min. or with 20 µM SB205380 (Calbiochem) for 15 min. Cells were then washed with PBS and lysed using 400 µl of 20 mM HEPES pH 7.5, 25% glycerol, 250 mM NaCl 1 mM EDTA, 1 mM DTT, 1% Nonidet P-40.

Lysates were incubated on ice for 30 min. and then centrifuged for 15 min at 14,000 rpm. Preclearing was done by adding 350 µl of TS buffer (20 mM Tris pH 7.5, 140 mM NaCl) and 100 µl of protein G agarose to a 200 µl aliquot of the cell lysate and incubating with rocking for 4 hr at 4° C. The protein G agarose was then removed, the precleared lysates were incubated with 5 µl of Omi polyclonal antibody for 1 hr on ice. After this time 20 µl of protein G agarose beads was added and the lysates were incubated overnight at 4° C.

The beads were washed 4 times with TS buffer and resuspended in 30 µl of 2×SDS loading buffer. The samples were boiled for 5 min. and resolved on 12% polyacrylamide gel, electro-transferred onto PVDF membranes (NEN Research Products) using a Trans-Blot (Bio-Rad). After blocking with 5% non-fat dry milk in PBS, membranes were incubated with the primary antibody in 5% non-fat dry milk. No interaction was detected between p38 kinase and Omi even when p38 was activated by treating cells with anisomycin.

After resolving the precipitated complex on an SDS-PAGE gel, the presence of Mxi2-HA in the complex was detected using anti-HA antibody. These experiments showed that Omi can bind Mxi2 in vivo and that the affinity of the interaction is strong enough to allow protein co-IP.

Mxi2 Activates Omi Through Phosphorylation

To investigate whether Mxi2 can phosphorylate Omi antibodies against Omi were used to precipitate the Omi/Mxi2 complex from mammalian cells previously transfected with pMT3-Mxi2, as described above. Immunoprecipitated complexes containing Omi and HA-Mxi were isolated as described above. They were washed four times with TS buffer and three times with kinase buffer (20 mM MOPS at pH 7.2, 2 mM EGTA, 10 mM MgCl$_2$, 1 mM DTT and 0.1% Triton X-100). Kinase reactions were performed in a final volume of 60 μl of kinase buffer in presence of 75 mM MgCl$_2$, 1 μM cold ATP and 1 μCi/μl of [γ-$^{32}$P] ATP. A control kinase reaction was done in the presence of 2 μg of His-Max made in bacteria. The reactions were incubated for 30 min at 30° C, stopped by addition of 2×SDS loading buffer and analyzed by SDS-PAGE, blotting and autoradiography. Max protein, a known substrate for Mxi2 was also added to some reactions. Phosphorylated Omi is shown as a doublet of phosphorylated polypeptides with a molecular weight of 57–59 kD. Max was also phopshorylated very efficiently.

The activation status of Mxi2 when bound to Omi in the presence of anisomycin or SB205380 was determined. 293 cells were transiently transfected with Mxi2-HA and used anti-Omi antibodies in a co-IP experiment. 293 cells were transfected with HA-Mxi2 and treated with anisomycin or SB205380. HA-Mxi2 was isolated from these cells using HA antibody. The phosphorylation state of Mxi2 was evaluated using phospho-specific antibodies that recognize TGY motif only when both threonine and tyrosine are phosphorylated (New England Biolabs). These results showed Mxi2 in complex with Omi, isolated from 293 cells is active and neither anisomycin nor SB205380 have any effect on its phosphorylation state. HA-Mxi2 was then incubated in kinase buffer with Omi protein isolated from 293 cells using the Omi antibody. Kinase reactions were performed in the presence or absence of Max protein, a known substrate of Mxi2. The autoradiograph shows Omi as well as Max protein was phosphorylated. Anisomycin or SB205380 had no affect on the ability of Mxi2 to phosphorylate either of these two substrates.

Assay of the Proteolytic Activity of Omi

To investigate if phosphorylation of Omi by Mxi2 is involved in the activation of its proteolytic activity, a colorimetric assay using a commercially available kit (Athena Environmental Sciences, Inc) was performed to measure Omi-mediated proteolysis. The assay uses a universal substrate of a dye-protein conjugate cross-linked to a matrix. The matrix is supplied in glass vials ready-to-use. Protease activity is determined spectrophotometrically by measuring the absorbance of the dye released from the matrix to the supernatant. HA-Mxi2 was isolated from 293 cells transiently transfected with HA-Mxi2. Anti-Omi antibodies were used to isolate endogenous Omi protein. The immunoprecipitates were washed four times with TS buffer and three times with kinase buffer. Ha-Mxi2 was mixed with Omi in kinase buffer. Half of the aliquots were phosphorylated by adding [γ-$^{32}$P] ATP as described above. The rest of the aliquots represented non-phosphorylated control Omi. Kinase reactions were performed at 30° C. for 30 min. After this time the reactions were added to 440 μl of 10 mM Tris-HCl pH 7.5 and placed in the reaction vials containing the matrix-substrate. The activity of phosphorylated Omi as well as the non-phosphorylated control was measured at different times. At the end of the incubation time, reactions were stopped by adding 500 μl of 0.2 N NaOH to each vial. The absorbance of the supernatant in each vial was measured at 450 nm. The experiment was performed in triplicate with three independent measurements.

Figure 6:
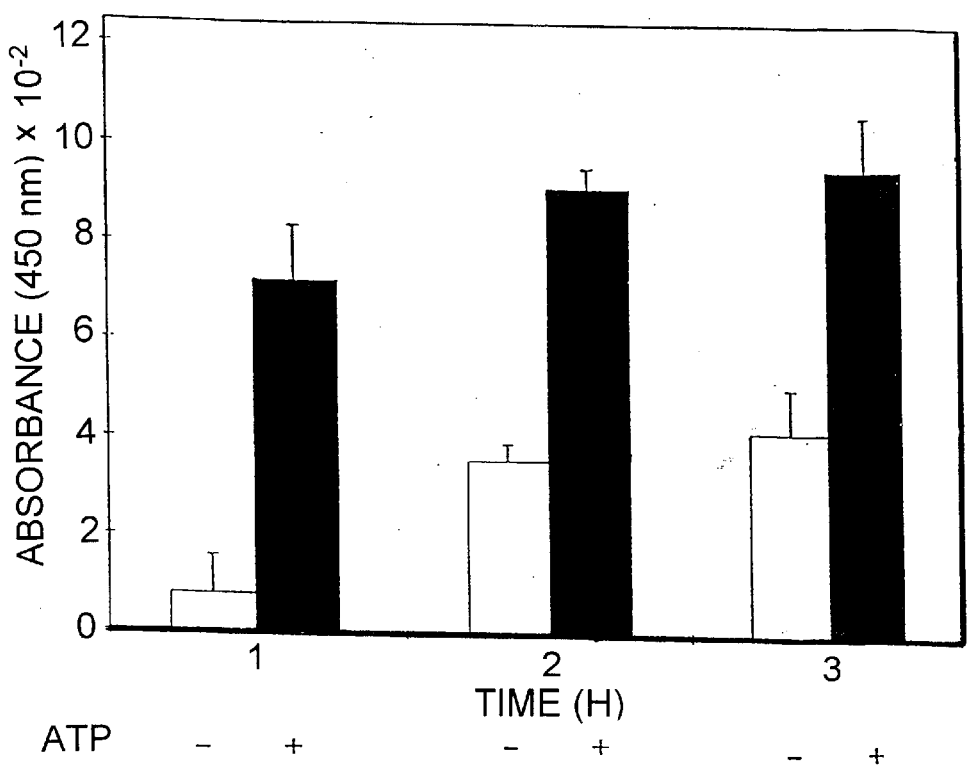
FIG. 6 depicts a bar graph depicting the proteolytic activity of Omi.

The results showed the proteolytic activity of Omi increases dramatically when phosphorylated by Mxi2 (FIG. 6).

Analysis of Omi Sequences

A GenBank™ search using the human Omi nucleotide sequence of SEQ ID NO:4, revealed 44 human EST which were at least 80% identical to different regions of the nucleotide sequence of SEQ ID NO:4. The EST sequences having greater than 80% identity are listed in Table 1, as well as, the nucleotide and amino acid sequences of SEQ ID NO:4 and SEQ ID NO:5, respectively, to which each EST sequence corresponds.

TABLE 1

EST SEQUENCE ANALYSIS

| Accession No. | SPECIES | nucleotides of BST | corresponding nucleotide sequence of human Omi (SEQ ID NO:4) | corresponding amino acid sequence of human Omi (SEQ ID NO:5) |
|---|---|---|---|---|
| AA643031 | human | 697-10 | 1337-2026 | 364-529 |
| AA781400 | human | 508-1 | 1454-1461 | 403-529 |
| AA741018 | human | 500-10 | 1535-2026 | 430-529 |
| N62285 | human | 450-32 | 1409-1826 | 388-527 |
| AA563687 | human | 420-4 | 1604-2023 | 453-529 |
| AA732865 | human | 410-1 | 1442-1853 | 399-529 |
| AA699831 | human | 6-405 | 8-407 | 1-54 |
| AA670302 | human | 404-4 | 1625-2026 | 460-529 |
| W74667 | human | 407-4 | 1623-2026 | 459-529 |
| AA100639 | human | 391-6 | 1640-2026 | 465-529 |
| M79154 | human | 399-1 | 1609-2006 | 443-529 |
| AA468669 | human | 369-1 | 1655-2026 | 470-529 |
| AA084255 | human | 383-4 | 1649-2026 | 468-529 |
| AA743709 | human | 397-43 | 1671-2026 | 475-529 |
| AA743709 | human | 554-397 | 1418-1575 | 391-443 |
| N77446 | human | 340-4 | 8-343 | 1-32 |
| AA627768 | human | 3-352 | 8-356 | 1-37 |
| AA100626 | human | 1-374 | 1630-1999 | 561-529 |
| AA385242 | human | 1-319 | 1264-1582 | 339-445 |
| AA191602 | human | 512-155 | 1670-2026 | 475-529 |
| W74773 | human | 1-352 | 1623-1971 | 459-529 |
| R48552 | human | 374-1 | 1654-2026 | 436-529 |
| M28888 | human | 354-1 | 1671-2022 | 475-529 |
| AA252639 | human | 1-366 | 666-1032 | 139-262 |
| T80727 | human | 1-334 | 1043-1371 | 256-375 |
| AA341610 | human | 1-287 | 1282-1568 | 345-441 |
| AA506052 | human | 316-12 | 1721-2026 | 492-529 |
| R55706 | human | 454-156 | 1730-2026 | 495-529 |
| W38532 | human | 272-10 | 8-271 | 1-9 |
| AA302550 | human | 265-9 | 100-356 | 1-37 |
| AA090372 | human | 1-268 | 1098-1368 | 284-374 |
| T80108 | human | 8-371 | 674-1035 | 143-263 |
| N77445 | human | 239-6 | 109-342 | 1-32 |
| AA928585 | human | 44-277 | 20-253 | 1-2 |
| N64298 | human | 1-255 | 1636-1891 | 463-529 |
| AA362632 | human | 1-256 | 904-1159 | 219-304 |
| AA084254 | human | 9-269 | 646-906 | 133-220 |
| AA687369 | human | 387-165 | 1803-2026 | 519-529 |
| M78978 | human | 241-1 | 1772-2013 | 509-529 |
| R48646 | human | 1-135 | 1266-1400 | 340-385 |
| N26352 | human | 412-287 | 134-259 | 1-4 |
| N26352 | human | 288-151 | 270-407 | 1-54 |
| AA311431 | human | 39-165 | 915-1041 | 224-265 |

Cloning of Rim cDNA

Poly-A RNA was isolated from human foreskin keratinocytes, expanded in culture as a mixed population of actively growing and differentiated cells. This RNA was used to make cDNA and cloned unidirectionally as EcoRI/Xhol in the corresponding sites of pJG4-5 (Gyuris et al., 1993, Cell 75: 791–803).

This keratinocyte cDNA library had 3.5×10$^6$ independent transformants with cDNA insert sizes of 0.4 Kb to 3 Kb. A modified yeast two-hybrid system was used to screen the human keratinocyte cDNA library for Max interacting proteins (Gyuris et al., 10 1993, Cell 75: 791–803; Zervos et al., 1993, Cell 72: 223–232). The bait protein used was the full length Max polypeptide fused to LexA (Zervos et al., 1993, Cell 72: 223–232). Two reporter genes were used in the screen, a very sensitive LexAop-LEU2 gene that allows growth in the absence of leucine, and a LexAop-lacZ gene that directs the synthesis of β-galactosidase (Gyuris et al., 1993, Cell 75: 791–803). One million primary yeast colonies were screened for potential cDNAs encoding novel Max-interacting proteins. 400 colonies were initially identified and isolated by their ability to grow on Gal-Ura⁻-His⁻-Trp⁻-Leu⁻selective plates. When these were tested on Ura⁻-His⁻-Trp⁻X-gal glucose and Ura⁻-Hi⁻-Trp⁻X-gal galactose plates, 55 colonies had a consistent galactose-dependent phenotype. After further analysis, eleven clones showed an unambiguous phenotype. The cDNA library plasmids were rescued from these positive yeast colonies and introduced into KC8 cells by electroporation. These cDNAs were analyzed using a combination of PCR and partial restriction mapping. They were sequenced using the Sequenase kit (USB). Homology searches were performed using BLAST and Ψ-BLAST computer programs on a NCBI server (http://www.ncbi.nlm.nih.gov/BLAST/) (Altschul et al., 1990, *J. Mol. Biol.* 215: 403–410; Altschul et al., 1997, *Nucleic Acids Res.* 25: 3389–3402). Among the positive clones were several known Max-interacting proteins, including C-myc, L-myc, and Mad4 (Luscher and Eisenman, 1990, *Genes Dev.* 4: 2025–2035; Hurlin et al., 1995, *EMBO J.* 14: 5646–5659).

Figure 8:
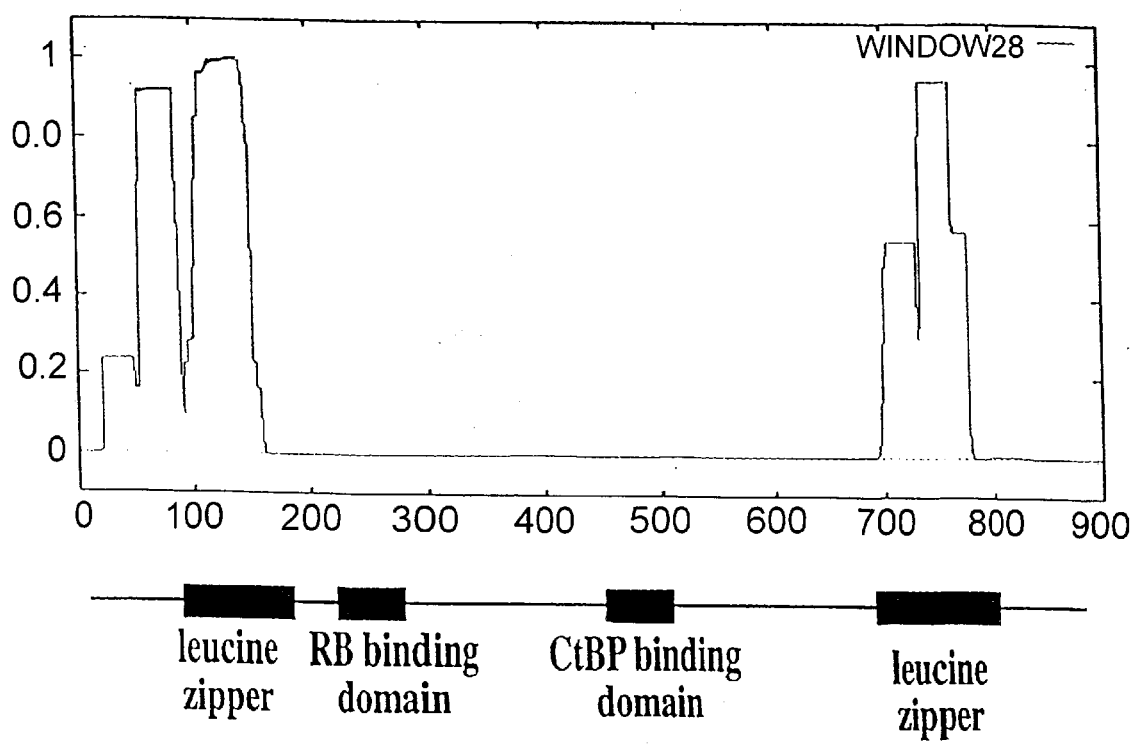
FIG. 8 depicts a computer prediction of coiled-coil elements on Rim that correspond to the two potential leucine zipper motifs shown on the schematic diagram. The corresponding location of the RB binding domain as well as the CtBP domain are also shown.

One of the clones, clone 32.2, encoded for a novel polypeptide of 756 amino acids (p32.2) fused in frame with the B42 activation domain of the pJG-4.5 vector. This cDNA sequence was used to search the IMAGE consortium database for homologous EST clones. One such EST clone (610839) (corresponding to EST AA172171 (SEQ ID NO:13) or EST AA172324 (SEQ ID NO:14) (as shown in Table 1) was found to represent a cDNA of 3246 nucleotides and included the full length sequence of the original 32.2 cDNA, which was isolated in the yeast two-hybrid screen. This EST cDNA had 297 nucleotides of 5' end untranslated sequence with stop codons in all three reading frames, and 255 3' end non-coding sequence (FIG. 7). The original cDNA clone was isolated in a yeast two-hybrid screen and encodes 756 residues, corresponding to nucleotides 424–2694. The full length EST cDNA contains an open reading frame of 2691 nucleotides from which the amino acid sequence of 897 residues was deduced, with a predicted molecular weight of approximately 102 kDa. The 5' UTR of the EST cDNA consists of 298 nucleotides. The deduced amino acid sequence of the Rim polypeptide includes two potential coiled-coil leucine zipper structures one at the amino terminus and the other closer to the carboxy terminus of the protein, (amino acids 120–141 and 740–761 of SEQ ID NO:10, respectively), a consensus RB family binding motif having the amino acid sequence LXCXE (SEQ ID NO:11), where X can be any amino acid) (corresponding to 153–157 of SEQ ID NO:10), an E1A/CtBP binding motif (amino acids 740–761 of SEQ ID NO:10), and four putative nuclear localization sequences (located approximately at positions 355–358, 446–449, 877–880, and 878–881 of SEQ ID NO:10 (FIG. 8).

Deletional Mapping

To map the interaction domain(s) on Rim responsible for its binding to the RB family of proteins, a number of deletion mutants were made and each tested in a yeast two-hybrid assay. LexA-fusion proteins were expressed in RFY206 yeast strain and tested for interaction with the following deletion mutant proteins expressed in EGY48 (MAT-α) yeast strain: Rim$_{1-897}$; Rim$_{147-897}$, Rim,$_{1-682}$, Rim$_{1-487}$, Rim, $_{1-141}$, and Rim$_{1-99}$. A minimal sequence required for binding to RB proteins was found that includes the LECEE amino acid motif. Rim has four potential nuclear localization signals suggesting that it is a nuclear protein. When the epitoped tagged Rim was overexpressed in COS cells, Rim was found to be mostly cytoplasmic. RB protein can be found in the cytoplasm as well as in the cell nucleus (Yen et al., 1997, Eur. *J. Cell Biol.* 72: 159–165).

Rim has also a PLDLS (SEQ ID NO:12) amino acid sequence (starting at amino acid 510) that represents a CtBP binding motif. This motif was originally identified in E1A viral protein, which interacts with the cellular CtBP polypeptide (Boyd et al., 1993, *EMBO J.* 12: 469–478; Shaeper et al., 1995, *Proc. Natl. Acad. Sci. USA* 92: 10467–10471; Sollerbrant et al., 1996, *Nucleic Acids. Res.* 24: 2578–2584). The presence of the CtBP binding motif as well as the RB binding domain strongly suggests that Rim has a role in the regulation of cell cycle.

Proximal to the first leucine zipper domain at position 152, the sequence LECEE (SEQ ID NO:16) is found which resembles a consensus sequence for an RB binding domain (Figge et al., 1988, *J. Virol.* 62(5):1814–1818; Taya, 1997, *Trends Biochem. Sci.* 22: 14–17). A computer analysis using the Ψ-Blast program showed weak homology throughout the entire protein with myosin family of proteins suggesting Rim may have a rod-type structure and may be part of a cellular scaffold (Atkinson and Stewart, 1991, *J. Cell. Sci.* 14: 7–10; Faruqi et al., 1993, *Adv. Exp. Med Biol.* 332: 81–89) (28% of homology and the index T=0) (Altschul et al., 1997, *Nucleic Acids Res.* 25: 3389–3402). Thus, this protein was named Rim for Retinoblastoma Interacting Myosin-like.

The specificity of protein encoded by clone 32.2 to interact with a panel of over 1600 different baits was performed using the yeast mating assay (Finley et al. (1994) *Proc. Natl. Acad. Sci. USA* 91(26):12980–12984). The only interactions found were between Rim and RB, p107, or p130 proteins. These interactions occurred whether the partial p32.2$_{181-897}$ or the full length Rim protein was used. The fusion protein encoded by the cDNA isolated in the yeast two-hybrid screen was able to bind Max, as well as the carboxy terminus of Myc, but not other helix-loop-helix-Zip proteins. When this full length protein was tested in the yeast two-hybrid system for interaction with Max, unexpectedly it did not interact. The presence of the amino terminal sequence, absent in the original p32.2 protein which did contain the amino terminal leucine zipper domain, may change the overall conformation of the Rim protein. This in turn may hide the Max interacting domain on the Rim protein. The conformation of Rim may change through phosphorylation or any other post-translational mechanism to allow interaction with Max.

Expression of Rim mRNA

Northern blot analysis was performed using 2 μg of mRNA from different adult human tissues and tumor cell lines and was probed with the full length Rim cDNA (Clontech) (Bao and Zervos, 1996, *Oncogene* 12: 2171–2176). The blots were hybridized at 42° C. with the full length radiolabeled 32.2 cDNA probe. Blots were then washed at 65° C. for 10 min with 2% SSC, 0.1% SDS, followed by a 30 min wash with 0.1% SSC, 0.1% SDS. The membranes were exposed to X-ray film (Kodak) with intensifying screens at −70° C. A single mRNA band of approximately 3.6 Kb is detected in all the tissues. mRNA is expressed at very low levels in all terminally differentiated human tissues tested. The highest level of expression occurs in pancreas. Higher levels of Rim mRNA were found in several transformed cell lines. In tumor cell lines, high expression of Rim mRNA is found in promyelocytic leukemia HL-60, chronic myelogenous leukemia K-562, lymphoblastic leukemia MOLT-4, Burkitt lymphoma Raji, and human colorectal carcinoma SW480 cell lines.

When epitoped tagged Rim was overexpressed in COS cells, Rim was mostly cytoplasmic. RB protein can be found in the cytoplasm as well as in the cell nucleus (Yen et al., 1997, Eur. J. Cell Biol. 72: 159–165). Rim-RB interactions in mammalian cells may occur in the cytoplasm, but the nature of its physiological role is not established.

Chromosomal Localization

The chromosomal localization of Rim was mapped using FISH analysis. Lymphocytes isolated from human peripheral blood were cultured in essential medium (MEM) supplemented with 10% fetal calf serum and phytohemagglutinin (PHA) at 37° C. for 68–72 hrs. The lymphocyte cultures were treated with 0.18 mg/ml BrdU (Sigma) to synchronize the cell population. The synchronized cells were washed three times with serum-free medium to release the block and recultured at 37° C. for 6 hrs in a-MEM with 2.5 mg/ml thymidine (Sigma). Cells were harvested and slides were made using standard procedures, which included hypotonic treatment, paraformaldehyde fixation and air dried. Slides were baked at 55° C. for 1 hr and after RNase treatment, denatured with 70% formamide in 2×SSC for 2 min at 70° C., then dehydrated with ethanol.

The 32.2 cDNA probe (approximately 2.4 kb) was biotinylated with dATP using the Bionick kit (Gifco BRL). The probe was denature at 75° C. for 5 min in a hybridization mix consisting of 50% formamide and 10% dextran sulphate with human Cot-1 DNA. The procedure for FISH detection was performed using standard conditions (Heng et al., 1992, Proc. Natl. Acad Sci. USA 89: 9509–95013; Heng and Tsui, 1993, Chromosoma 102: 325–332).

The probe was loaded on the denatured chromosomal slides. After overnight hybridization, slides were washed and processed for photography. FISH signals and the DAPI banding pattern were photographed separately and the assignment of the FISH mapping data with chromosomal bands was achieved by superimposing FISH signals over DAPI banded chromosomes (Heng and Tsui, 1994, In "Methods in molecular biology: In situ hybridization protocol" pp. 35–49 Humana Press, Clifton, N.J.).

The Rim gene was localized on human chromosome 18, region q11.1–2. No significant deletions or rearrangements implicated in the development or progression of any human malignancies or other genetic conditions have been reported to be associated with this area.

Analysis of Rim Sequences

A GenBank™ search using the human Rim nucleotide sequence of SEQ ID NO:9, revealed 2 human EST which were at least 80% identical to different regions of the nucleotide sequence of SEQ ID NO:9. The EST sequences having greater than 80% identity are listed in Table 2.

TABLE 2

EST SEQUENCE ANALYSIS

| Accession No. | SPE-CIES | nucleotides of EST | corresponding nucleotide sequence of human Rim (SEQ ID NO:9) | corresponding amino acid sequence of human Rim (SEQ ID NO:10) | % Identity |
|---|---|---|---|---|---|
| AA172171 | human | 404-1 | 2524-2939 | 842-897 | 100 |
| AA172324 | human | 1-107 | 302-407 | 1-36 | 100 |

Analogs of Nmi, Omi and Rim

Analogs can differ from naturally occurring Nmi, Omi or Rim in amino acid sequence or in ways that do not involve sequence, or both. Non-sequence modifications include in vivo or in vitro chemical derivatization of Nmi, Omi or Rim. Non-sequence modifications include changes in acetylation, methylation, phosphorylation, carboxylation, or glycosylation.

Preferred analogs include Nmi, Omi or Rim (or biologically active fragments thereof) whose sequences differ from the wild-type sequence by one or more conservative amino acid substitutions or by one or more non-conservative amino acid substitutions, deletions, or insertions which do not abolish the Nmi, Omi or Rim biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 3

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |

TABLE 3-continued

CONSERVATIVE AMINO ACID REPLACEMENTS

| For Amino Acid | Code | Replace with any of |
|---|---|---|
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or phenylproline, cis-3,4, or 5-phenylproline |
| Proline | P | D-Pro, L-I-thioazolidine-4-carboxylic acid, D-or L-I-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Gene Therapy

The gene constructs of the invention can also be used as a part of a gene therapy protocol to deliver nucleic acids encoding either an agonistic or antagonistic form of an Nmi, Omi or Rim polypeptide. The invention features expression vectors for in vivo transfection and expression of an Nmi, Omi or Rim polypeptide in particular cell types so as to reconstitute the function of, or alternatively, antagonize the function of an Nmi, Omi or Rim polypeptide in a cell in which that polypeptide is misexpressed. Expression constructs of Nmi, Omi or Rim polypeptides, may be administered in any biologically effective carrier, e.g. any formulation or composition capable of effectively delivering the Nmi, Omi or Rim gene to cells in vivo.

Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO$_4$ precipitation carried out in vivo.

A preferred approach for in vivo introduction of nucleic acid into a cell is by use of a viral vector containing nucleic acid, e.g. a cDNA, encoding an Nmi, Omi or Rim polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. 1990 *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, 1989, Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. 1985 *Science* 230:1395–1398; Danos and Mulligan 1988 *Proc. Natl. Acad Sci. USA* 85:6460–6464; Wilson et al. 1988 *Proc. Natl. Acad Sci. USA* 85:3014–3018; Armentano et al. 1990 *Proc. Natl. Acad. Sci. USA* 87:6141–6145; Huber et al. 1991 *Proc. Natl. Acad. Sci. USA* 88:8039–8043; Ferry et al. 1991 *Proc. Natl. Acad. Sci. USA* 88:8377–8381; Chowdhury et al. 1991 *Science* 254:1802–1805; van Beusechem et al. 1992 *Proc. Natl. Acad. Sci. USA* 89:7640–7644; Kay et al. 1992 Human Gene Therapy 3:641–647; Dai et al. 1992 *Proc. Natl. Acad. Sci. USA* 89:10892–10895; Hwu et al. 1993 *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. 1988 *BioTechniques* 6:616; Rosenfeld et al. 1991 *Science* 252:431–434; and Rosenfeld et al. 1992 *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. 1992 cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham 1986 *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* 1992 158:97–129). It is also one of the few viruses that may integrate its DNA into non-dividing cells, and exhibits a high frequency of stable integration (see for example Flotte et al. 1992 *Am. J. Respir. Cell. Mol. Biol.* 7:349–356; Samulski et al. 1989 *J. Virol.* 63:3822–3828; and McLaughlin et al. 1989 *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. 1985 *Mol. Cell. Biol.* 5:3251–3260 can be used to introduce DNA into cells. A variety of nucleic acids have been introduced into different cell types using AAV vectors (see for example Hermonat et al. 1984 *Proc. Natl. Acad. Sci. USA* 81:6466–6470; Tratschin et al. 1985 *Mol. Cell. Biol.* 4:2072–2081; Wondisford et al. 1988 *Mol. Endocrinol.* 2:32–39; Tratschin et al. 1984 *J. Virol.* 51:611–619;and Flotte et al. 1993 *J. Biol. Chem.* 268:3781–3790).

In addition to viral transfer methods, such as those illustrated above, non-viral methods can also be employed to cause expression of an Nmi, Omi or Rim polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Omi gene by the targeted cell. Exemplary gene delivery systems of this type include liposomal derived systems, poly-lysine conjugates, and artificial viral envelopes.

In a representative embodiment, a gene encoding an Nmi, Omi or Rim polypeptide can be entrapped in liposomes bearing positive charges on their surface (e.g., lipofectins) and (optionally) which are tagged with antibodies against cell surface antigens of the target tissue (Mizuno et al. 1992 *No Shinkei Geka* 20:547–551; PCT publication WO91/ 06309; Japanese patent application 1047381; and European patent publication EP-A-43075).

In clinical settings, the gene delivery systems for the therapeutic Nmi, Omi or Rim gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. 1994 *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Transgenic Animals

The invention includes transgenic animals which include cells (of that animal) which contain an Nmi, Omi or Rim transgene and which preferably (though optionally) express (or misexpress) an endogenous or exogenous Nmi, Omi or Rim gene in one or more cells in the animal. The Nmi, Omi or Rim transgene can encode the wild-type form of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns, e.g., to restrict production to the milk or other secreted product of the animal.

Production of Fragments and Analogs

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A 1983 *Tetrahedron* 39:3; Itakura et al. (1981) *Recombinant DNA, Proc* 3rd *Cleveland Sympos. Macromolecules*, ed. A G Walton, Amsterdam: Elsevier pp273–289; Itakura et al. 1984 *Annu. Rev. Biochem.* 53:323; Itakura et al. 1984 Science 198:1056; Ike et al. 1983 Nucleic Acid Res. 11:477. Such techniques have been employed in the directed evolution of other proteins (see, for example, Scott et al. 1990 *Science* 249:386–390; Roberts et al. 1992 *PNAS* 89:2429–2433; Devlin et al. 1990 *Science* 249: 404–406; Cwirla et al. 1990 *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765 [1978]).

Cassette Mutagenesis

Another method for preparing variants, cassette mutagenesis, is based on the technique described by Wells et al. (*Gene*, 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to other Nmi, Omi or Rim fragments, binding to natural ligands or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays such as the system described above (as with the other screening methods described herein), can be used to identify fragments or analogs (see e.g., U.S. Pat. No. :5,283,317; PCT publication WO94/10300; Zervos et al. 1993 Cell 72:223–232; Madura et al. 1993 J Biol Chem 268:12046–12054; Bartel et al. 1993 Biotechniques 14:920–924; and Iwabuchi et al. 1993 Oncogene 8:1693–1696). These may include agonists, superagonists, and antagonists. (The subject protein and a protein it interacts with are used as the bait protein and fish proteins). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., an Omi molecule or a fragment thereof, e.g., a regulatory domain triple repeat motif, e.g., a SH3 binding domain, e.g., a consensus phosphorylation site, e.g., and/or a serine protease binding domain of Omi. The second hybrid protein contains a transcriptional activation domain fused to a "fish" protein, e.g. an expression library, e.g., a HeLa cDNA expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. 1991 Bio/Technology 9:1370–1 371; and Goward et al. 1992 TIBS 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. 1992 J. Biol. Chem. 267:16007–16010; Griffiths et al. 1993 EMBO J 12:725–734; Clackson et al. 1991 Nature 352:624–628; and Barbas et al. 1992 PNAS 89:4457–4461).

A common approach uses the maltose receptor of E. coli (the outer membrane protein, LamB) as a peptide fusion partner (Charbit et al. 1986 EMBO 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. 1991 Vaccines 91, pp. 387–392), PhoE (Agterberg, et al. 1990 Gene 88, 37–45), and PAL (Fuchs et al. 1991 Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. 1989 Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. 1988 Bio/Tech. 6, 1080–1083). Surface proteins of other bacterial species have also served as peptide fusion partners. Examples include the Staphylococcus protein A and the outer membrane protease IgA of Neisseria (Hansson et al. 1992 J. Bacteriol. 174, 4239–4245 and Klauser et al. 1990 EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein Lacd to form a link between peptide and DNA (Cull et al. 1992 *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. 1992 *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. 1990 *Proc. Natl. Acad. Sci. U.S.A.* 87, 6378–6382) A second difference is the set of biological biases affecting the population of peptides actually present in the libraries. The Lacd fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the Lacd and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. 1994 *J. Med. Chem.* 37(9):1233–1251). These particular biases are not a factor in the Lacd display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. 1994 *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. 1992 *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject Nmi, Omi or Rim polypeptides to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. 1986 *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. 1985 *Tetrahedron Lett* 26:647; and Sato et al. 1986 J Chem Soc Perkin Trans 1:1231), and β-aminoalcohols (Gordon et al. 1985 *Biochem Biophys Res Commun* 126:419; and Dann et al. 1986 *Biochem Biophys Res Commun* 134:71).

Antibodies

The invention also includes antibodies specifically reactive with a subject Nmi, Omi or Rim polypeptide. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

Antibodies which specifically bind Nmi, Omi or Rim epitopes can also be used in immunohistochemical staining of tissue samples in order to evaluate the abundance and pattern of expression of Omi. Anti-Omi antibodies can be used diagnostically in immuno-precipitation and immuno-blotting to detect and evaluate Omi levels in tissue or bodily fluid as part of a clinical testing procedure.

Another application of antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject polypeptide can then be detected with antibodies, as, for example, reacting nitrocellulose filters lifted from infected plates with antibodies of the invention. Phage, scored by this assay, can then be isolated from the infected plate. Thus, the presence of homologs can be detected and cloned from other animals, and alternate isoforms (including splicing variants) can be detected and cloned from human sources.

Other Embodiments

Included in the invention are: allelic variations; natural mutants; induced mutants; proteins encoded by DNA that hybridizes under high or low stringency conditions to a nucleic acid which encodes a polypeptide SEQ ID NO:1 or 16, 4 or 9, or 10 (for definitions of high and low stringency see Current Protocols in Molecular Biology, John Wiley & Sons, New York, 1989, 6.3.1–6.3.6, hereby incorporated by reference); and, polypeptides specifically bound by antisera to Nmi, Omi or Rim.

Nucleic acids and polypeptides of the invention includes those that differ from the sequences discolosed herein by virtue of sequencing errors in the disclosed sequences.

The invention also includes fragments, preferably biologically active fragments, or analogs of Nmi, Omi or Rim. High stringency conditions for aqueous hybridization can be conducted at 65° C., using the high stringency wash buffer, 1 mM $Na_2EDTA$; 40 mM $NaHPO_4$, pH 7.2; and 1% SDS, and include multiple quick washes (5–8) and immerse in a final wash for 20 minutes (Current Protocols in Molecular Biology, John Wiley & Sons, New York, 1989, 6.3.1–6.3.6). A biologically active fragment or analog is one having any in vivo or in vitro activity which is characteristic of Nmi, Omi or Rim shown in SEQ ID NO:1 or 16, 4 or 9 or 10, or of other naturally occurring Nmi, Omi or Rim, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Particularly preferred fragments are fragments, e.g., active fragments, which are generated by proteolytic cleavage or alternative splicing events.

Other embodiments are within the following claims.

What is claimed is:

1. An isolated Nmi encoding nucleic acid, which encodes a polypeptide capable of promoting the dimerization of a protein containing one or more of: a basic-helix-loop-helix-leucine zipper (bHLH-Zip) motif, a basic-helix-loop-helix (bHLH) motif, or a basic-leucinie zipper (bZip) motif, and having an amino acid sequence which is at least 90% homologous to the amino acid sequence of SEQ ID NO:16.

2. The nucleic acid of claim 1, which encodes a polypeptide having an amino acid sequence which is at least 98% homologous to the amino acid sequence of SEQ ID NO:16.

3. The nucleic acid of claim 1, which encodes a polypeptide which binds to a myc gene product.

4. A vector comprising the nucleic acid of claim 1.

5. A host cell comprising the vector of claim 4.

6. A method of producing a Nmi polypeptide, comprising culturing the cell of claim 5.

7. The nucleic acid of claim 1, which encodes a polypeptide which differs in amino acid sequence by up to 1, 2, 3, 5, or 10 residues, from the sequence in SEQ ID NO:16.

8. The nucleic acid of claim 1, which encodes a polypeptide having an amino acid sequence which is at least 95% homologous to the amino acid sequence of SEQ ID NO:16.

9. An isolated Nmi encoding nucleic acid, which encodes a polypeptide having at least 90% homology with residues 102 to 307 of SEQ ID NO:16 and having the ability to promote the dimerization of a protein containing one or more of: a basic-helix-loop-helix-leucine zipper (bHLH-Zip) motif, a basic-helix-loop-helix (bHLH) motif, or a basic-leucine zipper (bZip) motif.

10. The nucleic acid of claim 9, which encodes a polypeptide comprising residues 102 to 307 of SEQ ID NO:16.

11. An isolated Nmi encoding nucleic acid, which hybridizes under highly stringent conditions to the full complement of SEQ ID NO:1 and which encodes a polypeptide capable of promoting the dimerization of a protein containing one or more of the following: a) a basic-helix-loop-helix-leucine-zipper(bHLH-Zip) motif, b) a basic-helix-loop-helix (bHLH) motif, or c) a basic-leucine zipper (b-ZIP motif, or its full complement.

12. A vector comprising the nucleic acid of claim 11.

13. The nucleic acid of claim 11, which encodes a polypeptide which binds to a myc gene product.

14. The nucleic acid of claim 13, wherein the myc product is selected from the group consisting of N-myc, C-myc, Max and Mxil protein.

15. The nucleic acid of claim 13, wherein the myc product is selected from the group consisting of N-myc, C-myc, Max and Mxil protein.

16. A probe, which has at least 99% homology with, and comprises at least 50 contiguous nucleotides of SEQ ID NO:1.

17. Tithe probe of claim 16, which comprises at least 100 contiguous nucleotides of SEQ ID NO: 1.

18. An isolated Nmi encoding nucleic acid, said nucleic acid having a nucleotide sequence which is at least 90% homologous to the nucleotide sequence of SEQ ID NO:1 and which encodes a polypeptide capable of promoting the dimerization of a protein containing one or more of: a basic-helix-loop-helix-leucine zipper (bHLH-Zip) motif, a basic-helix-loop-helix (bHLH) motif, or a basic-leucine zipper (bZip) motif.

19. The nucleic acid of claim 18, said nucleic acid having a nucleotide sequence which is at least 98% homologous to the nucleotide sequence of SEQ ID NO:1.

20. An isolated nucleic acid comprising the nucleotide sequence of SEQ ID NO:1.

21. An isolated nucleic acid which encodes a polypeptide comprising the amino acid sequence of SEQ ID NO:16.

22. An isolated Nmi encoding nucleic acid, which encodes a polypeptide having at least 90% homology with residues 2 to 86 of SEQ ID NO:16 and having the ability to promote the dimerization of a protein containing one or more of: a basic-helix-loop-helix-leucine zipper (bHLH-Zip) motif, a basic-helix-loop-helix (bHLH) motif, or a basic-leucine zipper (bZip) motif.

23. The nucleic acid of claim 22, which encodes a polypeptide comprising residues 2 to 86 SEQ ID NO:16.

24. An isolated Nmi encoding nucleic acid, which hybridizes under highly stringent conditions to the full complement a nucleic acid which encodes a polypeptide having the amino acid sequence of SEQ ID NO:16 and which has the ability to promote the dimerization of a protein containing one or more of the following: a) a basic-helix-loop-helix-leucine-zipper(bHLH-Zip) motif, b) a basic-helix-loop-helix (bHLH) motif, or c) a basic-leucine zipper (b-ZIP motif), or its full complement.

25. The nucleic acid of claim 18, said nucleic acid having a nucleotide sequence which is at least 95% homologous to the nucleotide of SEQ ID NO:1.

26. A vector comprising the nucleic acid of claim 20.
27. A vector comprising the nucleic acid of claim 21.
28. A vector comprising the nucleic acid of claim 24.
29. A host cell comprising the vector of claim 12.
30. A host cell comprising the vector of claim 26.
31. A host cell comprising the vector of claim 27.
32. A host cell comprising the vector of claim 28.

\* \* \* \* \*

UNITED STATES PATENT AND TRADEMARK OFFICE
CERTIFICATE OF CORRECTION

PATENT NO. : 6,489,136 B1
DATED : December 3, 2002
INVENTOR(S) : Antonis S. Zervos It is certified that error appears in the above-identified patent and that said Letters Patent is hereby corrected as shown below:

Column 98,
Line 39, "claim 13" should read as -- claim 3 --.
Line 63, "acid which" should read as -- acid, which --.

Signed and Sealed this

Seventh Day of October, 2003

JAMES E. ROGAN
*Director of the United States Patent and Trademark Office*